(12) United States Patent
Bhattacharyya et al.

(10) Patent No.: US 8,283,116 B1
(45) Date of Patent: Oct. 9, 2012

(54) METHODS OF SCREENING FOR COMPOUNDS FOR TREATING SPINAL MUSCULAR ATROPHY USING SMN MRNA TRANSLATION REGULATION

(75) Inventors: Anuradha Bhattacharyya, Edison, NJ (US); Bansri S. Furia, Edison, NJ (US); Meenal Patel, Fairless Hills, PA (US); Sergey V. Paushkin, Belle Mead, NJ (US); Love Volkova, Upland, CA (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 476 days.

(21) Appl. No.: 12/144,577

(22) Filed: Jun. 23, 2008

Related U.S. Application Data

(60) Provisional application No. 60/936,735, filed on Jun. 22, 2007.

(51) Int. Cl.
*C12Q 1/68* (2006.01)
(52) U.S. Cl. .......................................................... 435/6
(58) Field of Classification Search ........................ None
See application file for complete search history.

(56) References Cited

U.S. PATENT DOCUMENTS

| | | | |
|---|---|---|---|
| 3,346,381 A | 10/1967 | Grieg | |
| 5,439,797 A | 8/1995 | Tsien et al. | |
| 5,444,149 A | 8/1995 | Keene et al. | |
| 5,587,300 A | 12/1996 | Malter | |
| 5,698,427 A | 12/1997 | Keene et al. | |
| 5,700,660 A | 12/1997 | Leonard et al. | |
| 5,731,343 A | 3/1998 | Feng et al. | |
| 5,776,738 A | 7/1998 | Dell'Orco, Sr. et al. | |
| 5,843,770 A | 12/1998 | Ill et al. | |
| 5,849,520 A | 12/1998 | Leonard et al. | |
| 5,859,227 A | 1/1999 | Giordano et al. | |
| 5,908,779 A | 6/1999 | Carmichael et al. | |
| 5,928,888 A | 7/1999 | Whitney | |
| 5,990,298 A | 11/1999 | Carmichael et al. | |
| 6,004,749 A | 12/1999 | Giordano et al. | |
| 6,010,856 A | 1/2000 | Ulevitch et al. | |
| 6,057,437 A | 5/2000 | Kamiya et al. | |
| 6,107,029 A | 8/2000 | Giordano | |
| 6,159,709 A | 12/2000 | Korneluk et al. | |
| 6,171,821 B1 | 1/2001 | Korneluk et al. | |
| 6,203,982 B1 | 3/2001 | Nunokawa et al. | |
| 6,214,563 B1 | 4/2001 | Negulescu et al. | |
| 6,221,587 B1 | 4/2001 | Ecker et al. | |
| 6,221,612 B1 | 4/2001 | Knapp et al. | |
| 6,232,070 B1 | 5/2001 | Shuman | |
| 6,265,167 B1 | 7/2001 | Carmichael et al. | |
| 6,265,546 B1 | 7/2001 | Cohen et al. | |
| 6,284,882 B1 | 9/2001 | Wu-Wong et al. | |
| 6,303,295 B1 | 10/2001 | Taylor et al. | |
| 6,331,170 B1 | 12/2001 | Ordway | |
| 6,331,396 B1 | 12/2001 | Silverman et al. | |
| 6,399,373 B1 | 6/2002 | Bougueleret | |
| 6,448,007 B1 | 9/2002 | Giordano et al. | |
| 6,455,280 B1 | 9/2002 | Edwards et al. | |
| 6,465,176 B1 | 10/2002 | Giordano et al. | |
| 6,476,208 B1 | 11/2002 | Cohen et al. | |
| 6,528,060 B1 | 3/2003 | Nicolette | |
| 6,617,493 B1 | 9/2003 | Fader | |
| 6,627,797 B1 | 9/2003 | Duvick et al. | |
| 6,630,589 B1 | 10/2003 | Giordano et al. | |
| 6,635,671 B1 | 10/2003 | Kastelic et al. | |
| 6,638,522 B1 | 10/2003 | Mulye | |
| 6,645,747 B1 | 11/2003 | Hallahan et al. | |
| 6,653,132 B1 | 11/2003 | Keshet et al. | |
| 6,667,152 B2 | 12/2003 | Miles et al. | |
| 6,872,850 B2 | 3/2005 | Giordano et al. | |
| 7,078,171 B2 | 7/2006 | Giordano et al. | |
| 7,371,726 B2 | 5/2008 | Junker et al. | |
| 7,601,840 B2 | 10/2009 | Moon et al. | |
| 7,767,689 B2 | 8/2010 | Moon et al. | |
| 2002/0006661 A1 | 1/2002 | Green et al. | |
| 2002/0132257 A1 | 9/2002 | Giordano et al. | |
| 2003/0135870 A1 | 7/2003 | Cheikh et al. | |
| 2003/0199453 A1 | 10/2003 | Giordano et al. | |
| 2004/0063120 A1 | 4/2004 | Beer et al. | |
| 2004/0091866 A1 | 5/2004 | Giordano et al. | |
| 2004/0138282 A1 | 7/2004 | Greig et al. | |
| 2004/0152117 A1 | 8/2004 | Giordano et al. | |
| 2004/0214223 A1 | 10/2004 | Cao et al. | |
| 2004/0231007 A1 | 11/2004 | Kastelic et al. | |
| 2005/0048549 A1 | 3/2005 | Cao et al. | |
| 2007/0072186 A1 | 3/2007 | Mehta et al. | |
| 2007/0111203 A1 | 5/2007 | Cao et al. | |
| 2007/0254878 A1 | 11/2007 | Cao et al. | |
| 2008/0064683 A1 | 3/2008 | Cao et al. | |
| 2009/0068654 A1 | 3/2009 | Kastelic et al. | |

FOREIGN PATENT DOCUMENTS

| | | |
|---|---|---|
| EP | 1 179 196 | 1/2002 |
| EP | 1 604 011 | 12/2005 |
| EP | 1 761 638 | 3/2007 |
| GB | 9828707.1 | 12/1998 |
| GB | 9828709.7 | 12/1998 |
| WO | WO 95/33831 | 12/1995 |
| WO | WO 97/25860 | 7/1997 |
| WO | WO 98/39484 | 9/1998 |
| WO | WO 93/20212 | 10/1999 |
| WO | WO 00/04051 | 1/2000 |
| WO | WO 00/05356 | 2/2000 |
| WO | WO 00/39314 | 7/2000 |
| WO | WO 00/46247 | 8/2000 |
| WO | WO 01/84155 | 8/2001 |
| WO | WO 02/48150 | 6/2002 |

(Continued)

OTHER PUBLICATIONS

U.S. Appl. No. 12/143,705, filed Jun. 20, 2008, Friesen et al.
U.S. Appl. No. 12/143,697, filed Jun. 20, 2008, Friesen et al.
Response to Notice of Non-Compliant Amendment, filed Jul. 9, 2007, in U.S. Appl. No. 10/895,393.
Restriction Requirement, mailed Dec. 28, 2006, in U.S. Appl. No. 10/895,393.

(Continued)

*Primary Examiner* — Robert C Hayes
(74) *Attorney, Agent, or Firm* — Jones Day

(57) ABSTRACT

The present invention provides compounds and assays for the identification and validation of compounds for use in the treatment of spinal muscular atrophy (SMA), in which said compounds up-regulate the post-transcriptional expression of SMN1 or SMN2.

25 Claims, 11 Drawing Sheets

FOREIGN PATENT DOCUMENTS

| | | |
|---|---|---|
| WO | WO 02/077609 | 10/2002 |
| WO | WO 02/083953 | 10/2002 |
| WO | WO 03/087815 | 10/2003 |
| WO | WO 2004/065561 | 8/2004 |
| WO | WO 2005/049868 | 6/2005 |
| WO | WO 2005/095615 | 10/2005 |
| WO | WO 2005/118857 | 12/2005 |
| WO | WO 2006/022712 | 3/2006 |

OTHER PUBLICATIONS

Amendment, filed Apr. 3, 2008, in U.S. Appl. No. 10/895,393.
Response to Restriction Requirement, filed Apr. 25, 2007, in U.S. Appl. No. 10/895,393.
Office Action, mailed Oct. 4, 2007, in U.S. Appl. No. 10/895,393.
Final Office Action, mailed Dec. 16, 2008, in U.S. Appl. No. 10/895,393.
Request for Continued Examination and Amendment, dated Jun. 16, 2009, in U.S. Appl. No. 10/895,393.
Restriction Requirement mailed Sep. 3, 2009 in U.S. Appl. No. 10/895,393.
Response to Restriction/Election Requirement, dated Dec. 2, 2009 in U.S. Appl. No. 10/895,393.
Non-Final Rejection, dated Feb. 18, 2010 in U.S. Appl. No. 10/895,393.
Response to Non-Final Office Action, dated Aug. 17, 2010 in U.S. Appl. No. 10/895,393.
Restriction/Election Requirement, dated Jan. 26, 2009, in U.S. Appl. No. 10/579,500.
Response to Restriction/Election Requirement, dated Jun. 26, 2009, in U.S. Appl. No. 10/579,500.
Restriction/Election Requirement, dated Aug. 6, 2009, in U.S. Appl. No. 10/579,500.
Response to Restriction/Election Requirement, dated Sep. 4, 2009, in U.S. Appl. No. 10/579,500.
Non-Final Rejection, dated Jan. 5, 2010, in U.S. Appl. No. 10/579,500.
Requirement for Restriction/Election, dated Jan. 11, 2007, in U.S. Appl. No. 10/851,074.
Amendment and Response to Restriction/Election, dated May 11, 2007, in U.S. Appl. No 10/851,074.
Non Final Office Action, dated Sep. 7, 2007, in U.S. Appl. No. 10/851,074.
Amendment and Response to Non-Final Rejection, dated Mar. 4, 2008, in U.S. Appl. No. 10/851,074.
Non Final Rejection, dated Jul. 10, 2008, in U.S. Appl. No. 10/851,074.
Non Final Rejection, dated Oct. 23, 2008, in U.S. Appl. No. 10/851,074.
Amendment and Response to Non-Final Rejection, dated Apr. 22, 2009, in U.S. Appl. No. 10/851,074.
Final Rejection, dated Aug. 24, 2009, in U.S. Appl. No. 10/851,074.
Response to Final Rejection and Request for Continued Examination, dated Nov. 24, 2009, in U.S. Appl. No. 10/851,074.
Non-Final Rejection, dated Jun. 24, 2010, in U.S. Appl. No. 10/851,074.
Preliminary Amendment filed Oct. 23, 2006 in U.S. Appl. No. 10/543,033.
Restriction Requirement mailed May 16, 2008 in U.S. Appl. No. 10/543,033.
Response to Restriction Requirement and Preliminary Amendment filed Nov. 17, 2008 in U.S. Appl. No. 10/543,033.
Office Action mailed Feb. 20, 2009 in U.S. Appl. No. 10/543,033.
Response to Non-final rejection, dated Jul. 17, 2009, in U.S. Appl. No. 10/543,033.
Final Rejection, dated Jan. 13, 2010, in U.S. Appl. No. 10/543,033.
Response to Office Action, dated Jul. 13, 2010, in U.S. Appl. No. 10/543,033.
Supplemental Partial European Search Report, dated Jun. 13, 2008, issued in EP 04781055.1 (EP 1786933).
Supplemental European Search Report, dated Dec. 11, 2008, issued in EP 04809465.0 (EP1761638).
Supplemental Partial European Search Report, dated Nov. 5, 2009, issued in EP 04704085.2 (EP 1604011).
International Search Report dated Jul. 14, 2008 in the PCT Application No. PCT/US04/01643 filed Jan. 21, 2004.
Written Opinion of the International Searching Authority dated Jul. 14, 2008 in the PCT Application No. PCT/US04/01643 filed Jan. 21, 2004.
International Search Report, dated Jul. 13, 2005, in the PCT Application No. PCT/US04/26309.
International Preliminary Report on Patentability, dated Jan. 23, 2007, in the PCT Application No. PCT/US04/26309.
Written Opinion of the International Searching Authority, dated Jul. 13, 2005, in the PCT Application No. PCT/US04/26309.
International Preliminary Report on Patentability, dated Nov. 19, 2007, in the PCT Application No. PCT/US04/020751.
International Search Report, dated Nov. 6, 2007 in PCT/US04/20751.
Written Opinion of the International Searching Authority, dated Nov. 6, 2007, in the PCT Application No. PCT/US04/020751.
International Search Report, dated Feb. 16, 2005, in the PCT Application No. PCT/US04/038496.
Written Opinion, dated May 17, 2006, in the PCT Application No. PCT/US04/038496.
International Preliminary Report on Patentability, dated Jul. 31, 2008, in the PCT Application No. PCT/US04/038496.
Preliminary Amendment, dated Jul. 24, 2008 in U.S. Appl. No. 12/143,705.
Preliminary Amendment, dated Dec. 30, 2008 in U.S. Appl. No. 12/143,705.
Restriction Requirement, dated Sep. 15, 2010 in U.S. Appl. No. 12/143,705.
Preliminary Amendment, dated Jul. 24, 2008 in U.S. Appl. No. 12/143,697.
Preliminary Amendment, dated Dec. 30, 2008 in U.S. Appl. No. 12/143,697.
Restriction Requirement, dated Jul. 9, 2010 in U.S. Appl. No. 12/143,697.
Response to Restriction Requirement, dated Sep. 9, 2010 in U.S. Appl. No. 12/143,697.
Non-Final Rejection, dated Sep. 22, 2010 in U.S. Appl. No. 12/143,697.
Avila et al., 2007 "Trichostatin A increases SMN expression and survival in a mouse model of spinal muscular atrophy", J Clin Invest.; 117(3):659-71.
Bertini et al., 2005, "134th ENMC International Workshop: Outcome Measures and Treatment of Spinal Muscular Atrophy, Feb. 11-13, 2005, Naarden, The Netherlands", Neuromuscul Disord. 15(11):802-16.
Boda et al., 2004, "Survival motor neuron SMN1 and SMN2 gene promoters: identical sequences and differential expression in neurons and non-neuronal cells", Eur J Hum Genet.; 12(9):729-37.
Brahe et al., 2005, "Phenylbutyrate increases SMN gene expression in spinal muscular atrophy patients", Eur J Hum Genet.; 13(2):256-9.
Echaniz-Laguna et al., 1999, "The promoters of the survival motor neuron gene (SMN) and its copy (SMNc) share common regulatory elements", Am J Hum Genet; 64(5):1365-70.
Germain-Desprez et al., 2001, "The SMN genes are subject to transcriptional regulation during cellular differentiation", Gene, 279:109-117.
Iannaconne et al., 2002 "Outcome Measures for Pediatric Spinal Muscular Atrophy", Arch Neurol. 59:1445-1450.
Iannaconne et al., 2003, "Reliability of 4 Outcome Measures in Pediatric Spinal Muscular Atrophy", Arch Neurol; 60:1130-1136.
Jarecki et al., 2005 "Diverse small-molecule modulators of SMN expression found by high-throughput compound screening: early leads towards a therapeutic for spinal muscular atrophy", Hum Mol Genet.; 14(14):2003-18.
Kolb et al., 2006, "A novel cell immunoassay to measure survival of motor neurons protein in blood cells", BMC Neurology, 6:6.
Lunn et al., 2004, "Indoprofen upregulates the survival motor neuron protein through a cyclooxygenase-independent mechanism", Chem Biol.; 11(11):1489-93.

Merlini et al., 2003, "Role of gabapentin in spinal muscular atrophy: results of a multicenter, randomized Italian study", J Child Neurol.; 18(8):537-41.

Monani et al., 1999, Promoter analysis of the human centromeric and telomeric survival motor neuron genes (SMNC and SMNT), Biochim Biophys Acta; 1445(3):330-6.

Sumner., 2006, "Therapeutics development for spinal muscular atrophy", NeuroRx.; 3(2):235-45.

Wan, 2005, "The survival of motor neurons protein determines the capacity for snRNP assembly: biochemical deficiency in spinal muscular atrophy", Molec & Cell Biol, 25(13): 5543-5551.

Wolstencroft et al., 2005, "A non-sequence-specific requirement for SMN protein activity: the role of aminoglycosides in inducing elevated SMN protein levels", Hum Mol Genet, 14(9):1199-1210.

Zhang et al., 2001, "An in vivo reporter system for measuring increased inclusion of exon 7 in SMN2 mRNA: potential therapy of SMA", Gene Ther., (20):1532-1538.

Afounda et al., 1999, "Localized XId3 mRNA activation in *Xenopus* embryos by cytoplasmic polyadenylation." Mech Dev., 88(1):15-31.

Aharon & Schneider, 1993, "Selective destabilization of short-lived mRNAs with the granulocyte-macrophage colony-stimulating factor AU-rich 3' noncoding region is mediated by a cotranslational mechanism" Mol. Cell. Biol., 13: 1971-1980.

Akashi et al., 1994, "Number and Location of AUUUA Motifs: Role in Regulating Transiently Expressed RNAs." Blood, 83:3182-3187.

Akiri et al., 1998, Regulation of Vascular Endothelial Growth Factor (VEGF) Expression is Mediated by Internal Initiation of Translation and Alternative Initiation of Transcription. Oncogene, 17:227-236.

Amara et al., 1999, "TGF-beta(1), regulation of alzheimer amyloid precursor protein mRNA expression in a normal human astrocyte cell line: mRNA stabilization." Brain Res. Mol. Brain Res., 71(1):42-49.

Banholzer et al., 1997, "Rapamycin destabilizes interleukin-3 mRNA in autocrine tumor cells by a mechanism requiring an intact 3' untranslated region." Molecular and Cellular Biology, 17: 3254-3260.

Barkoff et al., 2000, "Translational control of cyclin B1 mRNA during meiotic maturation: coordinated repression and cytoplasmic polyadenylation", Dev Biol., 220(1):97-109.

Bashaw & Baker, 1995, "The ms1-2 dosage compensation gene of *Drosophila* encodes a putative DNA-binding protein whose expression is sex specifically regulated by Sex-lethal", Develop., 121(10):3245-3258.

Beelman & Parker, 1994, "Differential effects of translational inhibition in cis and in trans on the decay of the unstable yeast MFA2 mRNA", J. Biol. Chem, 269:9687-9692.

Benjamin et al., 1997, "Conditional switching of vascular endothelial growth factor (VEGF) expression in tumors: induction of endothelial cell shedding and regression of hemangioblastoma-like vessels by VEGF withdrawal" Proc. Natl. Acad Sci 94:8761-8766.

Bergsten & Gavis, 1999 , "Role for mRNA localization translational activation but not spatial restriction of nanos RNA", Develop., 126(4):659-669.

Beutler et al., 1988, "Assay of Ribonuclease that preferentially hydrolyses mRNAs Containing Cytokine-Derived UA-Rich Instability Sequences", Biochem. Biophys Res. Commun., 152:973-980.

Bhattacharyy A et al., 2007, "Mining the GEMS—a novel platform technology targeting post-transcriptional control mechanisms", Drug Discov Today, 12(13-14):553-60.

Bornes et al., 2004, "Control of the Vascular Endothelial growth factor internal ribosome entry site (IRES) Activity and translation initiation by Alternativey Spliced Coding sequences", J Biol. Chem., 279(18):18717-18726.

Brenchley, 1998, "Antagonising the expression of VEGF in pathological angiogenesis," Exp. Opin Ther. Patents 8(12): 1695-1706.

Brennan & Seitz, 2001, "HuR and mRNA stability." Cell. Mol. Life. Sci., 58:266-277.

Carballo et al., 1998, "Feedback inhibition of macrophage tumor necrosis factor-alpha production by tristetraprolin", Science, 281:1001-1005.

Castagnetti et al., 2000, "Control of oskar mRNA by Bruno in a novel cell-free system from *Drosophila* ovaries", Develop., 127(5):1063-1068.

Charlesworth et al., 2000, "The temporal control of Wee1 mRNA translation during *Xenopus* oocyte maturation is regulated by cytoplasmic polyadenylation elements within the 3'-untranslated region", Dev. Biol., 227(2): 706-719.

Chen et al., 1994, "Interplay two functionally and structurally distinct domains of the c-fos AU-rich element specifics its mRNA-destabilizing function", Mol. Cell. Biol. 14:416-426.

Chen et al., 1994, "Selective Degradation of Early-Response-Gene mRNAs: Functional Analyses of Sequence Features of the AU-rich elements", Mol. Cell. Biol., 14: 8471-8482.

Chen et al., 1995, "AU-rich elements: characterization and importance in mRNA degradation", Trends Biochem. Sci., 20:465-470.

Chen et al., 1995, "mRNA decay mediated by two distinct AU-rich elements from c-fos and granulocyte-macrophage colony-stimulating factor transcripts: different deadenylation kinetics and uncoupling from translation", Mol. Cell. Biol., 15:5777-5788.

Chen et al., 2001, "AU Binding Proteins Recruit the Exosome to Degrade ARE-Containing mRNAs", Cell, 107: 451-464.

Child et al., 1999, "Cell type-dependent and—independent control of *Her-2/neu* translation", Int Journal of Biochem & Cell Biol., 31:201-213.

Cho et al., 2002, "Emerging techniques for the discovery and validation of therapeutic targets for skeletal diseases" Expert Opin. Ther. Targets, 6(6):679-689.

Claffey et al., 1998, "Identification of a human VPF/VEGF 3' untranslated region mediating hypoxia-induced mRNA stability", Mol. Biol. of Cell., 9:469-481.

Clark et al., 2000, "Synthesis of the posterior determinant Nanos is spatially restricted by a novel cotranslational regulatory mechanism", Curr. Biol., 10(20):1311-1314.

Clark et al., 2002, "A common translational control mechanism functions in axial patterning and neuroendocrine signaling in *Drosophila*" Develop., 129(14): 3325-3334.

Cohen et al., 1996, "Interleukin 6 induces the expression of vascular endothelial growth factor", J. Biol Chem., 27(12):736-741.

Cohen et al., 1996, "CN1-1493 inhibits monocyte/macrophage tumor necrosis factor by suppression of translation efficiency", Proc. Natl. Acad. Sci. USA, 93:3967-3971.

Crawford et al., 1997, "The Role of 3' Poly (A) Tail Metabolism in Tumor Necrosis Factor-α Regulation," J Biol. Chem,. 272:1120-21127.

Crosio et al., 2000, "La protein has a positive effect on the translation of TOP mRNAs in vivo", Nucl. Acids. Res., 28(15):2927-34.

Crucs et al., 2000, "Overlapping but distinct RNA elements control repression and activation of nanos translation", Mol. Cell., 5(3):457-467.

Curatola et al., 1995, "Rapid degradation of AU-rich element (ARE) mRNAs is activated by ribosome transit and blocked by secondary structure at any position 5' to the ARE", Mol. Cell. Biol., 15;6331-6340.

Dahanukar & Wharton, 1996, "The Nanos gradient in *Drosophila* embryos is generated by translational regulation", Genes Dev., 20:2610-2620.

Danner et al., 1998, "Agonist regulation of human beta2-adrenergic receptor mRNA stability occurs via a specific AU-rich element", J. Biol. Chem., 273(6):3223-9.

Database WPI Week, 2002, "Screening drug improving insulin resistance without exacerbating diabetic retinopathy, by detecting expression of reporter gene fused to promoter region of human vascular endothelial growth factor gene in mammal cell", JP 2001 340080 A.

De Jong et al., 2002, "RNA and RNA-protein complexes as targets or therapeutic intervention", Curr. Topics Medicinal Chem., 2:289-302.

De Wet et al., 1987, "Firefly luciferase Gene: Structure and Expression Mammalian Cells", Mol Cell. Biol., 7(2):725-737.

Dominski & Marzluff, 1999, "Formation of the 3' end of histone mRNA", Gene, 2 9(1):1-14.

Dreyfuss et al., 2002 "Messenger-RNA-Binding Proteins and the Messages they Carry", Nature Rev Molec Cell Biol., 3:195-205.

Eibl et al., 1999, "In vivo analysis of plastid psbA, rbcL and rpl32 UTR elements by chloroplast transformation: tobacco plastid gene expression is controlled by modulation of transcript levels and translation efficiency", Plant J. 19:333-345.

Fan et al., 1998, "Overepxression of HuR, a nuclear-cytoplasic shuttling protein, increases in vivo stability of ARE-containing mRNAS", EMBO, J 17:3448-3460.
Forsythe et al., 1996, "Activation of Vascular Endothelial Growth Factor Gene Transcription by Hypoxia-Inducible Factor 1", Molec & Cell. Biol., 16(9):4604-4613.
Fortes et al., 2003, "Inhibiting expression of specific genes in mammalian cells with 5' end-mutated u I small nuclear RNAs targeted to terminal exons of pre-mRNA", Proc. Natl. Acad. Sci., 100(14):8264-8269.
Gan et al., 1998, "Functional characterization of the internal ribosome entry site of elF4G mRNA", J. Biol. Chem., 273:5006-5012.
Gavis et al., 1996, "A conserved 90 nucleotide element mediates translational repression of nanos RNA", Development, 122(9):2791-2800.
Ge et al., 2002, "Regulation of Promoter Activitiy APP Gene by Cytokines and Growth Factors", Ann N. Y. Acad Sci., 973:463-467.
Gebauer et al., 1998, "The *Drosophila* splicing regulator sex-lethal directly inhibits translation of male-specific-lethal 2 mRNA", RNA 4(2):142-150.
Genbank Accession No. AF022375, dated Oct. 7, 1998.
Genbank Accession No. AJ131730, dated Oct. 7, 2008.
Genbank Accession No. M11567, dated Oct. 30, 1994.
Genbank Accession No. M14745, dated Apr. 27, 1993.
Genbank Accession No. M14758, dated Dec. 3, 1999.
Genbank Accession No. M33680, dated Aug. 3, 1993.
Genbank Accession No. M54968, dated Oct. 17, 2008.
GenBank Accession No. M90100, dated Dec. 31, 1994.
Genbank Accession No. NM_000230, dated Apr. 19, 2009.
Genbank Accession No. NM_000134, dated Apr. 12, 2009.
Genbank Accession No. NM_000162, dated Apr. 9, 2009.
Genbank Accession No. NM_000208, dated Mar. 29, 2009.
Genbank Accession No. NM_000247, dated Apr. 12, 2009.
Genbank Accession No. NM_000321, dated Apr. 19, 2009.
GenBank Accession No. NM_000418, dated Apr. 12, 2009.
Genbank Accession No. NM_000527, dated Apr. 26, 2009.
GenBank Accession No. NM_000572, dated Apr. 19, 2009.
Genbank Accession No. NM_000589, dated Apr. 12, 2009.
Genbank Accession No. NM_000600, dated Apr. 19, 2009.
Genbank Accession No. NM_000665, dated Apr. 12, 2009.
Genbank Accession No. NM_000758, dated Apr. 19, 2009.
Genbank Accession No. NM_000784, dated Mar. 29, 2009.
Genbank Accession No. NM_000791, dated Mar. 29, 2009.
Genbank Accession No. NM_000794, dated Apr. 10, 2009.
Genbank Accession No. NM_000799, dated Apr. 5, 2009.
Genbank Accession No. NM_000875, dated Apr. 10, 2009.
Genbank Accession No. NM_000899 dated Mar. 29, 2009.
Genbank Accession No. NM_000948, dated Mar. 22, 2009.
Genbank Accession No. NM_001145, dated Apr. 5, 2009.
Genbank Accession No. NM_001168, dated Apr. 19, 2009.
Genbank Accession No. NM_001240, dated Feb. 24, 2009.
Genbank Accession No. NM_001565, dated Apr. 12, 2009.
Genbank Accession No. NM_001567, dated Mar. 22, 2009.
Genbank Accession No. NM_001725, dated Oct. 22, 2006.
Genbank Accession No. NM_001728. dated Apr. 5, 2009.
Genbank Accession No. NM_001917, dated Apr. 5, 2009.
Genbank Accession No. NM_002006, dated Mar. 15, 2009.
Genbank Accession No. NM_002087, dated Mar. 29, 2009.
Genbank Accession No. NM_002111, dated Apr. 19, 2009.
Genbank Accession No. NM_002151, dated Apr. 23, 2009.
Genbank Accession No. NM_002231, dated Mar. 15, 2009.
Genbank Accession No. NM_002392, dated Apr. 19, 2009.
Genbank Accession No. NM_002632, dated Apr. 19, 2009.
Genbank Accession No. NM_002774, dated Apr. 11, 2009.
Genbank Accession No. NM_002925, dated Aug. 20, 2006.
Genbank Accession No. NM_002963, dated Apr. 19, 2009.
Genbank Accession No. NM_002964, dated Mar. 29, 2009.
Genbank Accession No. NM_002986, dated Mar. 29, 2009.
Genbank Accession No. NM_003255, dated Mar. 22, 2009.
Genbank Accession No. NM_003256, dated Apr. 5, 2009.
Genbank Accession No. NM_003355, dated Apr. 19, 2009.
Genbank Accession No. NM_003642, dated Oct. 22, 2008.
Genbank Accession No. NM_003883, dated Apr. 12, 2009.
Genbank Accession No. NM_004364, dated Apr. 5, 2009.
Genbank Accession No. NM_004395, dated Dec. 21, 2008.
Genbank Accession No. NM_004795, dated Apr. 12, 2009.
Genbank Accession No. NM_004797, dated Apr. 12, 2009.
Genbank Accession No. NM_005251, dated Apr. 5, 2009.
Genbank Accession No. NM_005252, dated Apr. 5, 2009.
Genbank Accession No. NM_005417, dated Apr. 19, 2009.
Genbank Accession No. NM_005931, dated Apr. 5, 2009.
Genbank Accession No. NM_006536, dated Sep. 17, 2006.
Genbank Accession No. NM_007310, dated Apr. 12, 2009.
Genbank Accession No. NM_018727, dated Mar. 1, 2009.
Genbank Accession No. NM_020415, dated Mar. 29, 2009.
Genbank Accession No. NM_032611, dated Mar. 29, 2009.
Genbank Accession No. NM_053056, dated Apr. 19, 2009.
Genbank Accession No. NM_078467, dated Apr. 19, 2009.
Genbank Accession No. NM_080704, dated Mar. 1, 2009.
Genbank Accession No. NM_080705, dated Mar. 1, 2009.
Genbank Accession No. NM_080706, dated Mar. 1, 2009.
Genbank Accession No. NM_080881, dated Dec. 21, 2008.
Genbank Accession No. NM_138712, dated Apr. 12, 2009.
Genbank Accession No. NM_138992, dated Apr. 5, 2009.
Genbank Accession No. NM_139317, dated Apr. 5, 2009.
Genbank Accession No. S48568, dated Apr. 17, 2002.
Genbank Accession No. U22431, dated Jun. 28, 1995.
Genbank Accession No. U25676, dated Jul. 20, 1995.
Genbank Accession No. X005881, dated Oct. 7, 2008.
Genbank Accession No. X01394, dated Oct. 7, 2008.
Genbank Accession No. X16302, dated Apr. 18, 2005.
Genbank Accession No. XM_001831, dated May 8, 2002.
Genbank Accession No. XM_003061, dated May 8, 2002.
Genbank Accession No. XM_003751, dated Oct. 16, 2001.
Genbank Accession No. XM_015547, dated Aug. 1, 2002.
Genbank Accession No. XM_589987, dated Sep. 30, 2005.
Gil et al., 1996, "Multiple regions of the *Arabidopsis* Saur-AC1 gene control transcript abundance: the 3' untranslated region functions as an mRNA instability determinant", EMBO, J 15:1678-1686.
Goodwin et al., 1993, "Translational regulation of tra-2 by its 3' untranslated region controls sexual identity in *C. elegans*", Cell, 75:329-339.
Goodwin et al., 1997, "A genetic pathway for regulation of tra-2 translation", Develop., 124:749-758.
Grens et al., 1990, "The 5'—and 3'—untranslated regions of ornithine decarboxylase mRNA affect the translational efficiency", J. Biol. Chem., 265:11810-11816.
Guhaniyogi & Brewer, 2001, "Regulation of mRNA stability in mammalian cells", Gene, 265(1-2):11-23.
Haag & Kimble:, 2000, "Regulatory elements required for development of *Caenorhabditis elegans* hermaphrodites are conserved in the tra-2 homologue of *C. remanei*, a male/female sister species", Genetics, 155(1):105-116.
Heaton et al., 1998, "Cyclic Nucleotide Regulation of Type-1 Plasminogen Activator-Inhibitor mRNA stability in Rat Hepatoma Cells", J Biol. Chem., 273:14261-14268.
Hoover et al., 1997, "Pim-1 protein expression is regulated by its 5'—untranslated region and translation initiation actor e1F-4E", Cell Growth Differ., 8: 1371-1380.
Horvath et al., "Multiple elements in the 5' untranslated region downregulate c-sis messenger RNA translation", Cell Growth & Diff., 6: 1103-1110.
Huang et al., 1990, "Intervening sequences increase efficiency of RNA 3' processing and accumulation of cytoplasmic RNA", Nucl. Acids Res., 18(4):937-947.
Hubert et al., 1996, "RNAs mediating cotranslational insertion of selenocysteine in eukaryotic selenoproteins", Biochimie, 78(7):590-596.
Huez et al., 1998, "Two Independent Internal Ribosome Entry Sites are Involved in Translation Initiation of Vascular Endothelial Growth Factor mRNA", Mol. Cell. Biol., 18(11):6178-6190.
Hyder et al., 2000, "Identification of functional estrogen response elements in the gene coding for the potent angiogenic factor vascular endothelial growth factor", Cancer Res., 60:3183-3190.

Iida et al., 2002, "Vascular endothelial growth factor gene expression in a retinal pigmented cell is up-regulated by glucose deprivation through 3' UTR", Life Sciences, 71:1607-1614.

Ismail et al., 2000, "Split-intron retroviral vectors: enhanced expression with improved safety", J. Virol., 74 (5):2365-2371.

Jan et al., 1997, "Conservation of the C.elegans tra-2 3'UTR translational control", EMBO J., 16(20):6301-6313.

Jan et al., 1999, "The STAR protein, GLD-1, is a translational regulator of sexual identity in Caenorhabditis elegans ", EMBO J., 18:258-269.

Kakegawa et al., 2002, "Rapamycin induces binding activity to the terminal oligopyrimidine tract of ribosomal protein mRNA in rats", Arch Biochem Biophys., 402(1):77-83.

Kastelic et al., 1996, "Induction of rapid IL-1 beta mRNA degradation in THP-1 cells mediated through the AU-rich region in the 3'UTR by a radicicol analogue", Cytokine, 8: 751-761.

Kedersha et al., 2002, "Stress Granules: Sites of mRNA triage that Regulate mRNA Stability and Translatability", Biochem. Society Transactions, 30(6):963-969.

Keene & Tenenbaum, 2002, "Eukaryotic mRNPs may represent post-transcriptional operons" Mol. Cell., 9:1161-1167.

Kemeny et al., 1998, "The tetravalent guanylhydrazone CNI-1493 blocks the toxic effects of interleukin-2 without diminishing antitumor efficacy", Proc. Natl. Acad. Sci. USA, 95: 4561-4566.

Kim et al., 2002 "The human elongation factor 1 alpha (EF-1 alpha) first intron highly enhances expression of foreign genes from the murine cytomegalovirus promoter", J. Biotechnol., 93(2):183-187.

Klausner et al., 1993, "Regulating the Fate of mRNA: The control of Cellular Iron Metabolism ", Cell, 72:19-28.

Kobayashi et al., 1998, "Characterization of the 3' Untranslated region of mouse DNA topoisomerase IIα mRNA", Gene, 215:329-337.

Koeller et al., 1991, "Translation and the stability of mRNAs encoding the transferrin receptor and c-fos", Proc. Natl. Acad. Sci., 88:7778-7782.

Kowalski and Mager, 1998, "A human endogenous retrovirus suppresses translation of an associated fusion transcript, PLA2L", J. Virol., 72(7):6164-8.

Kozak et al., 1986, "Influences of mRNA secondary structure on initiation by eukaryotic ribosomes" Proc. Natl. Acad Sci., 83:2850-2854.

Lagnado et al., 1994, "AUUUA is Not sufficient to promote Poly(A) Shortening and Degradation of mRNA: the Functional Sequence within the AU-rich elements may be UUAUUUA(U/A) (U/A)", Mol. Cell. Biol., 14: 7984-7995.

Lai et al., 1999, "Evidence that Tristetraprolin binds to AU-Rich Elements and promotes the Deadenylation and Destabilitzation of Tumor Necrosis Factor Alpha mRNA", Mol. Cell. Biol., 19(6):4311-4323.

Lal et al., 2004, "Concurrent Versus Individual Binding of HuR and AUF1 to Common Labile Target mRNA's", EMBO J., 23:3092-3102.

Lemm et al., 2002, "Regulation of c-myc mRNA decay by translational pausing in a coding region instability determinant", Mol. Cell. Biol., 22(12):3959-3969.

Levy et al., 1995, "Sequence and functional characterization of the terminal exon of the human insulin receptor gene", Biochem Biophys Acta, 1263:253-257.

Levy et al., 1996, "Post-transcriptional Regulation of Vascular Endothelial Growth Factor by Hypoxia", J. Biol. Chem., 271:2746-2753.

Levy et al., 1998, "Hypoxic stabilization of vascular endothelial growth factor mRNA by the RNA-binding protein HuR", J Biol. Chem., 273(11):6417-6423.

Lewis et al., 1998, "Mapping of a Minimal AU-rich Sequence Required for Lipopolysaccharide-induce binding of a 55-kDA protein on tumor necrosis Factor-α mRNA", J Biol. Chem., 273:13781-13786.

Li et al., 2001, "Targeting HER-2/neu-overexpressing breast cancer cells by an antisense iron responsive element-directed gene expression", Cancer Letters, 174(2):151-58.

Mehta et al, 2006, "Derepression of the Her-2 uORF is mediated by a novel post-transcriptional control mechanism in cancer cells", Genes & Dev., 20:939-953.

Millard et al., 2000, "A U-Rich Element in the 5' Untranslated Region if necessary for the Translation of p27 mRNA" Molec & Cell. Biol., 20(16):5947-5959.

Miller et al., 1998, "The Vascular Endothelial Growth Factor mRNA Contains an Internal Ribosome Entry Site", FEBS Letters, 434:417-420.

Morris et al., 2000, "Upstream Open Reading Frames as Regulators of mRNA translation," Molec & Cell. Biol.,20(23):8635-8642.

Muhlrad et al., 1995, "Turnover mechanisms of the stable yeast PGK1 mRNA", Mol. Cell. Biol., 15(4):2145-2156.

Mukherjee et al., 2002, "The mammalian exosome mediates the efficient degradation of mRNAs that contain AU-rich elements", EMBO J., 21:165-174.

Nanbru et al., 1995, "Alternative translation of the proto-oncogene c-myc by an internal ribosome entry site", J. Biol. Chem., 272:32061-32066.

Nanbu et al., 1994, "Multiple Instability-Regulating Sites in the 3' Untranslated Region of the Urokinase-Type Plasminogen activator mRNA", Mol. Cell. Biol., 14:4920-4928.

NISHIMOR1 et al., 2004, "Involvement of the 3'-untranslated region of cyclooxygenase-2 gene in its post-transcriptional regulation through the glucocorticoid receptor", Life Sciences, 74:2505-2513.

Oh et al., 1992, "Homeotic gene Antennapedia mRNA contains 5'-noncoding sequences that confer translational initiation by internal ribosome binding", Genes Dev., 6:1643-1653.

Ostareck-Lederer et al., 2002, "c-Src-mediated phosphorylation of hnRNP K drives translational activation of specifically silenced mRNAs", Mol. Cell. Biol., 22(13):4535-4543.

Paynton & Bachvarova, 1994, "Polyadenylation and deadenylation of maternal mRNAs during oocyte growth and maturation in the mouse", Mol. Reprod. Dev., 37(2): 172-180.

Pelletier & Soneberg, 1988, "Internal initiation of translation of eukaryotic mRNA directed by a sequence derived from poliovirus RNA", Nature, 334:320-325.

Pesole et al., 2001, "Structural and Functional Features of Eukaryotic mRNA Untranslated Regions", Gene, 276:73-81.

Peterlin et al., 1993, "Tat Trans-Activator." In Human Retroviruses; Cullen Ed.; Oxford University Press: New York, pp. 75-100.

Piecyk et al., 2000, "TIA-1 is a translational silencer that selectively regulates the expression of TNF-alpha" EMBO J., 19:4154-4163.

Pontrelli et al., 2004, "Translational control of apolipoprotein B mRNA: regulation via cis elements in the 5' and 3' untranslated regions", Biochemistry, 43(21):6734-44.

Qin & Pyle, 1999, "Site-specific labeling of RNA with fluorophores and other structural probes", Methods, 18 (1):60-70.

Rajagopalan & Malter, 2000, "Growth factor-mediated stabilization of amyloid precursor protein mRNA is mediated by a conserved 29-nucleotide sequence in the 3'-untranslated region." J. Neurochem., 74(1):52-59.

Rapella et al., 2002, "Flavopiridol inhibits vascular endothelial growth factor production induced by hypoxia or picolinic acid in human neuroblastoma", Int. J. Cancer, 99:658-664.

Raught et al., 2000, "Regulation of ribosomal recruitment in eukaryotes" in: "Translational Control of Gene Expression", Sonenberg, Hershey and Mathews, eds. Cold Spring Harbor Laboratory Press, Ch. 6. pp. 245-293.

Reinmann et al., 2002, "Suppression of 15-lipoxygenase synthesis by hnRNP E1 is dependent on repetitive nature of LOX mRNA 3'-UTR control element DICE", J. Mol. Biol., 315(5):965-974.

Rogers et al., 2002, "An iron-responsive element type II in the 5'-untranslated region of the Alzheimer's amyloid precursor protein transcript", J. Biol. Chem., 277(47):45518-45528.

Sachs & Geballe, 2006, "Downstream control of upstream open reading frames", Genes & Dev., 20:915-921.

Sachs et al., 1993, "Messenger RNA Degradation in Eukaryotes", Cell, 74:413-421.

Sambrook et al., 1989, "Standard protocol for calcium phosphate-mediated transfection of adherent cells." Molec. Cloning, 16:33-37.

Savant-Bhonsale et al., 1992, "Evidence for instability of mRNAs containing AUUUA motifs mediated through translation-dependent assembly of a > 20S degradation complex", Genes Dev., 6:1927-1939.

Schlatter & Fussenegger, 2003, "Novel CNBP- and La-based translation control systems for mammalian cells." Biotechnol Bioeng., 81(1):1-12.

Shaw & Kamen, 1986, "A conserved AU sequence from the 3' Untranslated Region of GM-CSF mRNA mediates selective mRNA degradation", Cell, 46:659-667.

Shyu et al., 1991, "Two distinct destabilizing elements in the c-fos message trigger deadenylation as a first step in rapid mRNA decay", Genes Dev., 5:221-231.

Stebbins-Boaz et al., 1996, "CPEB controls the cytoplasmic polyadenylation of cyclin, Cdk2 and c-mos mRNAs and is necessary for oocyte maturation in *Xenopus*", EMBO J., 15(10):2582-2592.

Stein et al., 1998, "Translation of vascular endothelial growth factor mRNA by internal ribosome entry: implications for translation under hypoxia", Mol. Cell. Biol., 18:3112-3119.

Stoecklin et al., 1994, "Functional Hierarchy of AUUUA Motifs in Mediating Rapid Interleukin-3 mRNA decay", J Biol. Chem., 269:28591-28597.

Stoecklin et al., 2003, "A constitutitive Decay Element Promotes Tumor Necrosis Factor Alpha mRNA Degradation via an AU-Rich Element-Independent Pathway." Molec & Cell. Biol., 23(10):3506-3515.

Stolle et al., 1988, "Cellular Factor affecting the stability of β-globin mRNA." Gene, 62:65-74.

Stoneley, 1998, "C-Myc 5' untranslated region contains an internal ribosome entry segment", Oncogene, 16:423-428.

Sullivan et al., 1996, "Mutational analysis of the DST element in tobacco cells and transgenic plants: Identification of residues critical for mRNA instability", RNA, 2:308-315.

Tay et al., 2000, "The control of cyclin B1 mRNA translation during mouse oocyte maturation", Dev. Biol., 221(1):1-9.

Thiele et al., 1999, "Expression of leukocyte-type 12-lipoxygenase and reticulocyte-type 15-lipoxygenase in rabbits", Adv Exp Med Biol., 447:45-61.

Tholanikunnel & Malbon, 1997, "A 20-nucleotide (A + U)-rich element of beta2-adrenergic receptor (beta2AR) mRNA mediates binding to beta2AR-binding protein and is obligate for agonist-induced destabilization of receptor mRNA", J. Biol. Chem., 272:11471-11478.

Thompson et al., 2000, "Rapid deadenylation and Poly(A)-dependent translational repression mediated by the *Caenorhabditis elegans* tra-2 3' untranslated region in *Xenopus* embryos", Mol. Cell. Biol., 20(6):2129-2137.

Tischer et al., 1991, "The human gene for vascular endothelial growth factor", J. Biol. Chem., 266(18):11947-11954.

Trifillis et al., 1999, "Finding the right RNA: identification of cellular mRNA substrates for RNA-binding proteins", RNA, 5:1071-1082.

Trotta et al., 2003, "BCR/ABL activates mdm2 mRNA translation via the La antigen", Cancer Cell, 3(2):145-60.

Vagner et al., 1995, "Alternative translation of human fibroblast growth factor 2 mRNA occurs by internal entry of ribosomes", Mol. Cell. Biol., 15:35-44.

Vagner et al., 2001, "Irresistible IRES. Attracting the translation machinery to internal ribosome entry sites", EMBO Reports, 2:893-898.

Wang, et al., 2003, "Human SP-A 3'-UTR variants mediate differential gene expression in basal levels and in response to dexamethasone." Am J Physio, Lung Cell & Mol. Physio., 284(5):L738-L748.

Wells et al., 1998, "Circularization of mRNA by eukaryotic translation initiation factors." Mol. Cell., 2:135-140.

Westmark & Malter, 2001, "Extracellular-regulated kinase controls beta-amyloid precursor protein mRNA decay", Mol. Brain. Res., 90(2):193-201.

Wiklund et al., 2002, "Inhibition of translation by UAUUUAU and UAUUUUUAU motifs of the AU-rich RNA instability element in the HPV-1 late 3' untranslated region", J. Biol. Chem., 277:40462-40471.

Winstall et al., 1995, "Rapid mRNA Degradation Mediated by the c-fos 3' AU-Rich element and that mediated by the Granulocyte-Macrophage Colony-Stimulating Factor 4' AU-Rich Element occur through similar Polysome-Associated Mechanisms", Mol. Cell. Biol., 15:3796-3804.

Worthington et al., 2002, "RNA binding properties of the AU-rich element-binding recombinant Nup475/TIS11/tristetraprolin protein", J. Biol. Chem,, 277: 48558-48564.

Xu et al., 1997, "Modulation of the Fate of Cytoplasmic mRNA by AU-Rich elements: Key Sequence Features Controlling mRNA Deadenylation and Decay ", Mol. Cell. Biol., 17:4611-4621.

Yamazaki et al., 2003, "HIF-1-dependent VEGF reporter gene assay by a stable transformant of CHO cells", Biol & Pharm Bull., 26(4): 417-420.

Ye et al., 1997, "Ultrabithorax and Antennapedia 5' untranslated regions promote developmentally regulated internal translation initiation", Mol. Cell. Biol., 17:1714-1721.

Zaldi & Malter, 1995, "Nucleolin and heterogeneous nuclear ribonucleoprotein C proteins specifically interact with the 3'-untranslated region of amyloid protein precursor mRNA", J. Biol. Chem., 271(29):17292-17298.

Zhang et al., 1995, "Identification and Characterization of a Sequence motif involved in nonsense-mediated mRNA decay", Mol. Cell. Biol., 15:2231-2244.

Zhang et al., 1996, "An enhanced green fluorescent protein allows sensitive detection of gene transfer in mammalian cells", BBRC, 227:707-11.

Zhang et al., 2000, "Wild-type p53 suppresses angiogenesis in human leiomyosarcoma and synovial sarcoma by transcriptional suppression of vascular endothelial growth factor expression", Cancer Res., 60:3655-3661.

Zhu et al., 2001, "Binding of the La autoantigen to the 5' untranslated region of a chimeric human translation elongation factor 1A reporter mRNA inhibits translation in vitro", Biochim. Biophys Acta, 1521(1-3):19-29.

Zubiaga et al., 1995, "The nonamer UUAUUUAUU is the key AU-rich sequence motif that mediates mRNA degradation", Mol. Cell. Biol., 15(4):2219-30.

Gubitz et al., 2004 "The SMN complex", Exp Cell Res.; 296:51-6.

Paushkin et al.., 2002 "The SMN complex, an assemblyosome of ribonucleoproteins" Curr Opin Cell Biol., 14:305-12.

Sumner et al., 2006, "SMN mRNA and protein levels in peripheral blood: biomarkers for SMA clinical trials", Neurology, 66:1067-1073.

Yong et al., 2004, "Why do cells need an assembly machine for RNA-protein complexes?" Trends Cell Biol.; 15(5):226-32.

Adams et al., 1998, "Localized infusion of IGF-I results in skeleta muscle hypertrophy in rats." J Appl Physiol, 84:1716-1722.

Barton et al., 2002, "Muscle-specific expression of insulin-like growth factor I counters muscle decline in mdx mice", J. Cell Biol., 157:137-148.

Barton-Davis, 1998, "Viral mediated expression of insulin-like growth factor I blocks the aging-related loss of skeletal muscle function", PNAS, 95:15603-15607.

Bogdanovich et al., 2004, "Therapeutics for Duchenne muscular dystrophy: current approaches and future directions", J Mol Med., 82(21:102-15.

Burkin and Kaufman, 1999, "The α7β1 integrin in muscle development and disease", Cell Tissue Res., 296:183-190.

Chakkalakal et al., 2005, "Molecular, cellular, and pharmacological therapies Duchenne/Becker muscular dystrophies", FASEB J., 19(8):880-91.

Coleman et al., 1995, "Myogenic Vector Expression of Insulin-like Growth Factor I Stimulates Muscle Cell Differentiation and Myofiber Hypertrophy in Transgenie Mice", J. Biol. Chem., 270:12109-12116.

Davies and Nowak, 2006, "Molecular Mechanisms of Muscular Dystrophies: Old and New Players", Nature, 7:762-773 (Supplementary Information Included).

Engvall et al., 2003, "The new frontier in muscular dystrophy research: booster genes", FASEB J., 17: 1579-1584.

Gramolini et al., 2001, "Distinct regions in the 3' untranslated region are responsible for targeting and stabilizing utrophin transcripts in skeletal muscle cells", J Cell Biol. 1541:1173-1183.

Gramolini, 2001, "Increased expression of utrophin in a slow vs. a fast muscle involves posttranscriptional events", Am J Physiol Cell Physiol., 281(4):C1300-9.

Kambadur et al., 1997, "Mutations in myostatin (GDF8) in double-muscled Belgian Blue and Piedmontese cattle", Genome Res., 7(9):910-6.

Karin et al., 2006, "Role for IKK2 in muscle: waste not, want not", J Clin Invest., 116: 2866-2868.

Krag et al., 2004, "Heregulin ameliorates the dystrophic phenotype in *mdx* mice", PNAS, 101: 13856-13860.

Nowak and Davies, 2004, "Duchenne Muscular Dystrophy and dystrophin: pathogenesis and opportunities for treatment", EMBO Reports, 5:872-876.

Ohlendieck and Campbell, 1991, "Dystrophin-associated proteins are greatly reduced in skeletal muscle from mdx mice", J Cell Biol, 115:1685-1694.

Patel et al, 2005, "Molecular mechanisms involving IGF-1 and myostatin to induce muscle hypertrophy as a therapeutic strategy for Duchenne Muscular Dystrophy", Acta Myol., 24(3):230-41.

Tobin et al., 2005, "Myostatin, a negative regulator of muscle mass: implications for muscle degenerative diseases", Curr Opin Pharmacol., 5(3):328-32.

Vachon et al., 1997, "Integrins (alpha7beta1) in muscle function and survival. Disrupted expression in merosin-deficient congenital muscular dystrophy", J Clin Invest., 100(7):1870-81.

Veyrune et al., 1996, "A localisation signal in the 3' untranslated region of c-myc mRNA targets c-myc mRNA and beta-globin reporter sequences to the perinuclear cytoplasm and cytoskeletal-bound polysomes", J Cell Sci, 109:1185-1194.

Non-Final Rejection, dated Feb. 4, 2011 in U.S. Appl. No. 10/543,033.

Non-Final Rejection, dated Feb. 15, 2011 in U.S. Appl. No. 10/895,393.

Non-Final Rejection, dated Jan. 1, 2011 in U.S. Appl. No. 10/851,074.

Response to Office Action, dated Jun. 27, 2011 in U.S. Appl. No. 10/851,074.

Response to Restriction Requirement, dated Oct. 5, 2010 in U.S. Appl. No. 12/143,705.

Non-Final Rejection, dated Feb. 2, 2011 in U.S. Appl. No. 12/143,705.

Hudziak et al., 2000, "Antiproliferative effects of steric blocking phosphordiamidate morpholino antisense agents directed against c-myc." Antisense & Nucleic Acid Drug Development 10(3):163-176.

McTiernan et al., 1999, "Characterization of proximal transcription regulatory elements in the rat phospholamban promoter." J. Molecular & Cellular Cardiology. 31(12): 2137-2153.

Zwicky et al., 2003, "Exploring the Role of 5' Alternative Splicing and of the 3'-Untranslated region of Cathepsin B MRNA" Biological Chemistry 384(7): 1007-1018.

European Search Report, dated Nov. 17, 2011 issued in EP 2 400 038.

European Search Report, dated May 18, 2011 issued in EP Application No. 10189802.1.

Amendment, dated Aug. 2, 2011 in U.S. Appl. No. 12/143,705.

Final Rejection, dated Nov. 28, 2011 in U.S. Appl. No. 12/143,705.

Amendment, dated Aug. 4, 2011 in U.S. Appl. No. 10/543,033.

Final Rejection, dated Oct. 13, 2011 in U.S. Appl. No. 10/895,393.

Project Catalyst Poster—"Identification and characterization of small molecules for the treatment of duchenne muscular dystrophy," previously presented at the Muscular Dystrophy Coordinating Committee on Jun. 25, 2007 in Washington, D.C.

Abstract of Project Catalyst Poster—"Identification and characterization of small molecules for the treatment of duchenne muscular dystrophy," previously presented at the Muscular Dystrophy Coordinating Committee on Jun. 25, 2007 in Washington, D.C.

PTC Therapeutics Poster—"Identification and characterization of small molecules for the treatment of duchenne muscular dystrophy," previously presented at the 11th Annual Meeting of the RNA Society on Jun. 20, 2006 in Seattle, Washington.

SMN 5' Untranslated Region

- 5'UTR: 163 nt

- CCACAAATGTGGGAGGGCGATAACCACTCGTAGAAAGCGTGAGAAGTT
    ACTACAAGCGGTCCTCCCGGCCACCGTACTGTTCCGCTCCCAGAAGCC
    CCGGGCGGCGGAAGTCGTCACTCTTAAGAAGGGACGGGGCCCCACGC
    TGCGCACCCGCGGGTTTGCT

- uORF: ATGTGGGAGGGCGATAACCACTCGTAG (9 amino acids)
    - GC rich: 63%

FIG. 1

SMN1 3' Untranslated Region

- 3'UTR: 577 nt

- GGAGAAATGCTGGCATAGAGCAGCACTAAATGACACCACTAAAGAAACG
    ATCAGACAGATCTGGAATGTGAAGCGTTATAGAAGATAACTGG<u>CCTCATT
    TCTTC</u>AAAATATCAAGTGTTGGGAAAGAAAAAAGGAAGTGGAATGGGTAA
    <u>CTCTTCTT</u>GATTAAAAGTTATGTAATAACCAAATGCAATGTGAAATATTTT
    ACTGGACTCTATTTTTGAAAAACCATCTGTAAAAGACT<u>GAGGTGGGGGTG
    GGAGGCCAGCACGGTGGTGAGGCAG</u>TTGAGAAAATTTGAATGTGGATTA
    GATTTTGAATGATATTGGATAATTATTGGTAATTTTATGAGCTGTGAGAAG
    GGTGTTGTAGTTTATAAAAGACTGTCTTAATTTGCATACTTAAGCATTTAG
    GAATGAAGTGTTAGAGTGTCTTAAAATGTTTCAAATGGTTTAACAAAATGT
    ATGTGAGGCGTATGTGGCAAAATGTTACAGAATCTAACTGGTGGACATG
    GCTGTTCATTGTACTGTTTTTTTCTATCTTCTATATGTTTAAAAGTATATAA
    TAAAAATATTTAATTTTTTTTTAAA

> ARE: 4 (Bold)
    > CU-rich: 2 (Underlined)
    > 1 GC-rich region (Double-Underlined)

FIG. 2

SMN2 3' Untranslated Region

- 3'UTR: 559 nt

- AGCAGCACTAAATGACACCACTAAAGAAACGATCAGACAGATCTGGAAT
  GTGAAGCGTTATAGAAGATAACTGG<u>CCTCATTTCTTC</u>AAAATATCAAGTG
  TTGGGAAAGAAAAAAGGAAGTGGAATGGGTAA<u>CTCTTCTT</u>GATTAAAAGT
  TATGTAATAACCAAATGCAATGTGAAAATTTTACTGGACTCTATTTTGAA
  AAACCATCTGTAAAAGACT<u><u>GAGGTGGGGGTGGGAGGCCAGCACGGTGG</u></u>
  <u><u>TGAGGCAG</u></u>TTGAGAAAATTTGAATGTGGATTAGATTTTGAATGATATTGG
  ATAATTATTGGTAATTTTATGAGCTGTGAGAAGGGTGTTGTAGTTTATAAA
  AGACTGTCTTAATTTGCATACTTAAGCATTTAGGAATGAAGTGTTAGAGT
  GTCTTAAAATGTTTCAAATGGTTTAACAAAATGTATGTGAGGCGTATGTG
  GCAAAATGTTACAGAATCTAACTGGTGGACATGGCTGTTCATTGTACTGT
  TTTTTTCTATCTTCTATATGTTTAAAAGTATATAATAAAAATATTTAATTTTT
  TTTTAAA

➢ ARE: 4 (Bold)
  ➢ CU-rich: 2 (Underlined)
  ➢ 1 GC-rich region (Double-Underlined)

FIG. 3

METHODS OF SCREENING FOR COMPOUNDS FOR TREATING SPINAL MUSCULAR ATROPHY USING SMN MRNA TRANSLATION REGULATION

This application claims the benefit under 35 U.S.C. §119(e) of U.S. Provisional Application No. 60/936,735, filed Jun. 22, 2007.

FIELD OF THE INVENTION

The present invention relates to assays for screening compounds useful for treating spinal muscular atrophy and methods for treating this devastating neurological disease.

BACKGROUND OF THE INVENTION

Spinal Muscular Atrophy (SMA), in its broadest sense, describes a collection of inherited and acquired central nervous system (CNS) diseases characterized by motor neuron loss in the spinal cord and brainstem causing muscle weakness and atrophy. The most common form of SMA is caused by mutation of the Survival Motor Neuron (SMN) gene, and manifests over a wide range of severity affecting infants through adults.

Infantile SMA is one of the most severe forms of this neurodegenerative disorder. The onset is usually sudden and dramatic. Some of the symptoms include: muscle weakness, poor muscle tone, weak cry, limpness or a tendency to flop, difficulty sucking or swallowing, accumulation of secretions in the lungs or throat, feeding difficulties and increased susceptibility to respiratory tract infections. The legs tend to be weaker than the arms and developmental milestones, such as lifting the head or sitting up, cannot be reached. In general, the earlier the symptoms appear, the shorter the lifespan. Shortly after symptoms appear, the motor neuron cells quickly deteriorate. The disease can be fatal and has no known cure. The course of SMA is directly related to the severity of weakness. Infants with a severe form of SMA frequently succumb to respiratory disease due to weakness in the muscles that support breathing. Children with milder forms of SMA live much longer, although they may need extensive medical support, especially those at the more severe end of the spectrum. Disease progression and life expectancy strongly correlate with the subject's age at onset and the level of weakness. The clinical spectrum of SMA disorders has been divided into the following five groups:

(a) In Utero SMA (Type 0 SMA; before birth): Type 0, also known as very severe SMA, is the most severe form of SMA and begins before birth. Usually, the first symptom of type 0 is reduced movement of the fetus that is first seen between 30 and 36 weeks of the pregnancy. After birth, these newborns have little movement and have difficulties with swallowing and breathing.

(b) Infantile SMA (Type 1 SMA or Werdnig-Hoffmann disease; generally 0-6 months): Type 1 SMA, also known as severe infantile SMA or Werdnig Hoffmann disease, is the very severe, and manifests at birth or within 6 months of life. Patients never achieve the ability to sit, and death usually occurs within the first 2 years without ventilatory support.

(c) Intermediate SMA (Type 2 SMA; generally 7-18 months): Patients with Type 2 SMA, or intermediate SMA, achieve the ability to sit unsupported, but never stand or walk unaided. The onset of weakness is usually recognized some time between 6 and 18 months. Prognosis in this group is largely dependent on the degree of respiratory involvement.

(d) Juvenile SMA (Type 3 or Kugelberg-Welander disease; generally >18 months): Type 3 SMA describes those who are able to walk independently at some point during their disease course, but often become wheelchair bound during youth or adulthood.

(e) Adult SMA (Type 4 SMA): Weakness usually begins in late adolescence in tongue, hands, or feet then progresses to other areas of the body. The course of adult disease is much slower and has little or no impact on life expectancy.

The SMA disease gene has been mapped by linkage analysis to a complex region of chromosome 5q. In humans, this region has a large inverted duplication; consequently, there are two copies of the SMN gene. SMA is caused by a mutation or deletion of the telomeric copy of the gene (SMN1) in both chromosomes, resulting in the loss of SMN1 gene function. However, all patients retain a centromeric copy of the gene (SMN2), and its copy number in SMA patients has been implicated as having an important modifying effect on disease severity. i.e., an increased copy number of SMN2 is observed in less severe disease. Nevertheless, SMN2 is unable to compensate completely for the loss of SMN1 function, because the SMN2 gene produces reduced amounts of full-length RNA and is less efficient at making protein; though it does so in low amounts. More particularly, the SMN1 and SMN2 genes differ by five nucleotides; one of these differences, a translationally silent C to T substitution in an exonic splicing region, results in frequent exon 7 skipping during transcription of SMN2 mRNA. As a result, the majority of transcripts produced from SMN2 lack exon 7, SMN-ΔEx7, and encode a truncated protein that has an impaired function and is rapidly degraded. The SMN protein is thought to playa role in RNA processing and metabolism. Its best characterized function is regulating the assembly of a specific class of RNA-protein complexes called snRNPs. SMN may have other functions in motor neurons, however its role in preventing the selective degeneration of motor neurons is not known.

In most cases, a diagnosis of SMA can be made on the basis of clinical symptoms and by the SMN gene test, which determines whether there is at least one copy of the SMN1 gene by detecting its unique sequences (that distinguish it from the almost identical SMN2) in exons 7 and 8. However, other forms of spinal muscular atrophy are caused by mutation of other genes, some known and others not defined. In some cases, when the SMN gene test is not possible, or does not show any abnormality, other tests such as an electromyography (EMG) or muscle biopsy may be indicated.

Medical care for SMA patients is supportive, including, respiratory, nutritional and rehabilitation care; there is no drug known to otherwise alter the course of the disease. Current treatment for SMA consists of prevention and management of the secondary effect of chronic motor unit loss. The major management issue in Type 1 SMA is the prevention and early treatment of respiratory infections, pneumonia is the cause of death in the majority of the cases. While some infants afflicted with SMA grow to be adults, those with Type 1 SMA have a life expectancy of less than two years.

As a result of the progress made in understanding the genetic basis and pathophysiology of SMA, several strategies for treatment have been explored, but none have yet demonstrated success. For example, gene replacement (of SMN1) and cell replacement (using differentiated ES cells) strategies are being tested in animals. However, these approaches to treat SMA will require many more years of investigation before they can be applied to humans. Other approaches under exploration include searching for drugs that increase SMN levels, enhance residual SMN function, or compensate for its loss.

Drugs such as indoprofen or aminoglycosides, which enhance expression of the SMN protein from SMN2 mRNA by promoting translational read-through of a stop codon, have been assessed in cell culture, but have poor central nervous system penetration. Chemotherapeutic agents, such as aclarubicin, have been shown to increase SMN protein in cell culture; however, the toxicity profile of these drugs prohibits long-term use in SMA patients. Some drugs under clinical investigation for the treatment of SMA include transcription activators, such as histone deacetylase ("HDAC") inhibitors (e.g., butyrates, valproic acid, and hydroxyurea), the goal being to increase transcription of the SMN2 gene. However, the use of the HDAC inhibitors results in a global (nonspecific) increase in transcription and gene expression. In an alternative approach, the use of neuroprotectants that have demonstrated modest efficacy in other neurodegenerative conditions (e.g., riluzole, which is used in patients with ALS) have been chosen for investigation. Such strategies are not aimed at SMN for the treatment of SMA, but instead, are being explored to protect the SMN-deficient motor neurons from neurodegeneration.

Despite the progress made in understanding the genetic basis and pathophysiology of SMA, no therapy exists to alter the course of SMA, one of the most devastating childhood neurological diseases.

SUMMARY OF THE INVENTION

The present invention relates to methods for treating SMA. The present invention relates to methods for treating SMA using a compound to modulate any of the 5'-UTR (untranslated region) and 3'-UTR, the 5'-UTR or the 3'-UTR of SMN mRNA transcripts (i.e., SMN1 or SMN2) to increase expression of SMN or SMNΔEx7 protein. Compounds that target any of the 5'-UTR and 3'-UTR, the 5'-UTR or the 3'-UTR of SMN and post-transcriptionally up-regulate, increase, enhance, or upregulate expression of SMN or SMNΔEx7 protein can be used to treat SMA in human subjects in need thereof.

SMA is caused by deletion or mutation of the SMN1 gene, resulting in selective degeneration of SMN-deficient motor neurons. Although human subjects retain a copy of SMN2, its predominant gene product, SMNΔEx7, and the small amount of SMN protein expressed does not fully compensate for the loss of SMN1. The method of the present invention is directed to using compounds to post-transcriptionally modulate any of the 5'-UTR and 3'-UTR, the 5'-UTR or the 3'-UTR of SMN mRNA and increase expression of SMN or SMNΔEx7 protein. Such compounds can be used to treat SMA in a human subject in need thereof.

The invention also relates to screening assays for the identification or validation of compounds that target any of the 5'-UTR and 3'-UTR, the 5'-UTR or the 3'-UTR of SMN. In particular, these assays involve the use of a nucleic acid construct comprising a reporter gene operably linked to any of the 5'-UTR and 3'-UTR, the 5'-UTR or the 3'-UTR of SMN1 or SMN2. Transcription of the reporter gene can be driven by any promoter, and need not be limited to a SMN promoter. Indeed, strong promoters, such as the CMV promoter may be used in screening assays. Accordingly, the nucleic acid construct optionally comprises one or more operably linked promoters operably linked to the reporter gene. Included within the scope of the present invention are those compounds that specifically modulate any of the 5'-UTR and 3'-UTR, the 5'-UTR or the 3'-UTR of the SMN1 or SMN2 to up-regulate post-transcriptional expression of a SMN1 or SMN2 gene or reporter gene.

The present invention provides for a nucleic acid construct comprising a reporter gene operably linked to (i) the 5'-UTR (untranslated region) of SMN or a fragment, mutant or post-transcriptional regulatory element thereof and the 3'-UTR of SMN or a fragment, mutant or post-transcriptional regulatory element thereof, (ii) the 5'-UTR of SMN or a fragment, mutant or post-transcriptional regulatory element thereof; or (iii) the 3'-UTR of SMN or a fragment, mutant or post-transcriptional regulatory element thereof, wherein the 5' UTR is upstream of the reporter gene and the 3' UTR is downstream of the reporter gene. In one embodiment, the 5'-UTR and/or 3'-UTR are from the SMN1 gene. In another embodiment, the 5'-UTR and/or 3'-UTR are from the SMN2 gene.

In one embodiment, the nucleic acid construct comprises a reporter gene operably linked to the 5'-UTR of SMN or a fragment, mutant, or post-transcriptional regulatory element thereof, and the 3'-UTR of SMN or a fragment, mutant, or post-transcriptional regulatory element thereof, wherein the 5'-UTR is upstream of the reporter gene and the 3'-UTR is downstream of the reporter gene.

In a particular embodiment, the reporter gene is selected from the group consisting of a nucleotide sequence encoding or coding for firefly luciferase, renilla luciferase, click beetle luciferase, green fluorescent protein, yellow fluorescent protein, red fluorescent protein, cyan fluorescent protein, blue fluorescent protein, beta-galactosidase, beta-glucoronidase, beta-lactamase, chloramphenicol acetyltransferase and alkaline phosphatase. In a further embodiment, the nucleic acid construct described herein optionally further comprises one or more operably linked promoters.

The present invention provides for a host cell containing a nucleic acid construct described herein. In one embodiment, a host cell contains a nucleic acid construct comprising a reporter gene operably linked to (i) the 5'-UTR of SMN or a fragment, mutant or post-transcriptional regulatory element thereof and the 3'-UTR of SMN or a fragment, mutant or post-transcriptional regulatory element thereof, (ii) the 5'-UTR of SMN or a fragment, mutant or post-transcriptional regulatory element thereof; or (iii) the 3'-UTR of SMN or a fragment, mutant or post-transcriptional regulatory element thereof, wherein the 5' UTR is upstream of the reporter gene and the 3' UTR is downstream of the reporter gene.

The present invention also is directed to a vector comprising a nucleic acid construct described herein. In a particular embodiment, the vector comprises a nucleic acid construct, wherein the nucleic acid construct comprises a reporter gene operably linked to (i) the 5'-UTR of SMN or a fragment, mutant or post-transcriptional regulatory element thereof and the 3'-UTR of SMN or a fragment, mutant or post-transcriptional regulatory element thereof, (ii) the 5'-UTR of SMN or a fragment, mutant or post-transcriptional regulatory element thereof; or (iii) the 3'-UTR of SMN or a fragment, mutant or post-transcriptional regulatory element thereof wherein the 5' UTR is upstream of the reporter gene and the 3' UTR is downstream of the reporter gene.

The present invention also provides for a host cell containing a vector described herein. In one embodiment, the host cell contains a vector comprising a nucleic acid construct, wherein the nucleic acid construct comprises a reporter gene operably linked to (i) the 5'-UTR of SMN or a fragment, mutant or post-transcriptional regulatory element thereof and the 3'-UTR of SMN or a fragment, mutant or post-transcriptional regulatory element thereof, (ii) the 5'-UTR of SMN or a fragment, mutant or post-transcriptional regulatory element thereof; or (iii) the 3'-UTR of SMN or a fragment, mutant or post-transcriptional regulatory element thereof, wherein the 5' UTR is upstream of the reporter gene and the 3' UTR is downstream of the reporter gene.

The present invention also encompasses a cell-free extract containing the RNA transcribed from a DNA version of a nucleic acid construct described herein. In a specific embodiment, the cell-free extract contains the RNA transcribed from a DNA version of a nucleic acid construct comprising a reporter gene operably linked to (i) the 5'-UTR of SMN or a fragment, mutant or post-transcriptional regulatory element thereof and the 3'-UTR of SMN or a fragment, mutant or post-transcriptional regulatory element thereof, (ii) the 5'-UTR of SMN or a fragment, mutant or post-transcriptional regulatory element thereof; or (iii) the 3'-UTR of SMN or a fragment, mutant or post-transcriptional regulatory element thereof, wherein the 5' UTR is upstream of the reporter gene and the 3' UTR is downstream of the reporter gene.

The invention is based, in part, on the Applicants' discovery that the 5'-UTR of SMN mRNA down-regulates the expression of SMN protein post-transcriptionally; whereas the 3'-UTR of SMN mRNA stimulates the expression of SMN protein post-transcriptionally. Compounds that destabilize the structure and down-regulate or reduce the activity of the SMN 5'-UTR are expected to increase the expression of SMN or SMNΔEx7 protein post-transcriptionally. Compounds that stabilize the structure and up-regulate or increase the activity of the SMN 3'-UTR are expected to increase the expression of SMN or SMNΔEx7 protein post-transcriptionally. Compounds that simultaneously down-regulate the activity of the SMN 5'-UTR and up-regulate the activity of the SMN 3'-UTR are expected to increase the expression of SMN or SMNΔEx7 protein post-transcriptionally.

The UTR targeted approach of the invention has several advantages. In particular, the sequences of the 5'-UTR and 3'-UTR appear to be unique to the SMN transcripts. Therefore, compounds that are highly specific for these UTRs can be used to selectively up-regulate post-transcriptional expression of SMN. The use of such compounds in the methods of the invention should, therefore, have reduced side effects to non-specific targets and cells. Moreover, the UTR targeted approach of the invention exploits the high degree of sequence homology between the SMN1 and SMN2 UTRs and can increase the expression of both SMN1 and SMN2 gene products. In addition, the UTR targeted approach described herein exploits the endogenous regulatory elements of SMN expression, thus, avoiding many technical, safety, and efficacy issues involved with other therapeutic approaches envisioned for the treatment of SMA, e.g., genetic approaches to deliver DNA encoding therapeutic genes or to modify endogenous mutated genes. The UTR targeted approach described herein also circumvents the adverse immunogenic responses associated with antibody therapeutics. Thus, the methods of the present invention described herein offer several advantages, in terms of increased specificity and efficacy and reduced side effects.

Without being bound by any particular theory, the compounds that target any of the 5'-UTR and 3'-UTR, the 5'-UTR or the 3'-UTR of SMN, when used therapeutically, may increase both SMN or SMNΔEx7 in SMA patients and protect motor neurons from degeneration. Thus, the present invention is directed to a method for up-regulating the expression of either or both SMN or SMNΔEx7 protein in a human subject in need thereof, comprising administering an effective amount of a compound to the human subject, which compound has demonstrated activity for enhancing in vitro or in cultured cells the post-transcriptional expression of a nucleic acid construct comprising a reporter gene operably linked to any of the 5'-UTR and 3'-UTR, the 5'-UTR or the 3'-UTR of SMN, wherein the 5'-UTR is upstream and the 3'-UTR is downstream. In one embodiment, the 5'-UTR and/or 3'-UTR are from the SMN1 gene. In another embodiment, the 5'-UTR and/or 3'-UTR are from the SMN2 gene.

Accordingly, the present invention is directed to a method for up-regulating the expression of either or both SMN or SMNΔEx7 protein in a human subject in need thereof, comprising administering to the human subject an effective amount of a compound that upregulates the expression of SMN or SMNΔEx7 protein post-transcriptionally. The present invention is further directed to a method for treating SMA in a human subject in need thereof, comprising administering to the human subject an effective amount of a compound for up-regulating expression of either or both SMN or SMNΔEx7 protein expression, wherein said compound increases in vitro or in cultured cells the post-transcriptional expression of a nucleic acid construct comprising a reporter gene operably linked to any of the 5'-UTR and 3'-UTR, the 5'-UTR or the 3'-UTR of SMN, wherein the 5' UTR is upstream of the reporter gene and the 3' UTR is downstream of the reporter gene. In one embodiment, the 5'-UTR and 3'-UTR from the SMN gene are used. In another embodiment, the 5'-UTR and 3'-UTR from the SMN2 gene are used.

In one embodiment, a method for up-regulating the expression of either or both SMN or SMNΔEx7 protein in a human subject in need thereof, comprises administering to the human subject an effective amount of a compound that up-regulates in vitro or in cultured cells the post-transcriptional expression of a nucleic acid construct comprising a reporter gene operably linked to (i) the 5'-UTR of SMN, or (ii) the 3'-UTR of SMN, or (iii) the 5'-UTR and 3'-UTR of SMN, and wherein the 5'-UTR is upstream of the reporter gene and the 3'-UTR is downstream of the reporter gene.

In one embodiment, a method for treating SMA in a human subject in need thereof, comprises administering to the human subject an effective amount of a compound that up-regulates in vitro or in cultured cells the post-transcriptional expression of a nucleic acid construct comprising a reporter gene operably linked to (i) the 5'-UTR of SMN, or (ii) the 3'-UTR of SMN, or (iii) the 5'-UTR and 3'-UTR of SMN, wherein the 5'-UTR is upstream of the reporter gene and the 3'-UTR is downstream of the reporter gene. In another embodiment, the method further comprises administering to the subject one or more additional agents. In a specific embodiment, the additional agents are agents that up-regulate the expression of either or both SMN or SMNΔEx7 protein transcriptionally.

An embodiment of one or more uses and methods of the present invention is directed to a compound that up-regulates post-transcriptional expression of SMN or a pharmaceutically acceptable free acid, free base, salt, ester, hydrate, solvate, polymorph, clathrate, geometric isomer, stereoisomer, racemate, enantiomer or tautomer thereof, wherein the compound is selected from the group consisting of:

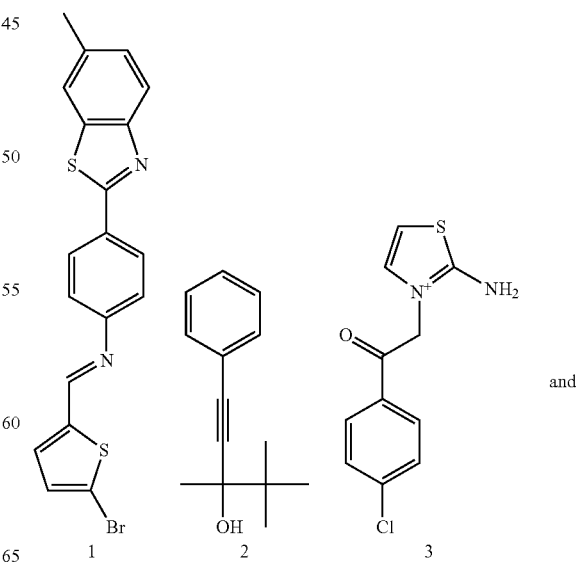

-continued

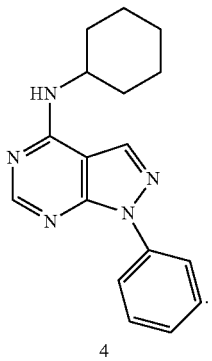

4

In a specific embodiment, the present invention provides methods for up-regulating the expression of either or both SMN or SMNΔEx7 protein in a human subject in need thereof, comprising administering to the human subject an effective amount of a compound, wherein the compound is: (E)-N-((5-bromothiophen-2-yl)methylene)-4-(6-methylbenzo[d]thiazol-2-yl)aniline, 3,4,4-trimethyl-1-phenylpent-1-yn-3-ol, 2-amino-3-(2-(4-chlorophenyl)-2-oxoethyl)thiazol-3-ium, or N-cyclohexyl-1-phenyl-1H-pyrazolo[3,4-d]pyrimidin-4-amine, or a pharmaceutically acceptable free acid, free base, salt, ester, hydrate, solvate, polymorph, clathrate, geometric isomer, stereoisomer, racemate, enantiomer or tautomer thereof.

In another embodiment, the present invention provides methods for treating SMA in a human subject in need thereof, comprising administering to the human subject an effective amount of a compound that up-regulates in vitro or in cultured cells the post-transcriptional expression of a nucleic acid construct comprising a reporter gene operably linked to (i) the 5'-UTR of SMN, or (ii) the 3'-UTR of SMN, or (iii) the 5'-UTR and 3'-UTR of SMN, and wherein the 5'-UTR is upstream of the reporter gene and the 3'-UTR is downstream of the reporter gene. In a specific embodiment, the compound is: (E)-N-((5-bromothiophen-2-yl)methylene)-4-(6-methylbenzo[d]thiazol-2-yl)aniline, 3,4,4-trimethyl-1-phenylpent-1-yn-3-ol, 2-amino-3-(2-(4-chlorophenyl)-2-oxoethyl)thiazol-3-ium, or N-cyclohexyl-1-phenyl-1H-pyrazolo[3,4-d]pyrimidin-4-amine, or a pharmaceutically acceptable free acid, free base, salt, ester, hydrate, solvate, polymorph, clathrate, geometric isomer, stereoisomer, racemate, enantiomer or tautomer thereof.

In yet another embodiment, the present invention provides methods for treating SMA in a human subject in need thereof, comprises administering to the human subject an effective amount of a pharmaceutical composition comprising: (E)-N-((5-bromothiophen-2-yl)methylene)-4-(6-methylbenzo[d]thiazol-2-yl)aniline, 3,4,4-trimethyl-1-phenylpent-1-yn-3-ol, 2-amino-3-(2-(4-chlorophenyl)-2-oxoethyl)thiazol-3-ium, or N-cyclohexyl-1-phenyl-1H-pyrazolo[3,4-d]pyrimidin-4-amine, or a pharmaceutically acceptable free acid, free base, salt, ester, hydrate, solvate, polymorph, clathrate, geometric isomer, stereoisomer, racemate, enantiomer or tautomer thereof, in an admixture with a pharmaceutically acceptable carrier, excipient, or diluent.

Terminology

As used herein, the italicized form of "SMN", unless otherwise specified or clear from the context of the specification, refers to a SMN1 nucleic acid sequence or SMN2 nucleic acid sequence. In a specific embodiment, the italicized form of "SMN" refers to a SMN1 nucleic acid sequence. In another embodiment, the italicized form of "SMN" refers to a SMN2 nucleic acid sequence. The nucleic acid sequence may be DNA or RNA.

As used herein, the term "ARE" refers to an adenylate uridylate rich element in the 3'-UTR of SMN.

As used herein, the term "AU rich" region refers to a region in the 3'-UTR of SMN rich in adensosine and uridine.

As used herein, the term "about" or "approximately" when used in conjunction with a number refers to any number within 0.25%, 0.5%, 1%, 5% or 10% of the referenced number.

As used herein, the term "compound," unless otherwise specified or clear from the context in the specification, refers to any agent that is being tested for its ability to modulate post-transcriptional expression of SMN or has been identified as modulating the post-transcriptional expression of the SMN gene. In a specific embodiment a compound is any agent that is tested for its ability to modulate untranslated region-dependent expression of SMN, or has been identified as modulating the expression of SMN. In one embodiment, a compound is a purified small molecule including, but not limited to, peptides, peptidomimetics, amino acids, amino acid analogs, polynucleotides, polynucleotide analogs, nucleotides, nucleotide analogs, other organic and inorganic compounds (i.e., including heteroorganic and organometallic compounds) having a molecular weight less than about 10,000 grams per mole, or a molecular weight less than about 5,000 grams per mole, or a molecular weight less than about 1,000 grams per mole, or a molecular weight less than about 500 grams per mole, or a molecular weight less than about 100 grams per mole, and salts, esters, and other pharmaceutically acceptable forms thereof.

As used herein, the term "purified," in the context of a compound, refers to a compound that is substantially free of chemical precursors, intermediate compounds or other chemicals (such as reagents, solvents and the like) after being separated from the synthetic reaction mixture. In a specific embodiment, the compound is 60%, preferably 65%, 70%, 75%, 80%, 85%, 90%, or 99% free of such other, different chemicals or compounds. In a specific embodiment, a compound described herein is purified.

As used herein, the term "CU-rich region" refers to a region of the 3'-UTR of SMN rich in cytosine and uridine.

As used herein, the term "GC-rich region" refers to a region of any of the 5'-UTR and 3'-UTR, the 5'-UTR or the 3'-UTR of SMN rich in guanine and cytosine.

As used herein, the term "fragment" refers to a nucleotide sequence comprising an nucleic acid sequence of at least 5 contiguous nucleic acid residues, at least 10 contiguous nucleic acid residues, at least 15 contiguous nucleic acid residues, at least 20 contiguous nucleic acid residues, at least 25 contiguous nucleic acid residues, at least 40 contiguous nucleic acid residues, at least 50 contiguous nucleic acid residues, at least 60 contiguous nucleic acid residues, at least 70 contiguous nucleic acid residues, at least contiguous 80 nucleic acid residues, at least contiguous 90 nucleic acid residues, at least contiguous 100 nucleic acid residues, at least contiguous 125 nucleic acid residues, at least 150 contiguous nucleic acid residues, at least contiguous 175 nucleic acid residues, at least contiguous 200 nucleic acid residues, or at least contiguous 250 nucleic acid residues of the nucleotide sequence of the gene of interest, e.g., SMN. The nucleic acid may be RNA, DNA, or a chemically modified variant thereof. In a specific embodiment, the fragment is a fragment of a UTR of SMN. In a specific embodiment, a fragment of the UTR region of the SMN1 or SMN2 mRNA transcripts retains at least one element of the UTR (e.g., an ARE).

As used herein, the term "target RNA", unless otherwise defined herein, refers to the RNA transcribed from the SMN1 and/or SMN2 gene.

As used herein, the term "host cell" includes a particular subject cell transformed or transfected with a nucleic acid construct of the present invention and the progeny or potential progeny of such a cell. Progeny of such a cell may not be identical to the parent cell transfected with the nucleic acid construct due to mutations or environmental influences that may occur in succeeding generations or integration of the nucleic acid construct into the host cell genome. In one embodiment, a host cell includes a particular subject cell stably transformed or transfected with the nucleic acid construct of the present invention and the progeny or potential progeny of such a cell.

In some embodiments, the terms "nucleic acid", "nucleotide" and "polynucleotide" refer to deoxyribonucleotides, deoxyribonucleic acids, ribonucleotides, and ribonucleic acids, and polymeric forms thereof, and include either single- or double-stranded forms. In certain embodiments, such terms include known analogues of natural nucleotides, for example, peptide nucleic acids ("PNA"s), that have similar binding properties as the reference nucleic acid. In some embodiments, such terms refer to deoxyribonucleic acids (e.g., cDNA or DNA). In other embodiments, such terms refer to ribonucleic acid (e.g., mRNA or RNA).

As used herein, the term "ORF" refers to the open reading frame of a mRNA, i.e., the region of the mRNA that is translated into protein.

As used herein, the term "previously determined reference range" refers to a reference range for the expression of a reporter gene expressed either by an instant nucleic acid construct or the SMN gene from a particular cell or in a particular cell-free extract. Ideally, each laboratory will establish its own reference range for each assay, each cell type and each cell-free extract. In one embodiment, at least one positive control or at least one negative control are included for use in the assay. In a specific embodiment, the previously determined reference range is the amount or activity of the reporter protein detected in the presence of a negative control (e.g., PBS or DMSO).

As used herein, the term "UTR" refers to an "untranslated region" of a nucleotide sequence of a mRNA or DNA sequence or chemical analog thereof that is transcribed into a mRNA in which the nucleotides corresponding to the open reading frame ("ORF") are not present. In some embodiments, the UTR is the region of a mRNA that is not translated into protein. In one embodiment, the UTR is either or both a 5'-UTR, i.e., upstream of the ORF coding region, or a 3'-UTR, i.e., downstream of the ORF coding region.

As used herein, the term "uORF" refers to an upstream open reading frame that is in the 5'-UTR of the main open reading frame, i.e., that encodes a functional protein, of a mRNA.

As used herein, the term "untranslated region-dependent expression" or "UTR-dependent expression" refers to the regulation of gene expression through the untranslated region's regulatory elements at the level of mRNA expression, i.e., during or after transcription of the gene from the DNA has begun. In one embodiment, the term "untranslated region-dependent expression" or "UTR-dependent expression" refers to the regulation of mRNA translation.

As used herein, the terms "reporter gene expression," "expression of a reporter gene", "expression of the reporter gene", or "expression of a nucleic acid construct comprising a reporter gene" are used coextensively and refer to the amount or activity of the reporter protein detected in the assays described herein.

As used herein, the term "effective amount" in the context of administering a compound to a subject refers to the amount of a compound which is sufficient to achieve at least one or more of the following effects: (i) reduce or ameliorate the severity of SMA or a symptom associated therewith; (ii) prevent the progression of SMA or a symptom associated therewith; (iii) cause regression of SMA or a symptom associated therewith; (iv) prevent the development or onset of SMA or a symptom associated therewith; (v) prevent the recurrence of a symptom associated with SMA; (vi) reduce the loss of muscle strength; (vii) increase muscle strength; (viii) reduce the loss of motor neurons; (ix) increase motor neurons (x) reduce muscle atrophy; (xi) protect SMN-deficient motor neurons from degeneration; (xii) increase motor function; (xiii) increase pulmonary function; (xiv) reduce the loss of pulmonary function; (xv) reduce the number of symptoms associated with SMA; (xvi) increase the survival of a subject; (xvi) reduce hospitalization of a subject; (xvii) reduce hospitalization length; (xix) increase the survival of a subject having SMA; and (xx) enhance or improve the prophylactic or therapeutic effect(s) of another therapy.

An "isolated" nucleic acid sequence, nucleotide sequence, or polynucleotide sequence is one which is separated from other nucleic acid molecules which are present in a natural source of the nucleic acid sequence or nucleotide sequence. Moreover, an "isolated" nucleic acid sequence, or nucleotide sequence, or polynucleotide sequence, such as a cDNA or RNA molecules, can be substantially free of other cellular material or culture medium when produced by recombinant techniques, or substantially free of chemical precursors when chemically synthesized. In certain embodiments, an "isolated" nucleic acid sequence, nucleotide sequence, or polynucleotide sequence is a nucleic acid sequence, nucleotide sequence, or polynucleotide sequence that is recombinantly expressed in a heterologous cell. In a specific embodiment, a nucleic acid construct described herein is isolated.

As used herein, the term "in combination," refers, in the context of the administration of a compound of the present invention, to the administration of one or more compounds that up-regulate the expression of either or both SMN or SMNΔEx7 protein post-transcriptionally alone or in combination with one or more additional agents for use in treating SMA. The use of the term "in combination" does not restrict the order in which one or more compounds of the present invention or another agent are administered to a human subject having SMA.

As used herein, the term "premature human infant" refers to a human infant born at less than 37 weeks of gestational age.

As used herein, the term "human infant" refers to a newborn to 1 year old year human.

As used herein, the term "human child" refers to a human that is 1 year to 18 years old.

As used herein, the term "human adult" refers to a human that is 18 years or older.

As used herein, the term "elderly human" refers to a human 65 years or older.

As used herein, the term "human toddler" refers to a human that is 1 year to 3 years old.

As used herein, the terms "subject" or "patient" are used interchangeably. As used herein, the terms "subject" and "subjects" refer to an animal, preferably a mammal including a non-primate (e.g., a camel, donkey, zebra, cow, pig, horse, goat, sheep, cat, dog, rat, and mouse) and a primate (e.g., a monkey, chimpanzee, and a human), and most preferably a human.

As used herein, the term "synergistic," refers to the effect of the administration of a combination product as described herein which is more effective than the additive effects of any two or more single agents. In a specific embodiment, a synergistic effect of a combination product permits the use of lower dosages of one or more agents and/or less frequent administration of said agents to a subject with SMA. In certain embodiments, the ability to utilize lower dosages of an agent and/or to administer said agents less frequently reduces the toxicity associated with the administration of said agents to a subject without reducing the efficacy of said agents in the prevention or treatment of SMA. In some embodiments, a synergistic effect results in improved efficacy of each of the agents in treating SMA. In some embodiments, a synergistic effect of a combination of agents avoids or reduces adverse or unwanted side effects associated with the use of any single agent. The combination of agents in such a product can be administered to a subject in the same pharmaceutical composition. Alternatively, the agents can be administered concurrently to a subject in separate pharmaceutical compositions. The agents may also be administered to a subject by the same or different routes of administration. In a specific embodiment, at least one of the agents is a compound.

As used herein, the term "treat" refers to treatment from which a subject receives a beneficial effect such as the reduction, decrease, attenuation, diminishment, stabilization, remission, suppression, inhibition or arrest of the development or progression of SMA, or a symptom thereof. In certain embodiments, the treatment that a subject receives results in at least one or more of the following effects: (i) reduce or ameliorate the severity of SMA or a symptom associated therewith; (ii) prevent the progression of SMA or a symptom associated therewith; (iii) cause regression of SMA or a symptom associated therewith; (iv) prevent the development or onset of SMA or a symptom associated therewith; (v) prevent the recurrence of a symptom associated with SMA; (vi) reduce the loss of muscle strength; (vii) reduce the loss of muscle cells; (viii) enhance or improve muscle strength; (ix) increase muscle cells; (x) reduce muscle dystrophy; (xi) increase motor function; (xii) reduce the duration of a symptom associated with SMA; (xiii) reduce the number of symptoms associated with SMA; (xiv) reduce hospitalization associated with SMA in a subject; (xv) reduce hospitalization length associated with SMA; (xvi) increase the survival of a subject having SMA; and (xvii) enhance or improve the prophylactic or therapeutic effect(s) of another agent. In some embodiments, the treatment that a subject receives does not cure SMA, but prevents the progression or worsening of the disease.

As used herein, the term "form" in the context of a compound refers to a compound isolated for use as a pharmaceutically acceptable free acid, free base, salt, ester, hydrate, solvate, polymorph, clathrate, geometric isomer, stereoisomer, racemate, enantiomer or tautomer thereof.

As used herein, the term "pharmaceutically acceptable" refers to a component that is, within the scope of sound medical judgment, suitable for use in contact with the tissues of humans and other mammals without undue toxicity, irritation, allergic response and the like, and are commensurate with a reasonable benefit/risk ratio.

As used herein, the term "pharmaceutically acceptable salt" refers to any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a subject in need thereof. Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

As used herein, the term "hydrate" refers to a compound which further includes a stoichiometric or non-stoichiometric amount of water bound by non-covalent intermolecular forces.

As used herein, the term "solvate" refers to a compound which further includes a stoichiometric or non-stoichiometric amount of solvent such as water, acetone, ethanol, methanol, dichloromethane, 2-propanol, or the like, bound by non-covalent intermolecular forces.

BRIEF DESCRIPTION OF THE DRAWINGS

FIG. 1: SMN 5'-UTR: DNA nucleotide sequence corresponding to the 5'-UTR of both human SMN1 and human SMN2 (SEQ ID NO: 1). The bolded sequences correspond to the upstream open reading frame (uORF), which encodes 9 amino acids. The 5'-UTR of human SMN1 and human SMN2 is 163 nucleotides in length and is 63% GC rich.

FIG. 2: SMN1 3'-UTR: DNA nucleotide sequence corresponding to the 3'-UTR of human SMN1 (SEQ ID NO: 2), which is 559 nucleotides in length, comprises 4 ARE elements (shown in bold), 2 CU-rich elements (shown by underline), and one GC-rich region (shown by double-underline).

FIG. 3: SMN2 3'-UTR: DNA nucleotide sequence corresponding to the 3'-UTR of human SMN2 (SEQ ID NO: 3), which is 559 nucleotides in length, comprises 4 ARE elements (shown in bold), 2 CU-rich elements (shown by underline), and one GC-rich region (shown by double-underline).

DETAILED DESCRIPTION OF THE INVENTION

Figure 4:
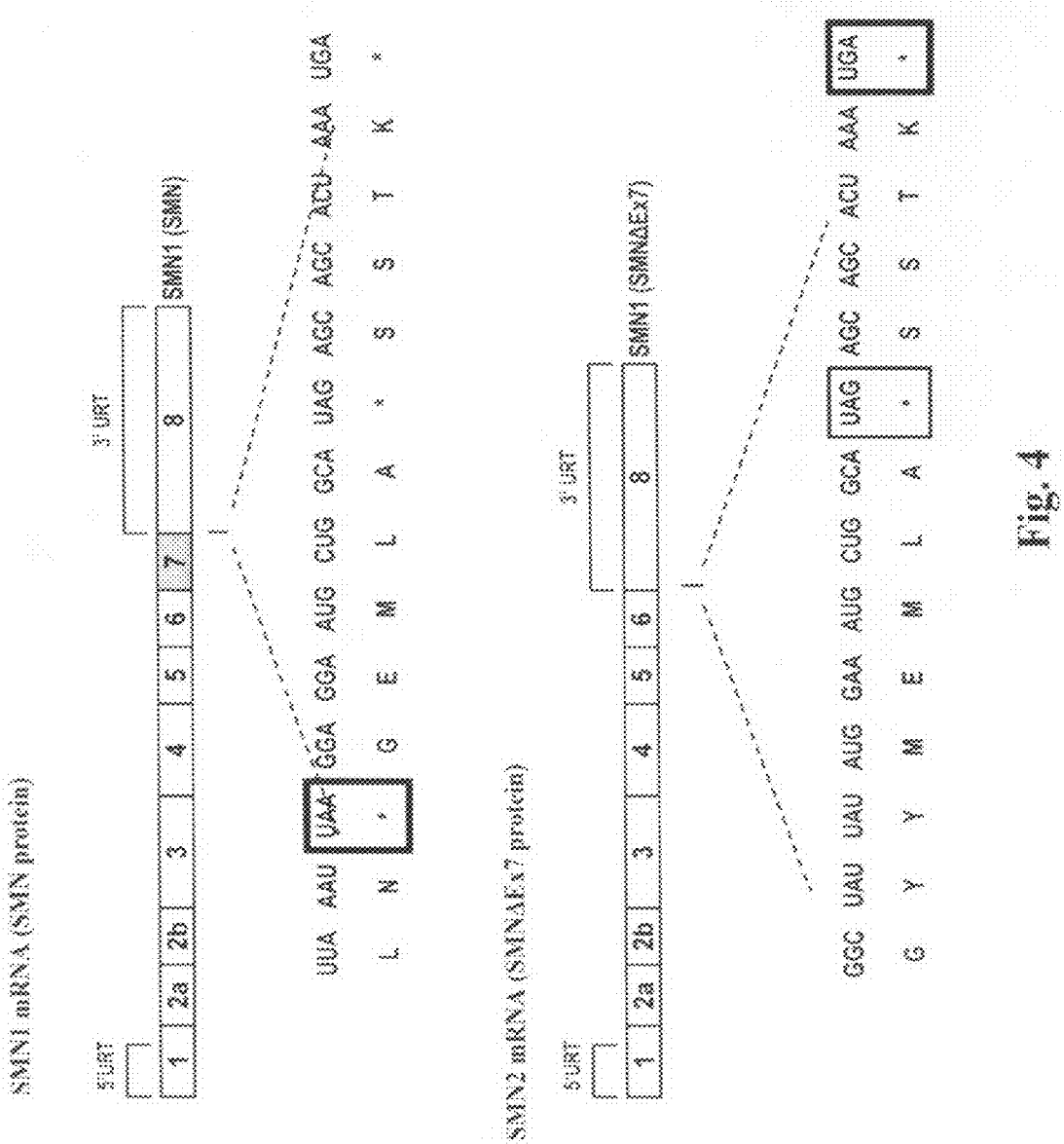
FIG. 4: Difference in 3'-UTRs of human SMN1 and human SMN2 mRNA: Schematic representation of the SMN1 mRNA transcript and the SMN2 mRNA transcript coding for SMN and SMNΔEx7 protein, respectively. The differences in the amino acid sequences between the 3'-UTRs of SMN1 and SMN2 are shown.

The present invention provides compounds for use in the treatment of SMA. In particular, the present invention provides a method for the treatment of SMA in a human subject in need thereof, comprising administering an effective amount of a compound to the human subject, in which said compound increases the post-transcriptional expression in vitro or in cultured cells of a nucleic acid construct comprising a reporter gene operably linked to any of the 5'-UTR and 3'-UTR, the 5'-UTR or the 3'-UTR of SMN, wherein the 5'-UTR is upstream of the reporter gene and the 3'-UTR is downstream of the reporter gene.

Without being bound by any particular theory, the compounds target any of the 5'-UTR and 3'-UTR, the 5'-UTR or the 3'-UTR of SMN and increase the expression of either or both SMN or SMNΔEx7 in SMA patients, which provides a therapeutic benefit. In a specific embodiment, the compounds bind directly to any of the 5'-UTR and 3'-UTR, the 5'-UTR or the 3'-UTR of SMN RNA and increase expression of either or both SMN or SMNΔEx7 protein in SMA patients, which provides a therapeutic benefit. In another embodiment, the compounds bind to proteins and/or molecules that bind and/or associate with any of the 5'-UTR and 3'-UTR, the 5'-UTR or the 3'-UTR of SMN. In another embodiment, the compounds bind to nucleotide regulatory sequences of genes that encode proteins that bind and/or associate with any of the 5'-UTR and 3'-UTR, the 5'-UTR or the 3'-UTR of SMN.

The present invention provides screening assays for the identification or validation of compounds that target any of the 5'-UTR and 3'-UTR, the 5'-UTR or the 3'-UTR of SMN mRNA transcripts. These assays involve the use of a nucleic acid construct comprising a reporter gene operably linked to any of the 5'-UTR and 3'-UTR, the 5'-UTR or the 3'-UTR of SMN, wherein the 5'-UTR is upstream of the reporter gene and the 3'-UTR is downstream of the reporter gene. Compounds that specifically increase the post transcriptional activity of any of the 5'-UTR and 3'-UTR, the 5'-UTR or the 3'-UTR of SMN and enhance expression of the reporter gene are expected to provide a therapeutic benefit. In a specific embodiment, compounds for therapeutic use demonstrate central nervous system penetration when used in vivo.

Compounds selected for use in the invention include those that bind directly to any of the 5'-UTR and 3'-UTR, the 5'-UTR or the 3'-UTR of SMN. Compounds selected for use in the invention also include those that bind to proteins and/or molecules that bind and/or associate with any of the 5'-UTR and 3'-UTR, the 5'-UTR or the 3'-UTR of SMN. Compounds selected for use in the invention also include those that bind to nucleotide regulatory sequences of genes that encode proteins that bind and/or associate with any of the 5'-UTR and 3'-UTR, the 5'-UTR or the 3'-UTR of SMN.

The subsections below describe in more detail the type of compounds that enhance the post-transcriptional expression of a nucleic acid construct comprising a reporter gene operably linked to any of the 5'-UTR and 3'-UTR, the 5'-UTR or the 3'-UTR of SMN, screening assays for identifying or validating compounds that enhance the post-transcriptional expression of SMN or SMNΔEx7 protein post-transcriptionally, methods for characterizing compounds, and methods of using the compounds to treat SMA.

Compounds

The compounds screened in the in vitro and cultured host cell assays of the present invention have demonstrated activity for increasing the post-transcriptional expression of a nucleic acid construct comprising a reporter gene operably linked to any of the 5'-UTR and 3'-UTR, the 5'-UTR or the 3'-UTR of SMN and, thus may post-transcriptionally increase, enhance, or upregulate expression of either or both SMN or SMNΔEx7 protein. In an embodiment, the compounds are specific for any of the 5'-UTR and 3'-UTR, the 5'-UTR or the 3'-UTR of SMN target mRNA transcripts and thus may post-transcriptionally increase, enhance, or upregulate expression of either or both SMN or SMNΔEx7 protein by stabilizing the mRNA transcripts of either or both SMN or SMNΔEx7 protein, respectively.

Accordingly, the methods of the present invention are directed to a compound or a pharmaceutically acceptable free acid, free base, salt, ester, hydrate, solvate, polymorph, clathrate, geometric isomer, stereoisomer, racemate, enantiomer or tautomer thereof for use in modulating UTR-dependent expression of SMN, wherein the compound is selected from the group consisting of:

| Cpd | Name |
|---|---|
| 1 | (E)-N-((5-bromothiophen-2-yl)methylene)-4-(6-methylbenzo[d]thiazol-2-yl)aniline, |
| 2 | 3,4,4-trimethyl-1-phenylpent-1-yn-3-ol, |
| 3 | 2-amino-3-(2-(4-chlorophenyl)-2-oxoethyl)thiazol-3-ium, and |
| 4 | N-cyclohexyl-1-phenyl-1H-pyrazolo[3,4-d]pyrimidin-4-amine. |

In a specific embodiment, the compound is a pharmaceutically acceptable free acid, free base, salt, ester, hydrate, solvate, polymorph, clathrate, geometric isomer, stereoisomer, racemate, enantiomer or tautomer of compound 1, 2, 3, or 4 above.

Nucleic Acid Constructs

The present invention provides for nucleic acid constructs comprising a reporter gene operably linked to any of the 5'-UTR and 3'-UTR of SMN, the 5'-UTR of SMN or the 3'-UTR of SMN, or a fragment, mutant or a post-transcriptional regulatory element thereof, wherein the 5'-UTR is 5' (upstream) of the reporter gene and the 3'-UTR is 3' (downstream) of the reporter gene. In a specific embodiment, the nucleic acid construct comprises the 5'-UTR of human SMN1 or a fragment thereof and the 3'-UTR of human SMN1 or a fragment thereof. In another embodiment, the nucleic acid construct comprises the 5'-UTR of human SMN1 or a fragment thereof or the 3'-UTR of human SMN1 or a fragment thereof. In another embodiment, the nucleic acid construct comprises the 5'-UTR of human SMN2 or a fragment thereof and the 3'-UTR of human SMN2 or a fragment thereof. In yet another embodiment the nucleic acid construct comprises the 5'-UTR of human SMN2 or a fragment thereof, or the 3'-UTR of human SMN2 or a fragment thereof. The nucleic acid constructs of the invention may be used in the screening assays described herein, to identify or validate compounds that post-transcriptionally enhance the expression of a protein translated from an SMN1 mRNA transcript(s) or protein translated from a SMN2 mRNA transcript(s).

The present invention provides a nucleic acid construct comprising the 5'-UTR of SMN (FIG. 1; SEQ ID NO:1) or a fragment, mutant or a post-transcriptional regulatory element thereof and a reporter gene, wherein the 5'-UTR or a fragment, mutant or a post-transcriptional regulatory element thereof is operably linked to the reporter gene and the 5'-UTR or a fragment, mutant or a post-transcriptional regulatory element thereof is 5' (upstream) of the reporter gene. The present invention also provides a nucleic acid construct comprising the 3'-UTR of SMN (FIG. 2; SEQ ID NO:2) or a fragment, mutant or a post-transcriptional regulatory element thereof, wherein the 3'-UTR or a fragment, mutant or a post-transcriptional regulatory element thereof is operably linked to the reporter gene and the 3'-UTR or a fragment, mutant or a post-transcriptional regulatory element thereof is 3' (downstream) of the reporter gene. The present invention also provides a nucleic acid construct comprising the 3'-UTR of SMN2 (FIG. 3; SEQ ID NO:3) or a fragment, mutant or a post-transcriptional regulatory element thereof and a reporter gene, wherein the 3'-UTR or a fragment, mutant or a post-transcriptional regulatory element thereof is operably linked to the reporter gene and the 3'-UTR or a fragment, mutant or a post-transcriptional regulatory element thereof of is 3' (downstream) of the reporter gene. The present invention also provides a nucleic acid construct comprising the 5'-UTR of SMN (FIG. 1: SEQ ID NO: 1) or a fragment, mutant or a post-transcriptional regulatory element thereof, a reporter gene, and the 3'-UTR of SMN1 (FIG. 2; SEQ ID NO:2) or a fragment, mutant or a post-transcriptional regulatory element thereof, wherein the 5'-UTR or a fragment, mutant or a post-transcriptional regulatory element thereof and 3'-UTR or a fragment, mutant or a post-transcriptional regulatory element thereof are operably linked to the reporter gene, and wherein the 5'-UTR or a fragment, mutant or a post-transcriptional regulatory element thereof is 5' (upstream) of the reporter gene and the 3'-UTR or 5' is 3' (downstream) of the reporter gene. The present invention further provides a nucleic acid construct comprising the 5'-UTR of SMN (FIG. 1; SEQ ID NO: 1) or a fragment, mutant or a post-transcriptional regulatory element thereof, a reporter gene, and the 3'-UTR of SMN2 (FIG. 3; SEQ ID NO:3) or a fragment, mutant or a post-transcriptional regulatory element thereof, wherein the 5'-UTR or a fragment, mutant or a post-transcriptional regulatory element thereof and 3'-UTR or a fragment, mutant or a post-transcriptional regulatory element thereof are operably linked to the reporter gene, and wherein the 5'-UTR or fragment thereof is 5' (upstream) of the reporter gene and the 3'-UTR or fragment thereof is 3' (downstream) of the reporter gene.

The present invention provides nucleic acid constructs comprising a reporter gene and a nucleotide sequence comprising a mutated form of the 5'-UTR of SMN or a fragment thereof, wherein the nucleotide sequence is operably linked to the reporter gene and the nucleotide sequence is upstream of the reporter gene. The present invention provides nucleic acid constructs comprising a reporter gene and a nucleotide sequence comprising a mutated form of the 3'-UTR of SMN1 or fragment thereof, wherein the nucleotide sequence is operably linked to the reporter gene and the nucleotide sequence is downstream of the reporter gene. The present invention provides nucleic acid constructs comprising a reporter gene and a nucleotide sequence comprising a mutated form of the 3'-UTR of SMN2 or fragment thereof, wherein the nucleotide sequence is operably linked to the reporter gene and the nucleotide sequence is downstream of the reporter gene. The present invention also provides a nucleic acid construct comprising a reporter gene, a first nucleotide sequence comprising a mutated form of the 5'-UTR of SMN or a fragment thereof, and a second nucleotide sequence comprising a mutated form of the 3'-UTR of SMN1 or a fragment thereof, wherein the first nucleotide sequence and the second nucleotide sequence are operably linked to the reporter gene, and wherein the first nucleotide sequence is upstream of the reporter gene and the second nucleotide sequence is downstream of the reporter gene.

The present invention also provides a nucleic acid construct comprising a reporter gene, a first nucleotide sequence comprising a mutated form of the 5'-UTR of SMN or a fragment thereof, and a second nucleotide sequence comprising a mutated form of the 3'-UTR of SMN or a fragment thereof, wherein the first nucleotide sequence and the second nucleotide sequence are operably linked to the reporter gene, and wherein the first nucleotide sequence is upstream of the reporter gene and the second nucleotide sequence is downstream of the reporter gene. The present invention also provides a nucleic acid construct comprising a reporter gene, a first nucleotide sequence comprising a mutated form of the 5'-UTR of SMN or a fragment thereof, and a second nucleotide sequence comprising a wild-type form of the 3'-UTR of SMN2 or a fragment thereof, wherein the first nucleotide sequence and the second nucleotide sequence are operably linked to the reporter gene, and wherein the first nucleotide sequence is upstream of the reporter gene and the second nucleotide sequence is downstream of the reporter gene. The present invention also provides a nucleic acid construct comprising a reporter gene, a first nucleotide sequence comprising a wild-type form of the 5'-UTR of SMN or a fragment thereof, and a second nucleotide sequence comprising a mutant form of the 3'-UTR of SMN2 or a fragment thereof, wherein the first nucleotide sequence and the second nucleotide sequence are operably linked to the reporter gene, and wherein the first nucleotide sequence is 5' (upstream) of the reporter gene and the second nucleotide sequence is 3' (downstream) of the reporter gene. The present invention also provides a nucleic acid construct comprising a reporter gene, a first nucleotide sequence comprising a wild-type form of the 5'-UTR of SMN or a fragment thereof, and a second nucleotide sequence comprising a mutant form of the 3-UTR of SMN1 or a fragment thereof, wherein the first nucleotide sequence and the second nucleotide sequence are operably linked to the reporter gene, and wherein the first nucleotide sequence is 5' (upstream) of the reporter gene and the second nucleotide sequence is 3' (downstream) of the reporter gene.

In certain embodiments, a mutated form of the 5'-UTR of SMN or a fragment thereof contains 1, 2, 3, 4, 5, 6, 7, 8, 9, 10 or more mutations. Alternatively, the mutated form of the 5'-UTR of SMN or a fragment thereof contains an amount of mutations in a range of from about one to about five mutations, from about two to about eight mutations or from about five to about ten mutations. In certain embodiments, a mutated form of the 3'-UTR of SMN1 or a fragment thereof contains 1, 2, 3, 4, 5, 6, 7, 8, 9, 10 or more mutations. In certain embodiments, a mutated form of the 3'-UTR of SMN2 or a fragment thereof contains 1, 2, 3, 4, 5, 6, 7, 8, 9, 10 or more mutations. Alternatively, the mutated form of the 3'-UTR of SMN1 or SMN2 or a fragment thereof contains an amount of mutations in a range of from about one to about five mutations, from about two to about eight mutations or from about five to about ten mutations. In either case, such mutations may include, but are not limited to, insertions, deletions, and/or substitutions.

In certain embodiments, a nucleotide sequence comprising a mutated form of the 5'-UTR of SMN is 65%, 75%, 80%, 85%, 90%, 95%, 98% or 99% identical to the nucleotide sequence of the 5'-UTR of SMN (FIG. 1; SEQ ID NO:1). In some embodiments, a nucleotide sequence comprising a mutated form of the 3'-UTR of SMN1 (FIG. 2; SEQ ID NO:2) is 65%, 75%, 80%, 85%, 90%, 95%, 98% or 99% identical to the nucleotide sequence of the 3'-UTR of SMN1 (FIG. 2; SEQ ID NO:2). In some embodiments, a nucleotide sequence comprising a mutated form of the 3'-UTR of SMN2 is 65%, 75%, 80%, 85%, 90%, 95%, 98% or 99% identical to the nucleotide sequence of the 3'-UTR of SMN2 (FIG. 3; SEQ ID NO:3). Percent identity can be determined using any method known to one of skill in the art. In a specific embodiment, the percent identity is determined using the "Best Fit" or "Gap" program of the Sequence Analysis Software Package™ (Version 10; Genetics Computer Group. Inc., University of Wisconsin Biotechnology Center, Madison, Wis.). See, e.g., U.S. Patent Application Publication No. US 2005/0048549, paragraph 74, for information regarding these programs.

In certain embodiments, a nucleotide sequence comprising a mutated form of the 5'-UTR of SMN hybridizes to the nucleotide of the 5'-UTR of SMN (FIG. 1; SEQ ID NO:1). In certain embodiments, a nucleotide sequence comprising a mutated form of the 3'-UTR of SMN1 hybridizes to the nucleotide of the 3'-UTR of SMN1 (FIG. 2; SEQ ID NO:2). In certain embodiments, a nucleotide sequence comprising a mutated form of the 3'-UTR of SMN2 hybridizes to the nucleotide of the 3'-UTR of SMN2 (FIG. 3; SEQ ID NO:3).

In specific embodiments, a nucleotide sequence comprising a mutated form of the 5'-UTR of SMN hybridizes under stringent conditions to a nucleotide sequence of the 5'-UTR of SMN (FIG. 1; SEQ ID NO:1) of at least 20 nucleic acids, at least 30 nucleic acids, at least 40 nucleic acids, at least 50 nucleic acids, at least 100 nucleic acids, or at least 150 nucleic acids. In a specific embodiment, a nucleotide sequence comprising a mutated form of the 5'-UTR of SMN hybridizes under high stringency, intermediate or lower stringency hybridization conditions to a nucleotide sequence of the 5'-UTR of SMN or a fragment thereof. In specific embodiments, a nucleotide sequence comprising a mutated form of the 3'-UTR of SMN1 hybridizes under stringent conditions to a nucleotide sequence of the 3'-UTR of SMN1 (FIG. 2; SEQ ID NO: 2) of at least 20 nucleic acids, at least 30 nucleic acids, at least 40 nucleic acids, at least 50 nucleic acids, at least 100 nucleic acids, or at least 150 nucleic acids. In a specific embodiment, a nucleotide sequence comprising a mutated form of the 3'-UTR of SMN1 hybridizes under high stringency, intermediate or lower stringency hybridization conditions to a nucleotide sequence of the 3'-UTR of SMN or a fragment thereof. In specific embodiments, a nucleotide sequence comprising a mutated form of the 3'-UTR of SMN2 hybridizes under stringent conditions to a nucleotide sequence of the 3'-UTR of SMN2 (FIG. 3; SEQ ID NO: 3) of at least 20 nucleic acids, at least 30 nucleic acids, at least 40 nucleic acids, at least 50 nucleic acids, at least 100 nucleic acids, or at least 150 nucleic acids. In a specific embodiment, a nucleotide sequence comprising a mutated form of the 3'-UTR of SMN hybridizes under high stringency, intermediate or lower stringency hybridization conditions to a nucleotide sequence of the 3'-UTR of SMN2 or a fragment thereof. Hybridization conditions are well known in the art and are described in e.g., U.S. Patent Application Publication No. US 2005/0048549 (e.g., paragraphs 72 and 73), which is herein incorporated by reference in its entirety.

In one embodiment, if only the 5'-UTR of SMN is used in a construct, then a different UTR (unrelated to SMN) may be used as the 3'-UTR in the construct. In another embodiment, if only the 3'-UTR of SMN is used in a construct, then a different UTR (unrelated to SMN) may be used as the 5'-UTR in the construct. In one embodiment, the different UTR may encompass the UTR of any gene that is not SMN or a UTR not found in nature.

In a specific embodiment, the present invention provides a nucleic acid construct comprising a reporter gene and a nucleotide sequence comprising nucleotides 30 to 163 of the 5'-UTR of SMN (SEQ ID NO:4), wherein the nucleotide sequence is operably linked to the reporter gene and the nucleotide sequence is 5' (upstream) of the reporter gene. In another embodiment, the present invention provides a nucleic acid construct comprising a reporter gene and a nucleotide sequence comprising nucleotides 1 to 131 of the 5'-UTR of SMN (SEQ ID NO:5), wherein the nucleotide sequence is operably linked to the reporter gene and the nucleotide sequence is 5' (upstream) of the reporter gene. In another embodiment, the present invention provides a nucleic acid construct comprising a reporter gene and a nucleotide sequence comprising the 5'-UTR of SMN with a mutation that mutates or eliminates the ATG site at nucleotide position 7-9 of SEQ ID NO:1, wherein the nucleotide sequence is operably linked to the reporter gene and the nucleotide sequence is 5' (upstream) of the reporter gene. In another embodiment, the present invention provides a nucleic acid construct comprising a reporter gene and a nucleotide sequence comprising the 5'-UTR of SMN with a mutation that deletes the uORF at nucleotides 7-33 of SEQ ID NO: 1, wherein the nucleotide sequence is operably linked to the reporter gene and the nucleotide sequence is 5' (upstream) of the reporter gene. In accordance with these embodiments, the nucleic acid construct may further comprise a nucleotide sequence comprising the 3'-UTR of SMN, or a fragment or mutant thereof.

The present invention provides nucleic acid constructs comprising a reporter gene and a nucleotide sequence comprising a post-transcriptional regulatory element in any of the 5'-UTR and 3'-UTR, the 5'-UTR or the 3'-UTR of SMN. FIGS. 1-3 identify post-transcriptional regulatory elements in the 5'-UTR of SMN (FIG. 1) and the 3'-UTR of SMN1 and SMN2 (FIGS. 2 and 3, respectively). In one embodiment, the present invention provides nucleic acid constructs comprising a reporter gene and a nucleotide sequence comprising two, three, four or more post-transcriptional regulatory elements in any of the 5'-UTR and 3'-UTR, the 5'-UTR or the 3'-UTR of SMN.

In some embodiments, the 5'-UTR of SMN may be mutated to reduce the secondary or tertiary structure of the UTR. One skilled in the art would know how and be able to identify those regions of the 5'-UTR that contribute to the secondary or tertiary structure of the UTR using techniques known to one of skill in the art. Once those regions contributing to the secondary or tertiary structure of the 5'-UTR have been identified, one of skill in the art would be able to identify which nucleotides to mutate to reduce the secondary or tertiary structure of the UTR and be able to make such mutations using techniques known to one of skill in the art.

In some embodiments, the nucleic acid construct may further comprise a stable hairpin secondary structure inserted into a UTR of SMN. In some embodiments, an intron is inserted into a UTR (e.g., the 5'-UTR) or at the 5' end of an ORF of SMN. In some embodiments, both a stable hairpin secondary structure and an intron are added to the nucleic acid construct. Such insertions and other techniques known to one of skill in the art can be used to obtain a nucleic acid construct suitable for the methods described herein.

The reporter gene in the nucleic acid constructs can be positioned such that the translation of that reporter gene is dependent upon the mode of translation initiation, such as, but not limited to, cap-dependent translation or cap-independent translation (i.e., translation via an internal ribosome entry site).

In addition to any of the 5'-UTR and 3'-UTR, the 5'-UTR or the 3'-UTR of SMN and the reporter gene, the nucleic acid construct may further comprise one or more transcriptional regulatory element(s). The transcriptional regulatory elements are typically 5' to the 5'-UTR of SMN and direct the transcription of the reporter gene. In some embodiments, one or more of the transcriptional regulatory elements that are endogenous to the SMN transcriptional regulatory elements are used to control the transcription of a reporter gene. In other embodiments, one or more transcriptional regulatory elements that are heterologous to SMN are used to control the transcription of a reporter gene. Any transcriptional regulatory element(s) known to one of skill in the art may be used to control the transcription of the reporter gene. Non-limiting examples of the types of transcriptional regulatory element(s) include a constitutive promoter, a tissue-specific promoter, and an inducible promoter. In a specific embodiment, the transcription of the reporter gene is controlled, at least in part, by a mammalian (in some embodiments, human) transcriptional regulatory element(s). In one embodiment, the nucleic acid construct of the present invention optionally comprises one or more promoters operably linked to the reporter gene. In a more specific embodiment, the transcription of the reporter gene is controlled, at least in part, by a strong promoter, such as CMV.

Specific examples of promoters which may be used to control the transcription of the reporter gene include, but are not limited to, the SV40 early promoter region, the promoter contained in the 3' long terminal repeat of Rous sarcoma virus, the herpes thymidine kinase promoter, the regulatory sequences of the metallothionein gene adenovirus (ADV), cytomegalovirus (CMV), bovine papilloma virus (BPV), parovirus B19p6 promoter, prokaryotic expression vectors such as the .beta.-lactamase promoter, or the tac promoter, plant expression vectors comprising the nopaline synthetase promoter region or the cauliflower mosaic virus 35S RNA promoter, and the promoter of the photosynthetic enzyme ribulose biphosphate carboxylase, promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells, insulin gene control region which is active in pancreatic beta cells, immunoglobulin gene control region which is active in lymphoid cells, mouse mammary tumor virus control region which is active in testicular, breast, lymphoid and mast cells, albumin gene control region which is active in liver, alpha-fetoprotein gene control region which is active in liver, alpha 1-antitrypsin gene control region which is active in the liver, beta-globin gene control region which is active in myeloid cells, myelin basic protein gene control region which is active in oligodendrocyte cells in the brain, myosin light chain-2 gene control region which is active in skeletal muscle, and gonadotropic releasing hormone gene control region which is active in the hypothalamus.

The nucleic acid constructs may be part of or otherwise contained in a vector that provides transcriptional regulatory elements and optionally, translational regulatory elements. The vector chosen will depend upon a variety of factors, including, without limitation, the strength of the transcriptional regulatory elements and the host cell or cell-free translation extract to be used to express the reporter gene. Non-limiting examples of host cell-vector systems that may be used to express the reporter gene include mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA; and stable cell lines generated by transformation using a selectable marker.

In one embodiment, the present invention provides for vectors comprising a nucleic acid construct described herein. In a certain embodiment, a vector comprises a nucleic acid construct, wherein the nucleic acid construct comprises a reporter gene operably linked to (i) the 5'-UTR (untranslated region) of SMN or a fragment, mutant or post-transcriptional regulatory element thereof and the 3'-UTR of SMN or a fragment, mutant or post-transcriptional regulatory element thereof, (ii) the 5'-UTR of SMN or a fragment, mutant or post-transcriptional regulatory element thereof; or (iii) the 3'-UTR of SMN or a fragment, mutant or post-transcriptional regulatory element thereof, wherein the 5'-UTR is upstream of the reporter gene and the 3'-UTR is downstream of the reporter gene.

In a specific embodiment, a nucleic acid construct comprises a promoter operably linked to a reporter gene flanked by one or both UTRs of SMN, origins of replication from one or more species, and optionally, one or more selectable markers (e.g. an antibiotic resistance gene). In one embodiment, the nucleic acid construct is a vector a CMV vector, such as pcDNA™ 3.1/Hygro (Invitrogen Corp., Carlsbad, Calif.). In other embodiments, the nucleic acid construct is a vector a T7 vector, a lac vector, pCEP4 vector or 5.0/FRT vector.

The nucleic acid constructs can be monocistronic or multicistronic. A multicistronic nucleic acid construct may encode 2, 3, 4, 5, 6, 7, 8, 9, 10 or more, or in the range of 2-5, 5-10 or 10-20 reporter genes. For example, a dicistronic nucleic acid construct may comprise in the following order a promoter, a first reporter gene, a 5'-UTR of SMN, a second reporter gene and optionally, a 3'-UTR of SMN. In such a nucleic acid construct, the transcription of both reporter genes is driven by the promoter, whereas the translation of the mRNA from the first reporter gene is by a cap-dependent scanning mechanism and the translation of the mRNA from the second reporter gene is by a cap-independent mechanism by an IRES. The IRES-dependent translation of the mRNA of the second reporter gene can be normalized against cap-dependent translation.

Expression vectors containing the nucleic acid construct of the present invention can be identified by four general approaches: (a) nucleic acid sequencing, (b) nucleic acid hybridization, (c) presence or absence of "marker" nucleic acid functions, and (d) expression of inserted sequences. In the first approach, the presence of the UTRs and/or the reporter gene inserted in an expression vector can be detected by sequencing. In the second approach, the presence of the UTRs and/or the reporter gene inserted in an expression vector can be detected by nucleic acid hybridization using probes comprising sequences that are homologous to the inserted UTRs and/or reporter gene. In the third approach, the recombinant vector/host system can be identified and selected based upon the presence or absence of certain "marker" nucleic acid functions (e.g., thymidine kinase activity, resistance to antibiotics, transformation phenotype, occlusion body formation in baculovirus, etc.) caused by the insertion of the nucleic acid of interest, i.e., the nucleic acid construct, in the vector. For example, if the nucleic acid of interest is inserted within the marker nucleic acid sequence of the vector, recombinants containing the insert can be identified by the absence of the marker nucleic acid function. In the fourth approach, recombinant expression vectors can be identified by assaying the reporter gene product expressed by the recombinant. Such assays can be based, for example, on the physical or functional properties of the particular reporter gene.

Techniques for practicing aspects of this invention will employ, unless otherwise indicated, conventional techniques of molecular biology, microbiology, and recombinant DNA manipulation and production, which are routinely practiced by one of skill in the art.

Reporter Genes

Any reporter gene well-known to one of skill in the art may be used in the nucleic acid constructs to ascertain the effect of a compound on post-transcriptional expression of SMN. Reporter genes refer to a nucleotide sequence encoding or coding for a protein that is readily detectable, when expressed, either by its presence, amount or activity. A reporter gene can encode or code for a fusion protein. In one embodiment, the fusion protein is encoded or coded by a heterologous gene that has readily detectable protein expression operably linked to the ORF encoding SMN. In a specific embodiment, the fusion protein comprises SMN encoded or coded by a nucleotide sequence without a stop codon and a protein encoded by a heterologous gene without the start codon that has readily detectable protein expression, such as luciferase. In another embodiment, the fusion protein is encoded or coded by a heterologous gene that has readily detectable protein expression operably linked to the ORF encoding SMNΔEx7. In a specific embodiment, the fusion protein comprises SMNΔEx7 encoded or coded by a nucleotide sequence without the stop codon and a protein encoded by a heterologous gene without the start codon that has readily detectable protein expression, such as luciferase. In a specific embodiment, a reporter gene comprises a first nucleotide sequence encoding or coding for a protein that is readily detectable and is operably linked to a second nucleotide sequence encoding a peptide or protein, wherein the first and second nucleotide sequences not found in nature to be linked to each other (e.g., a second nucleotide sequence that is heterologous to the first nucleotide sequence).

Reporter genes may be obtained and the nucleotide sequence of the reporter gene determined by any method well-known to one of skill in the art. The nucleotide sequence of a reporter gene can be obtained, e.g., from the literature or a database such as GenBank. Alternatively, a polynucleotide encoding a reporter gene may be generated from nucleic acid from a suitable source. If a clone containing a nucleic acid encoding a particular reporter gene is not available, but the sequence of the reporter gene is known, a nucleic acid encoding the reporter gene may be chemically synthesized or obtained from a suitable source (e.g., a cDNA library, or a cDNA library generated from, or nucleic acid, preferably poly A+ RNA, isolated from, any tissue or cells expressing a reporter protein from the reporter gene) by PCR amplification. Once the nucleotide sequence of a reporter gene is determined, the nucleotide sequence of the reporter gene may be manipulated using methods well-known in the art for the manipulation of nucleotide sequences (e.g., recombinant DNA techniques, site directed mutagenesis, PCR, etc.) to generate reporter genes having a different amino acid sequence, for example to create amino acid substitutions, deletions, and/or insertions.

Examples of reporter genes include, but are not limited to, nucleotide sequences encoding or coding for luciferase (e.g., firefly luciferase, renilla luciferase, and click beetle luciferase), green fluorescent protein ("GFP") (e.g., green fluorescent protein, yellow fluorescent protein, red fluorescent protein, cyan fluorescent protein, and blue fluorescent protein), beta-galactosidase ("b-gal"), beta-glucoronidase, beta-lactamase, chloramphenicol acetyltransferase ("CAT"), and alkaline phosphatase ("AP"). The characteristics and methods for using the aforementioned reporter genes are known to one of skill in the art. In one embodiment, a reporter gene utilized in the nucleic acid constructs is easily assayed and has an activity which is not normally found in the cell or organism of interest. In another embodiment, a reporter gene utilized in the nucleic acid constructs is not SMN1, SMN2, or a nucleotide sequence encoding or coding for either or both SMN or SMNΔEx7 protein.

Cells and Transfection Techniques

A host cell may be transformed or transfected with the nucleic acid construct described herein. In certain embodiments, the use of stable transformants is preferred. In one embodiment, the host cell is a mammalian cell. In another embodiment, the host cell is a human cell. In another embodiment, the host cells are primary cells isolated from a tissue or other biological sample of interest. Host cells that can be used in the methods of the present invention include, but are not limited to, hybridomas, pre-B cells, 293 cells, 293T cells, 293H cells, HeLa cells, HepG2 cells, K562 cells, 3T3 cells, MCF7 cells, SkBr3 cells, BT474 cells, RD cells, A204 cells, or neuroblastoma cells lines such as MC-IXC, SK-N-MC, SK-N-MC, SK-N-DZ, SH-SY5Y, and BE(2)-C. In one embodiment, the host cells are immortalized cell lines derived from a source, e.g., a tissue, specific to SMN. In another embodiment, the host cells are fetal/embryonic cells. In yet another embodiment, the host cells are from an adult. In another embodiment, the host cells are stem cells. In a specific embodiment, the host cells are embryonic stem cells. Other host cells that can be used in the present invention include, but are not limited to, bacterial cells, yeast cells, virally-infected cells, or plant cells.

Transformation may be by any known method for introducing polynucleotides into a host cell, for example by packaging the polynucleotide in a virus and transducing a host cell with the virus, and by direct uptake of the polynucleotide. The transformation procedure used depends upon the host to be transformed. Such methods are well-known to one of skill in the art.

In one embodiment, stable cell lines expressing a reporter protein via a nucleic acid construct of interest are generated for high throughput screening. Such stable cells lines may be generated by introducing a nucleic acid construct further comprising a selectable marker, allowing the cells to grow for 1-2 days in an enriched medium, and then growing the cells on a selective medium. The selectable marker in the recombinant plasmid confers resistance to the selection and allows cells to stably integrate the plasmid into their chromosomes and grow to form foci which in turn can be cloned and expanded into cell lines.

In some embodiments, a host cell contains a vector comprising a nucleic acid construct, wherein the nucleic acid construct comprises a reporter gene operably linked to (i) the 5'-UTR of SMN or a fragment, mutant or post-transcriptional regulatory element thereof and a 3'-UTR of SMN or a fragment, mutant or post-transcriptional regulatory element thereof; (ii) the 5'-UTR of SMN or a fragment, mutant or post-transcriptional regulatory element thereof; or (iii) the 3'-UTR of SMN or a fragment, mutant or post-transcriptional regulatory element thereof, and wherein the 5'-UTR is 5' (upstream) of the reporter gene and the 3'-UTR is 3' (downstream) of the reporter gene.

Cell Free Extracts

The invention provides for the translation of the nucleic acid constructs in a cell-free system. Techniques for practicing this specific aspect of this invention will employ, unless otherwise indicated, conventional techniques of molecular biology, microbiology, and recombinant DNA manipulation and production, which are routinely practiced by one of skill in the art. Any technique well-known to one of skill in the art may be used to generate cell-free extracts for translation in vitro (otherwise referred to herein as a cell-free extract). For example, the cell-free extracts for in vitro translation reactions can be generated by centrifuging cells and clarifying the supernatant.

The cell-free translation extract may be isolated from cells of any species origin. For example, the cell-free translation extract may be isolated from human cells (e.g., HeLA cells, RD cells, A204 cells), 293 cells, Vero cells, yeast, mouse cells (e.g., cultured mouse cells), rat cells (e.g., cultured rat cells), Chinese hamster ovary (CHO) cells, Xenopus oocytes, rabbit reticulocytes, primary cells, cancer cells (e.g., undifferentiated cancer cells), cell lines, wheat germ, rye embryo, or bacterial cell extract. In a specific embodiment, the cells from which the cell-free extract is obtained do not endogenously express SMN or SMNΔEx7. In another embodiment, the cell-free extract is an extract isolated from human cells. In a further embodiment, the human cells that can be used in the methods of the present invention, include, but are not limited to HeLa cells, 293 cells, 293T cells, 293H cells, HeLa cells, HepG2 cells, K562 cells, 3T3 cells, MCF7 cells, SkBr3 cells, BT474 cells, MC-IXC cells, SK-N-MC cells, SK-N-MC cells, SK-N-DZ cells, SH-SY5Y cells, or BE(2)C.

Screening Assays
Cell-Based Assays

Host cells transformed or transfected with the nucleic acid construct described herein may be used to screen, identify or validate compounds that modulate post-transcriptional or UTR-dependent expression of SMN. In one embodiment, the cells are stably transfected with the nucleic acid construct. In a specific embodiment, the invention provides a method for identifying or validating a compound that modulates the post-transcriptional or UTR-dependent expression of SMN, comprising (a) contacting a host cell expressing a reporter protein via a nucleic acid construct described herein; and (b) detecting the amount or activity of the reporter protein, wherein a compound that modulates the post-transcriptional or UTR-dependent expression of SMN is identified or validated if the compound alters the amount or activity of the reporter protein detected relative to a previously determined reference range, or relative to the amount or activity of the reporter protein detected in the absence of the compound or the presence of a negative control.

In one embodiment, the assays for identifying or validating compounds that modulate the post-transcriptional expression of SMN may be conducted by: (a) contacting a compound with a host cell engineered to express a reporter protein via a nucleic acid construct comprising a reporter gene encoding or coding for the reporter protein operably linked to any of the 5'-UTR and 3'-UTR, the 5'-UTR or the 3'-UTR of SMN, or a fragment, mutant or post-transcriptional regulatory element thereof, wherein the 5'-UTR is upstream of the reporter gene and the 3'-UTR is downstream of the reporter gene; and (b) measuring the expression of said reporter protein. In some embodiments, the nucleic acid construct comprises a reporter gene operably linked to the 5'-UTR of SMN and a 3'-UTR unrelated to SMN, wherein the 5'-UTR of SMN is upstream of the reporter gene and the 3'-UTR is downstream of the reporter gene. In some embodiments, the nucleic acid construct comprises a reporter gene operably linked to a 5'-UTR unrelated to SMN and the 3'-UTR of SMN, wherein the 5'-UTR is upstream of the reporter gene and the 3'-UTR of SMN is downstream of the reporter gene.

An alteration in the amount or activity of a reporter protein detected in the presence of a compound relative to a previously determined reference range, or relative to the amount or activity of the reporter protein detected in the absence of the compound or the presence of a negative control in such assays indicates that a particular compound modulates UTR-dependent expression of the reporter gene, and thus may modulate UTR-dependent expression of the SMN gene. In one embodiment, a negative control (e.g., PBS, DMSO or another agent that is known to have no effect on the expression of the reporter gene) and a positive control (e.g., an agent that is known to have an effect on the expression of the reporter gene, preferably an agent that affects untranslated region-dependent expression) are included in the cell-based assays described herein.

Accordingly, the present invention is directed to a method for identifying or validating a compound that modulates UTR-dependent expression of SMN comprising: (a) contacting a compound with a host cell containing a nucleic acid construct comprising a reporter gene operably linked to any of the 5'-UTR and 3'-UTR, the 5'-UTR or the 3'-UTR of SMN, or a fragment, mutant or post-transcriptional regulatory element thereof, wherein the 5'-UTR is upstream of the reporter gene and the 3'-UTR of SMN is downstream of the reporter gene; and (b) detecting the amount or activity of a reporter protein translated from a mRNA transcript transcribed from said reporter gene, wherein a compound that modulates UTR-dependent expression of SMN is identified or validated if the amount or activity of said reporter protein detected in the presence of the compound is altered relative to a previously determined reference range, or relative to the amount or relative to activity of said reporter protein detected in the absence of said compound or the presence of a negative control. In a specific embodiment, a compound that modulates UTR-dependent expression of SMN is identified or validated if the amount or activity of said reporter protein detected in the presence of the compound is up-regulated relative to a previously determined reference range, or relative to the amount or activity of said reporter protein detected in the absence of said compound or the presence of a negative control. In a specific embodiment, the previously determined reference range is the amount or activity of said reporter protein detected in the presence of a negative control (e.g., PBS or DMSO).

The step of contacting a compound with a host cell expressing or genetically engineered to express a reporter protein via a nucleic acid construct comprising a reporter gene encoding or coding for said reporter protein operably linked to any of the 5'-UTR and 3'-UTR, the 5'-UTR or the 3'-UTR of SMN, or a fragment, mutant or post-transcriptional regulatory element thereof may be conducted under physiologic conditions. In a specific embodiment, a compound is contacted with the host cells in the presence of an aqueous solution. In accordance with this embodiment, the aqueous solution may comprise a buffer and a combination of salts, preferably approximating or mimicking physiologic conditions. Alternatively, the aqueous solution may comprise a buffer, a combination of salts, and a detergent or a surfactant. Examples of salts which may be used in the aqueous solution include, but not limited to, KCl, NaCl, and/or $MgCl_2$. The optimal concentration of each salt used in the aqueous solution is dependent on the host cells and compounds used and can be determined using routine experimentation.

The invention provides for contacting a compound with a host cell expressing or genetically engineered to express a reporter protein via a nucleic acid construct comprising a reporter gene encoding or coding for said reporter protein operably linked to any of the 5'-UTR and 3'-UTR, the 5'-UTR or the 3'-UTR of SMN, or a fragment, mutant or post-transcriptional regulatory element thereof for a specific period of time. For example, the contacting can take place for about 1 minute, 2 minutes, 3 minutes, 4, minutes, 5, minutes, 10 minutes, 15 minutes, 20 minutes, 30 minutes, 1 hour, 2 hours, 3 hours, 4 hours, 5 hours, 10 hours, 15 hours, 20 hours, 1 day, 2 days, 3 days, 4 days, 5 days, or 1 week. In one embodiment, the contacting is about 15 hours, i.e., overnight. The contacting can take place for about 1 minute to 1 week, preferably about 5 minutes to 5 days, more preferably about 10 minutes to 2 days, and even more preferably about 1 hour to 1 day.

In one embodiment, the invention provides a method for identifying or validating a compound that modulates UTR-dependent expression of SMN, said method comprising: (a) engineering a host cell to express a reporter protein via a nucleic acid construct comprising a reporter gene encoding or coding for said reporter protein operably linked to the any of the 5'-UTR and 3'-UTR, the 5'-UTR or the 3'-UTR of SMN or a fragment, mutant or post-transcriptional regulatory element thereof in a cell, wherein the 5'-UTR is upstream of the reporter gene and the 3'-UTR of SMN is downstream of the reporter gene; (b) contacting said cell with a compound; and (c) detecting the amount or activity of said reporter protein, wherein a compound that modulates UTR-dependent expression SMN is identified if the amount or activity of said reporter protein detected in the presence of the compound is altered relative to a previously determined reference range or relative to the amount or activity of said reporter protein detected in the absence of said compound or the presence of a negative control (e.g., phosphate buffered saline ("PBS") or dimethyl sulfoxide ("DMSO")). In a specific embodiment, the previously determined reference range is the amount or activity of said reporter protein detected in the presence of a negative control (e.g., PBS or DMSO).

In another embodiment, the invention provides a method for identifying or validating a compound that modulates UTR-dependent expression of SMN, said method comprising: (a) contacting a compound with a host cell expressing a reporter protein via a nucleic acid construct comprising a reporter gene encoding or coding for said reporter protein operably linked to any of the 5'-UTR and 3'-UTR, the 5'-UTR or the 3'-UTR of SMN, or a fragment, mutant or post-transcriptional regulatory element thereof, wherein the 5'-UTR is upstream of the reporter gene and the 3'-UTR of SMN is downstream of the reporter gene; and (b) detecting the amount or activity of said reporter protein, wherein a compound that modulates UTR-dependent expression of SMN is identified or validated if the amount or activity of said reporter protein detected in the presence of the compound is altered relative to a previously determined reference range or relative to the amount or activity of said reporter protein detected in the absence of said compound or the presence of a negative control (e.g., PBS or DMSO). In a specific embodiment, the previously determined reference range is the amount or activity of said reporter protein in the presence of a negative control (e.g. PBS or DMSO).

In another embodiment, the invention provides a method for identifying or validating a compound that increases, enhances, or upregulates UTR-dependent expression of SMN, said method comprising (a) contacting a compound with a host cell expressing a reporter protein via a nucleic acid construct comprising a reporter gene encoding or coding for said reporter protein operably linked to any of the 5'-UTR and 3'-UTR, the 5'-UTR or the 3'-UTR of SMN, or a fragment, mutant or post-transcriptional regulatory element thereof, wherein the 5'-UTR is upstream of the reporter gene and the 3'-UTR of SMN is downstream of the reporter gene; and (b) detecting the amount or activity of said reporter protein, wherein a compound that increases, enhances, or upregulates UTR-dependent expression of SMN is identified or validated if the amount or activity of said reporter protein detected in the presence of the compound is increased relative to a previously determined reference range, or relative to the amount or activity of said reporter protein detected in the absence of the compound or the presence of a negative control (e.g., PBS or DMSO). In a specific embodiment, the previously determined reference range is the amount or activity of said reporter protein detected in the presence of a negative control (e.g., PBS or DMSO). In certain embodiments, the increase in the amount or activity of said reporter protein is at least 1.5 fold, 2 fold, 3 fold, 4 fold, 5 fold, 6 fold, 7 fold, 8 fold, 9 fold, or 10 fold greater than the amount of activity of said reporter protein detected in the absence of the compound or in the presence of a negative control. In a specific embodiment, the amount or activity of said reporter protein are detected by the same technique when the host cell is contacted with the compound or a control (such as a negative control). In one embodiment, the technique is an immunological technique, such as an ELISA, western blot, etc.

The present invention provides methods of identifying environmental stimuli (e.g., exposure to different concentrations of $CO_2$ and/or $O_2$, stress and different pHs) that modulate UTR-dependent expression of SMN utilizing the cell-based assays described herein. In particular, the invention provides a method of identifying an environmental stimulus, said method comprising (a) contacting a host cell expressing a reporter protein via a nucleic acid comprising a reporter gene encoding or coding for said reporter protein operably linked to any of the 5'-UTR and 3'-UTR, the 5'-UTR or the 3'-UTR of SMN, or a fragment, mutant or post-transcriptional regulatory element thereof with an environmental stimulus; and (b) detecting the amount or activity of said reporter protein, wherein a compound that modulates UTR-dependent expression of SMN is identified if the amount or activity of said reporter protein detected in the presence of an environmental stimuli is altered relative to a previously determined reference range, or relative to the amount or activity of said reporter protein detected in the absence of the compound or the presence of a negative control (e.g., PBS or DMSO). In a specific embodiment, the environmental stimuli does not include a compound.

The expression of a reporter protein in the cell-based reporter-gene assays may be detected by any technique well-known to one of skill in the art. Methods for detecting the expression of a reporter protein will vary with the reporter gene used. Assays for the various reporter genes are well-known to one of skill in the art. For example, as described herein, luciferase, beta-galactosidase ("β-gal"), beta-glucoronidase ("GUS"), beta-lactamase, chloramphenicol acetyltransferase ("CAT"), and alkaline phosphatase ("AP") are enzymes that can be analyzed in the presence of a substrate and could be amenable to high throughput screening. For example, the reaction products of luciferase, beta-galactosidase ("β-gal"), and alkaline phosphatase ("AP") are assayed by changes in light imaging (e.g., luciferase), spectrophotometric absorbance (e.g., b-gal), or fluorescence (e.g., AP). Assays for changes in light output, absorbance, and/or fluorescence are easily adapted for high throughput screening. For example, b-gal activity can be measured with a microplate reader. Green fluorescent protein ("GFP") activity can be measured by changes in fluorescence. For example, in the case of mutant GFPs that fluoresce at 488 nm, standard fluorescence activated cell sorting ("FACS") equipment can be used to separate cells based upon GFP activity.

Alterations in the expression of a reporter protein may be determined by comparing the amount or activity of the reporter protein to a negative control (e.g., PBS, DMSO or another agent that is known to have no effect on the expression of the reporter gene) and optionally, a positive control (e.g., an agent that is known to have an effect on the expression of the reporter gene, preferably an agent that effects untranslated region-dependent expression). Alternatively, alterations in the expression of a reporter protein may be determined by comparing the amount or activity of the reporter protein to a previously determined reference range.

Cell-Free Assays

A cell-free extract and the nucleic acid construct of the present invention may be used to screen, identify or validate compounds that modulate UTR-dependent expression of SMN. The invention provides a method for identifying or validating a compound that modulates UTR-dependent expression of SMN, comprising (a) contacting a compound with a nucleic acid construct described herein comprising a reporter gene and a cell-free extract; and (b) detecting the amount or activity of a reporter protein translated from said reporter gene, wherein a compound that modulates UTR-dependent expression of SMN is identified or validated if the amount or activity of said reporter protein detected in the presence of the compound is altered relative to a previously determined reference range, or the amount or activity of said reporter protein detected in the absence of the compound or the presence of a negative control (e.g., PBS or DMSO).

In one embodiment, the assays may be conducted to identify or validate a compound that modulates UTR-dependent expression of SMN in a cell-free manner by contacting a compound with a cell-free extract and a nucleic acid construct comprising a reporter gene operably linked to any of the 5'-UTR and 3'-UTR, the 5'-UTR or the 3'-UTR of SMN, or a fragment, mutant or post-transcriptional regulatory element thereof, wherein the 5'-UTR is upstream of the reporter gene and the 3'-UTR of SMN is downstream of the reporter gene, and measuring the amount or activity of the reporter protein translated from the reporter gene. The alteration in the amount or activity of the reporter protein detected in the presence of the compound relative to a previously determined reference range, or relative to the amount or activity or a reporter protein detected in the absence of a compound or the presence of a negative control in such assays indicates that a particular compound modulates UTR-dependent expression of SMN. In one embodiment, a negative control (e.g., PBS, DMSO or another agent that is known to have no effect on the expression of the reporter gene) and a positive control (e.g., an agent that is known to have an effect on the expression of the reporter gene, preferably an agent that effects untranslated region-dependent expression) are included in the cell-free assays described herein. In a specific embodiment, the previously determined reference range is the amount or activity of said reporter protein in the presence of a negative control (e.g., PBS or DMSO).

Typically, the nucleic acid construct used in the cell-free assay is a RNA transcript (e.g., mRNA or pre-mRNA) that has been produced using, e.g., in vitro run-off transcription. For example, a RNA can be made in run-off transcription of a linearized form of a nucleic acid construct that is DNA which contains a bacteriophage promoter, a reporter gene and any of the 5'-UTR and 3'-UTR, the 5'-UTR or the 3'-UTR of SMN, wherein the 5'-UTR is upstream and the 3'-UTR is downstream, and wherein the bacteriophage promoter drives transcription of said reporter gene. Bacteriophage promoters from a T3, SP6 or T7 bacteriophage or any other suitable promoter may be used together with the respective RNA polymerase derived from the corresponding bacteriophage. The present invention also provides nucleic acid constructs that may be prepared by in vitro run-off transcription.

The step of contacting a compound with a cell-free extract containing a nucleic acid construct comprising a reporter gene encoding or coding for said reporter protein operably linked to any of the 5'-UTR and 3'-UTR, the 5'-UTR or the 3'-UTR of SMN, or a fragment, mutant or post-transcriptional regulatory element thereof may be conducted under conditions approximating or mimicking physiologic conditions. In a specific embodiment, a compound is added to the cell-free extract in the presence of an aqueous solution. In accordance with this embodiment, the aqueous solution may comprise a buffer and a combination of salts, preferably approximating or mimicking physiologic conditions. Alternatively, the aqueous solution may comprise a buffer, a combination of salts, and a detergent or a surfactant. Examples of salts which may be used in the aqueous solution include, but not limited to, KCl, NaCl, and/or $MgCl_2$. The optimal concentration of each salt used in the aqueous solution is dependent on the cell-free extract and compounds used and can be determined using routine experimentation.

The invention provides for contacting a compound with a cell-free extract containing a nucleic acid construct comprising a reporter gene encoding or coding for said reporter protein operably linked to any of the 5'-UTR and 3'-UTR, the 5'-UTR or the 3'-UTR of SMN, or a fragment, mutant or post-transcriptional regulatory element thereof for a specific period of time. For example, the contacting can take place for about 1 minute, 2 minutes, 3 minutes, 4, minutes, 5, minutes, 10 minutes, 15 minutes, minutes, 30 minutes, 1 hour, 2 hours, 3 hours, 4 hours, 5 hours, 10 hours, 15 hours, 20 hours, 1 day, 2 days, 3 days, 4 days, 5 days, or 1 week. In one embodiment, the contacting is about 15 hours, i.e., overnight. The contacting can take place for about 1 minute to 1 week, preferably about 5 minutes to 5 days, more preferably about 10 minutes to 2 days, and even more preferably about 1 hour to 1 day.

In a specific embodiment, the invention provides a method for identifying or validating a compound that modulates untranslated region-dependent expression of SMN, said method comprising: (a) contacting a compound with a cell-free extract and a nucleic acid construct comprising a reporter gene operably linked to any of the 5'-UTR and 3'-UTR, the 5'-UTR or the 3'-UTR of SMN, or a fragment, mutant or post-transcriptional regulatory element thereof, wherein the 5'-UTR is upstream of the reporter gene and the 3'-UTR of SMN is downstream of the reporter gene; and (b) detecting the amount or activity of a reporter protein translated from said reporter gene, wherein a compound that modulates UTR-dependent expression of SMN is identified or validated if the amount or activity of said reporter protein detected in the presence of the compound is altered relative to a previously determined reference range, or relative to the amount or activity of said reporter protein detected in the absence of the compound or the presence of a negative control (e.g., PBS or DMSO).

In a specific embodiment, the invention provides a method for identifying or validating compounds that increase, enhance or upregulate UTR-dependent expression of SMN, said method comprising (a) contacting a compound with a cell-free extract and a RNA (e.g., a mRNA) comprising a reporter gene operably linked to any of the 5'-UTR and 3'-UTR, the 5'-UTR or the 3'-UTR of SMN mRNA, or a fragment, mutant or post-transcriptional regulatory element thereof, wherein the 5'-UTR is upstream of the reporter gene and the 3'-UTR of SMN is downstream of the reporter gene; and (b) detecting the amount or activity of a reporter protein translated from said reporter gene, wherein a compound that increases, enhances, or up-regulates UTR-dependent expression of SMN is identified or validated if the amount or activity of said reporter protein detected in the presence of the compound is increased relative to a previously determined reference range, or relative to the amount or activity of said reporter protein detected in the absence of the compound or the presence of a control (e.g., PBS or DMSO).

In a specific embodiment, the invention provides a method of increasing or enhancing UTR-dependent expression of SMN, said method comprising (a) contacting a compound with a cell-free extract and a nucleic acid construct comprising a reporter gene operably linked to any of the 5'-UTR and 3'-UTR, the 5'-UTR or the 3'-UTR of SMN, or a fragment, mutant or post-transcriptional regulatory element thereof, wherein the 5'-UTR is upstream of the reporter gene and the 3'-UTR of SMN is downstream of the reporter gene; and (b) detecting the amount or activity of a reporter protein translated from said reporter gene, wherein a compound that increases, enhances, or upregulates UTR-dependent expression of SMN is identified or validated if the amount or activity of said reporter protein detected in the presence of the compound is increased relative to a previously determined reference range, or relative to the amount or activity of said reporter protein detected in the absence of the compound or the presence of a control (e.g., PBS or DMSO). In one embodiment, the nucleic acid construct is RNA. In a specific embodiment, the previously determined reference range is the amount or activity of said reporter protein in the presence of a negative control (e.g., PBS or DMSO).

In a specific embodiment, the invention provides a method for identifying or validating compounds that modulates UTR-dependent expression of SMN, said method comprising (a) contacting a compound with a cell-free extract and a RNA (e.g., a mRNA) comprising a reporter gene operably linked to any of the 5'-UTR and 3'-UTR, the 5'-UTR or the 3'-UTR of SMN mRNA, or a fragment, mutant or post-transcriptional regulatory element thereof, wherein the 5'-UTR is upstream of the reporter gene and the 3'-UTR of SMN is downstream of the reporter gene; and (b) detecting the amount or activity of a reporter protein translated from said reporter gene, wherein a compound that modulates UTR-dependent expression of SMN is identified or validated if the amount or activity of said reporter protein detected in the presence of the compound is altered relative to a previously determined reference range, or relative to the amount or activity of said reporter protein detected in the absence of the compound or the presence of a control (e.g., PBS or DMSO).

The activity of a compound in the in vitro extract can be determined by assaying the amount or activity of a reporter protein translated from a reporter gene, or alternatively, by quantifying the expression of the reporter gene by, for example, labeling the in vitro translated protein (e.g., with $^{35}$S-labeled methionine), or by immunological methods, such as western blot analysis or immunoprecipitation. Such methods are well-known to one of skill in the art.

Direct Binding Assays

Compounds that modulate UTR-dependent expression of SMN can be identified by direct binding assays, such as those known to one of skill in the art. Briefly, direct binding assays may be conducted by attaching one or more compounds to solid supports, e.g., polymer beads, with each solid support having substantially one type of compound attached to its surface. The plurality of solid supports is exposed in aqueous solution to SMN having a detectable label, forming a dye-labeled target RNA:support-attached compound complex wherein the SMN mRNA transcript or RNA transcript comprising any of the 5'-UTR and 3'-UTR, the 5'-UTR or the 3'-UTR of SMN mRNA, or a fragment, mutant or post-transcriptional regulatory element thereof. Binding of a target RNA molecule to a particular compound labels the solid support, e.g., bead, comprising the compound, which can be physically separated from other, unlabeled solid supports. Alternatively, the compound and not the target RNA is labeled, and the target RNA is attached to a solid support.

Direct binding assays may be conducted by contacting a target RNA having a detectable label with a compound free in solution, in labeled tubes or microtiter wells, or a microarray wherein the target RNA is selected from a SMN mRNA transcript or RNA transcript comprising any of the 5'-UTR and 3'-UTR, the 5'-UTR or the 3'-UTR of SMN, or a fragment, mutant or post-transcriptional regulatory element thereof. Alternatively, the compound and not the target RNA is labeled.

Binding assays, including direct binding assays, can also be used to detect the interaction between compounds and proteins that regulate the post-transcriptional expression of SMN. Briefly, direct binding assays may be conducted by attaching one or more compounds to a solid support, e.g., polymer beads, with each solid support having substantially one type of compound attached to its surface. The plurality of solid supports is exposed in aqueous solution to a target protein having a detectable label, forming a dye-labeled target protein:support-attached compound complex, wherein the target protein is a protein that modulates UTR-mediated expression of SMN. Alternatively, the compound is labeled and the target protein is attached to a solid support. Similar to the assays above with RNA, the interaction between a target protein and a compound can be conducted in solution.

Identification and Validation of Compounds

Using embodiments of the screening assays described herein, the inventors have identified or validated compounds for their effect on UTR-dependent expression of SMN. Further, any compound of interest can be tested for its ability to modulate UTR-dependent expression of SMN using the screening assays described herein.

In one embodiment, a compound that modulates UTR-dependent expression of SMN binds directly to any of the 5'-UTR and 3'-UTR, the 5'-UTR or the 3'-UTR of SMN, or a fragment, mutant or post-transcriptional regulatory element thereof. In another embodiment, a compound that modulates UTR-dependent expression of SMN, does not bind directly to any of the 5'-UTR and 3'-UTR, the 5'-UTR or the 3'-UTR of SMN, or a fragment, mutant or post-transcriptional regulatory element thereof. In another embodiment, a compound that modulates UTR-dependent expression of SMN binds to a protein that modulates UTR-dependent expression of SMN. In yet another embodiment, a compound that modulates UTR-dependent expression of SMN mRNA binds to a nucleotide regulatory sequence of a gene that encodes a protein that modulates UTR-dependent expression of SMN.

In a specific embodiment, a compound is an antisense oligonucleotide, which is a nucleotide sequence complementary to a specific DNA or RNA sequence described herein. Antisense oligonucleotides can be deoxyribonucleotides, ribonucleotides, or a combination of both. Nucleic acid molecules including antisense oligonucleotide molecules, can be provided in a DNA construct and introduced into a cell. In another embodiment, a compound is an interfering RNA (RNAi) or microRNA (miRNA). RNAi comprises dsRNA that inhibits the expression of genes with complementary nucleotide sequences. In one embodiment, the dsRNA is 20-25 residues in length, termed small interfering RNAs (siRNA).

In order to exclude the possibility that a particular compound is functioning solely by modulating the expression of SMN in a UTR-independent manner, one or more mutations may be introduced into an untranslated region(s) operably linked to a reporter gene and the effect on the expression of the reporter gene in an assay as described herein can be determined. For example, a nucleic acid construct comprising the 5'-UTR of SMN may be mutated by deleting a fragment of the 5'-UTR of SMN or substituting a fragment of the 5'-UTR of SMN with a fragment of the 5'-UTR of another gene and measuring the expression of the reporter gene in the presence and absence of a compound that has been identified or validated in an instant screening assay as described herein. If the deletion of a fragment of the 5'-UTR of SMN or the substitution of a fragment of the 5'-UTR of SMN with a fragment of the 5'-UTR of another gene affects the ability of the compound to modulate the expression of the reporter gene, then the fragment of the 5'-UTR that is deleted or substituted plays a role in the regulation of the reporter gene expression and the regulation, at least in part, is in an untranslated region-dependent manner.

The possibility that a particular compound functions solely by modulating the expression of SMN in an UTR-independent manner may be also determined by changing the vector utilized as a nucleic acid construct. The untranslated regions flanked by a reporter gene from the nucleic acid construct in which an effect on reporter gene expression was detected following exposure to a compound may be inserted into a new nucleic acid construct that has, e.g., different transcriptional regulation elements (e.g., a different promoter) and a different selectable marker. The level of reporter gene expression in the presence of the compound can be compared to the level of reporter gene expression in the absence of the compound or in the presence of a control (e.g., PBS or DMSO). If there is no change in the level of expression of the reporter gene in the presence of the compound relative to the absence of the compound or in the presence of a control, then the compound may be functioning in an untranslated region-independent manner.

The specificity of a particular compound's effect on untranslated region-dependent expression of SMN can also be determined. In particular, the effect of a particular compound on the expression of one or more genes (preferably, a plurality of genes) can be determined utilizing assays well known to one of skill in the art or described herein. In one embodiment, the specificity of a particular compound for an untranslated region of SMN mRNA is determined by (a) contacting the compound of interest with a host cell expressing a reporter protein via a nucleic acid construct comprising a reporter gene encoding said reporter protein operably linked to an UTR of a different gene (i.e., a gene different from SMN which has an UTR different from said SMN; and (b) detecting the amount or activity of said reporter protein, wherein the compound is specific for the untranslated region of SMN mRNA if the amount or activity of said reporter protein detected in the presence of the compound is not altered or is not substantially altered relative to a previously determined reference range, or relative to the amount or activity of said reporter protein detected in the absence of the compound or the presence of a negative control (e.g., PBS or DMSO).

In another embodiment, the specificity of a particular compound for an untranslated region of SMN mRNA is determined by (a) contacting the compound of interest with a panel of host cells, each host cell in a different well of a container (e.g., a 48- or 96-well plate) and each host cell expressing a reporter protein via a nucleic acid construct comprising a reporter gene operably linked to an UTR of a different gene which has an UTR different from SMN; and (b) detecting the amount or activity of a reporter protein, wherein the compound is specific for the untranslated region of SMN mRNA if the amount or activity of said reporter protein detected in the presence of the compound is not altered or is not substantially altered relative to a previously determined reference range, or relative to the amount or activity of said reporter protein detected in the absence of the compound or the presence of a negative control (e.g., PBS or DMSO). In accordance with this embodiment, the panel may comprise 5, 7, 10, 15, 20, 25, 50, 75, 100 or more cells.

In another embodiment, the specificity of a particular compound for an untranslated region of SMN mRNA is determined by (a) contacting the compound of interest with a cell-free extract and a nucleic acid construct comprising a reporter gene operably linked to an UTR of a different gene; and (b) detecting the amount or activity of a reporter protein translated from the reporter gene, wherein the compound is specific for the untranslated region of said SMN mRNA if the amount or activity of said reporter protein detected in the presence of the compound is not altered or is not substantially altered relative to a previously determined reference range, or relative to the amount or activity of said reporter protein detected in the absence of the compound or the presence of a negative control (e.g., PBS or DMSO).

In certain embodiments, the term "not substantially altered" means that the compound alters the expression of the reporter gene or SMN1 or SMN2 by less than 20%, less than 15%, less than 10%, less than 5%, or less than 2% relative to a negative control such as PBS or DMSO. In some embodiments, the term "not substantially altered" means that the compound alters the expression of the reporter gene or SMN1 or SMN2 by less than 2 fold, less than 1.5 fold, less than 1 fold, less than 0.5 fold, less than 0.2 fold, or less than 0.1 fold relative to a negative control such as PBS or DMSO. In a specific embodiment, the amount or activity of the reporter protein is detected by the same technique whether a compound or a control is used in an assay described herein, such as immunological techniques, e.g., flow cytometry, ELISA or Western blot.

The compounds identified or validated in the assays described supra that modulate untranslated region-dependent expression of SMN can be further tested for untranslated region-dependent binding to any of the 5'-UTR and 3'-UTR, the 5'-UTR or the 3'-UTR of SMN, or a fragment or post-transcriptional regulatory element thereof. Furthermore, by assessing the effect of a compound on the expression of SMN, cis-acting elements, i.e., specific nucleotide sequences, that are involved in untranslated region-dependent expression may be identified. The compound can also be tested for binding to proteins and/or molecules involved in post-transcriptional expression of SMN. In one embodiment, the proteins and/or molecules involved in post-transcriptional expression of SMN bind to cis-acting elements in any of the 5'-UTR and 3'-UTR, the 5'-UTR or the 3'-UTR of SMN.

RNA Binding Assays

Compounds that modulate untranslated region-dependent expression of SMN can be tested for binding to any of the 5'-UTR and 3'-UTR, the 5'-UTR or the 3'-UTR of SMN, or a fragment or post-transcriptional regulatory element thereof by any method known in the art.

Subtraction Assay

The element(s) of an untranslated region(s) that is (are) necessary for a compound identified in accordance with the methods described herein to modulate untranslated region-dependent expression of SMN can be determined utilizing standard mutagenesis techniques well-known to one of skill in the art. One or more mutations (e.g., deletions, additions and/or substitutions) may be introduced into an untranslated region(s) operably linked to a reporter gene and the effect on the expression of the reporter gene in an assay as described herein can be determined. For example, a nucleic acid construct comprising the 5'-UTR of SMN may be mutated by deleting a fragment or all of the 5'-UTR of SMN or substituting a fragment of the 5'-UTR of SMN with a fragment of the 5'-UTR of another gene and measuring the expression of the reporter gene in the presence and absence of a compound that has been identified in an instant screening assay described herein. If the deletion of a fragment of the 5'-UTR of SMN or the substitution of a fragment of the 5'-UTR of SMN with a fragment of the 5'-UTR of another gene affects the ability of the compound to modulate the expression of the reporter gene, then the fragment of the 5'-UTR deleted or substituted plays a role in the regulation of the reporter gene expression.

Standard techniques known to those of skill in the art can be used to introduce mutations in the nucleotide sequence of an untranslated region of SMN, including, for example, site-directed mutagenesis and PCR-mediated mutagenesis. In a specific embodiment, less than 75 nucleic acid residue substitutions, less than 50 nucleic acid residue substitutions, less than 45 nucleic acid residue substitutions, less than 40 nucleic acid residue substitutions, less than 35 nucleic acid residue substitutions, less than 30 nucleic acid residue substitutions, less than 25 nucleic acid residue substitutions, less than 20 nucleic acid residue substitutions, less than 15 nucleic acid residue substitutions, less than 10 nucleic acid residue substitutions, or less than 5 nucleic acid residue substitutions are introduced into the nucleotide sequence of an untranslated region of SMN. In another embodiment, less than 10 elements of an untranslated region of SMN, less than 9 elements of an untranslated region of SMN, less than 8 elements of an untranslated region of SMN, less than 7 elements of an untranslated region of SMN, less than 6 elements of an untranslated region of SMN, less than 5 elements of an untranslated region of SMN, less than 4 elements of an untranslated region of SMN, less than 3 elements of an untranslated region of SMN, or less than 2 elements of an untranslated region of SMN are mutated at one time.

Assays for Detecting the Expression and Activity of Proteins Encoded by SMN

Compounds identified or validated in the assays described herein that modulate untranslated region-dependent expression may be further tested in various in vitro assays (e.g., cell-free assays) or in vivo assays (e.g., cell-based assays) well-known to one of skill in the art or as described herein to determine the effect of said compounds on the expression of SMN from which the untranslated regions of the nucleic acid construct are derived. The specificity of a particular compound's effect on untranslated region-dependent expression of one or more other genes can also be determined utilizing assays well-known to one of skill in the art or described herein.

The expression of the gene products of SMN can be readily detected, e.g., by quantifying the protein and/or RNA encoded by said gene. Many methods standard in the art can be thus employed, including, but not limited to, immunoassays to detect and/or visualize protein expression (e.g., Western blot, immunoprecipitation followed by sodium dodecyl sulfate polyacrylamide gel electrophoresis (SDS-PAGE), immunocytochemistry, etc.) and/or hybridization assays to detect gene expression by detecting and/or visualizing respectively mRNA encoding a gene (e.g., northern assays, dot blots, in situ hybridization, etc.). Such assays are routine and well known in the art. Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g. EDTA, PMSF, aprotinin, sodium vanadate), adding the antibody of interest to the cell lysate, incubating for a period of time (e.g., 1 to 4 hours) at 40° C., adding protein A and/or protein G Sepharose beads to the cell lysate, incubating for about an hour or more at 40° C., washing the beads in lysis buffer and resuspending the beads in SDS/sample buffer. The ability of the antibody of interest to immunoprecipitate a particular antigen can be assessed by, e.g., Western blot analysis. One of skill in the art would be knowledgeable as to the parameters that can be modified to increase the binding of the antibody to an antigen and decrease the background (e.g., pre-clearing the cell lysate with sepharose beads).

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), incubating the membrane with primary antibody (the antibody of interest) diluted in blocking buffer, washing the membrane in washing buffer, incubating the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise.

ELISAs generally comprise preparing antigen, coating the well of a 96-well microtiter plate with the antigen, adding the antibody of interest conjugated to a detectable agent such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable agent may be added to the well. Further, instead of coating the well with the antigen, the antibody may be coated to the well. In this case, a second antibody conjugated to a detectable agent may be added following the addition of the antigen of interest to the coated well. One of skill in the art would be knowledgeable as to the parameters that can be modified to increase the signal detected as well as other variations of ELISAs known in the art.

An increased level of either or both SMN or SMNΔEx7 protein indicates that the compound may be effective to treat SMA. Increased levels of target SMN or SMNΔEx7 protein in conjunction with no change in the levels of SMN indicate that the compound affects UTR-dependent expression of target protein and not promoter-dependent expression (transcription) of target RNA. Increased levels of target SMN or SMN-ΔEx7 protein in conjunction with increased levels of SMN RNA may indicate that the compound affects UTR-dependent expression of target protein and not promoter-dependent expression of target RNA (i.e., transcriptional regulation via the promoter/enhancer of SMN). Specific examples of cell culture models from patients with SMA may be used. Other cell culture models that may be used include, but are not limited to, 293H cells and RD cell cultures. The in vivo effect of the compound can also be assayed by performing immunofluorescence studies using antibodies against the SMN or SMNΔEx7 protein. Another antibody based separation that can be used to detect the protein of interest is the use of flow cytometry such as by a florescence activated cell sorter ("FACS").

A phenotyic or physiological readout can be used to assess untranslated region-dependent activity of SMN RNA in the presence and absence of the compound. In one embodiment, a phenotypic or physiological readout can be used to assess untranslated region-dependent activity of SMN RNA in the presence and absence of the compound. For example, SMN RNA may be overexpressed in a cell in which said SMN RNA is endogenously expressed. Where SMN RNA controls untranslated region-dependent expression of SMN, the in vivo effect of the compound can be assayed by quantifying the amount of protein and/or RNA encoded by said gene present in cells and/or biological samples obtained from a subject to which the compound was administered.

In addition to measuring the effect of a compound identified in the reporter gene-based assays described herein on the expression of SMN from which each UTR of the nucleic acid construct were derived, the activity of the protein encoded by SMN1 or SMN2 can be assessed utilizing techniques well-known to one of skill in the art. For example, the ability of a compound to affect the activity of SMN can be determined by assays that determine snRNP assembly efficiency since it has been demonstrated that SMN is required for snRNP assembly (see Yong et al., 2004. *Trends Cell Biol* 14:226-232). snRNP assembly can be assayed by any method known to those of skill in the art.

The activity of a protein encoded by SMN1 or SMN2 mRNA can be, e.g., determined by detecting induction of a cellular second messenger (e.g., intracellular $Ca^{2+}$, diacylglycerol, $IP_3$, etc.), detecting the phosphorylation of a protein, detecting the activation of a transcription factor, or detecting a cellular response, for example, cellular differentiation, or cell proliferation. The induction of a cellular second messenger or phosphorylation of a protein can be determined by, e.g., immunoassays well-known to one of skill in the art and described herein. The activation of a transcription factor can be detected by, e.g., electromobility shift assays, and a cellular response such as cellular proliferation can be detected by, e.g., trypan blue cell counts, $^3$H-thymidine incorporation, and flow cytometry.

Secondary Screens of Compounds

Compounds identified or validated to modulate untranslated region-dependent expression of SMN may be tested for biological activity in further assays and/or animal models as described herein or known to those skilled in the art.

Cytotoxicity and Cell Proliferation Assays

In some embodiments, compounds are tested for cytotoxicity in mammalian, preferably human, cell lines. In certain embodiments, cytotoxicity is assessed in one or more of the following non-limiting examples of cell lines: RD (a human muscle cell line); A204 (a human rhabdomyosarcoma cell line); U937 (a human monocyte cell line); primary peripheral blood mononuclear cells (PBMC); Huh7 (a human hepatoblastoma cell line); 293, 293T or 293H (a human embryonic kidney cell line); THP-1 (monocytic cells); a HeLa cell line; neuroblastoma cells lines (such as MC-IXC, SK-N-MC, SK-N-MC, SK-N-DZ, SH-SY5Y, and BE(2)-C).

Many assays well-known in the art can be used to assess viability of cells (infected or uninfected) or cell lines following exposure to a compound and, thus, determine the cytotoxicity of the compound. For example, cell proliferation can be assayed by measuring Bromodeoxyuridine (BrdU) incorporation, (3H) thymidine incorporation, by direct cell count, or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription. Cell viability can be assessed by using trypan-blue staining or other cell death or viability markers known in the art. In a specific embodiment, the level of cellular ATP is measured to determined cell viability.

In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes may include enlargement, granularity, cells with ragged edges, a filmy appearance, rounding, detachment from the surface of the well, or other changes. These changes are given a designation of T (100% toxic), PVH (partially toxic-very heavy-80%), PH (partially toxic-heavy-60%), P (partially toxic-40%), Ps (partially toxic-slight-20%), or 0 (no toxicity-0%), conforming to the degree of cytotoxicity seen. A 50% cell inhibitory (cytotoxic) concentration ($IC_{50}$) is determined by regression analysis of these data.

Compounds can be tested for in vivo toxicity in animal models. For example, animal models, described herein and/or others known in the art, used to test the effects of compounds on SMA can also be used to determine the in vivo toxicity of these compounds. For example, animals are administered a range of concentrations of compounds. Subsequently, the animals are monitored over time for lethality, weight loss or failure to gain weight, and/or levels of serum markers that may be indicative of tissue damage (e.g., creatine phosphokinase level as an indicator of general tissue damage, level of glutamic oxalic acid transaminase or pyruvic acid transaminase as indicators for possible liver damage). These in vivo assays may also be adapted to test the toxicity of various administration mode and/or regimen in addition to dosages.

The toxicity and/or efficacy of a compound in accordance with the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. A compound identified in accordance with the invention that exhibits large therapeutic indices is preferred. While a compound identified in accordance with the invention that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of a compound identified in accordance with the invention for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high-performance liquid chromatography.

Animal Model-Based Screens

Compounds identified in the reporter gene-based assay described herein can be tested for biological activity using animal models for SMA. These include animals engineered to contain SMN coupled to a functional readout system, such as a transgenic mouse. Such animal model systems include, but are not limited to, rats, mice, chicken, cows, monkeys, pigs, dogs, rabbits, etc. In a specific embodiment of the invention, a compound identified in accordance with the methods of the invention is tested in a mouse model system. Such model systems are widely used and well-known to the skilled artisan such as the SCID mouse model or transgenic mice.

The anti-SMA activity of a compound identified in accordance with the invention can be determined by administering the compound to an animal model and verifying that the compound is effective in reducing the severity of SMA in said animal model. Examples of animal models for SMA include, but are not limited to, SMA animal models described by Monani et al. (2000, *Human Molecular Genetics* 9 (16) 2451-2457) and Charlotte J. Sumner (2006, *NeuroRx* 3 (2):235-245), including a Drosophilia model in which there are several missense mutations in the SMN gene, a zebrafish model that was created by using morpholino antisense oligonucleotide knockdown technology to decrease the level of endogenous SMN protein to approximately 60%, a SMN double knockout mouse, mouse models that contain conditional knockout of exon 7 of the murine SMN gene in specific tissues using the Cre-LoxP system, and mouse models that expresses human SMN2 gene in the SMN knockout background. In a specific embodiment, a mouse model expresses a human SMN1 or SMN2 gene.

The ability of a compound or composition comprising a compound to treat can be assayed by assessing muscle strength, motor function, and pulmonary function in patients diagnosed with SMA. Muscle strength can be assessed by using any method known to those skilled in the art, including, but not limited to, use of a hand-held dynamometer. Muscle testing can be performed to assess right and left hand grip, right and left knee extension, right and left knee flexion, and right and left elbow flexion. Motor function can be assessed by a patient's ability to lie down, roll, sit, crawl, kneel, stand, walk, run, and jump. Pulmonary function tests can be performed on patients according to American Thoracic Society standards, and include, but are not limited to maximum inspiratory pressure, maximum expiratory pressure, cough pressure, forced vital capacity, forced expiratory volume in the first second, and measurement of lung volume.

Compositions

Any compound described herein may optionally be in the form of a composition comprising the compound. In certain embodiments provided herein, pharmaceutical compositions comprise an effective amount of a compound for up-regulating either or both SMN or SMNΔEx7 protein expression in an admixture with a pharmaceutically acceptable carrier, excipient, or diluent. The pharmaceutical compositions are suitable for veterinary and/or human administration. Accordingly, the present invention is directed to a method for treating SMA in a human subject in need thereof, comprising administering to the human subject an effective amount of such a pharmaceutical composition. In another embodiment, the present invention is directed to a use of one or more compounds that up-regulate either or both SMN or SMNΔEx7 protein expression for the preparation of a pharmaceutical composition for treating SMA in a human subject in need thereof.

The pharmaceutical compositions provided herein can be in any form that allows for the composition to be administered to a subject, said subject preferably being an animal, including, but not limited to a human, mammal, or non-human animal, such as a cow, horse, sheep, pig, fowl, cat, dog, mouse, rat, rabbit, guinea pig, etc., and is more preferably a mammal, and most preferably a human.

In a specific embodiment and in this context, the term "pharmaceutically acceptable carrier, excipient or diluent" means a carrier, excipient or diluent approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

Typical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to the way in which the dosage form will be administered to a patient and the specific active ingredients in the dosage form. The composition or single unit dosage form, if desired, can also contain minor amounts of wetting or emulsifying agents, or pH buffering agents. Further provided herein are anhydrous pharmaceutical compositions and dosage forms comprising one or more compounds of the present invention. The compositions and single unit dosage forms can take the form of solutions, suspensions, emulsion, tablets, pills, capsules, powders, sustained-release formulations and the like. Compositions provided herein are formulated to be compatible with the intended route of administration. Examples of routes of administration include, but are not limited to, parenteral, e.g., intravenous, intradermal, subcutaneous, oral (e.g., inhalation), intranasal, transdermal (topical), transmucosal, intra-synovial and rectal administration.

Pharmaceutical compositions provided herein that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art.

Typical oral dosage forms provided herein are prepared by combining a compound in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, microcrystalline cellulose, and mixtures thereof. Disintegrants that can be used in pharmaceutical compositions and dosage forms provided herein include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof. Lubricants that can be used in pharmaceutical compositions and dosage forms provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonSeed oil, sunflower oil, sesame oil, olive oil, corn oil, and soybean oil), zinc stearate, ethyl oleate, ethyl laureate, agar, and mixtures thereof.

A compound can be administered by controlled release means or by delivery devices that are well known to those of ordinary skill in the art. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. The invention thus encompasses single unit dosage forms suitable for oral administration such as, but not limited to, tablets, capsules, gelcaps, and caplets that are adapted for controlled release.

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. Transdermal, topical, and mucosal dosage forms provided herein include, but are not limited to, ophthalmic solutions, sprays, aerosols, creams, lotions, ointments, gels, solutions, emulsions, suspensions, or other forms known to one of skill in the art. Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

In certain specific embodiments, the compositions are in oral, injectable, or transdermal dosage forms. In one specific embodiment, the compositions are in oral dosage forms. In another specific embodiment, the compositions are in the form of injectable dosage forms. In another specific embodiment, the compositions are in the form of transdermal dosage forms.

Pharmaceutical Methods

The invention relates to a method for post-transcriptionally modulating the expression of SMN in a human subject in need thereof, comprising administering an effective amount of a compound to the subject, in which said compound enhances or upregulates in vitro or in cultured cells the post-transcriptional expression of a nucleic acid construct comprising a reporter gene operably linked to any of the 5'-UTR and 3'-UTR, the 5'-UTR or the 3'-UTR of SMN, wherein the 5'-UTR is upstream of the reporter gene and the 3'-UTR of SMN is downstream of the reporter gene. The present invention further relates to a method for treating SMA, in a human subject in need thereof, comprising administering an effective amount of a compound to the subject, in which said compound enhances or increases in vitro or in cultured cells the post-transcriptional expression of a nucleic acid construct comprising a reporter gene operably linked to any of the 5'-UTR and 3'-UTR, the 5'-UTR or the 3'-UTR of SMN, wherein the 5'-UTR is upstream of the reporter gene and the 3'-UTR of SMN is downstream of the reporter gene.

The present invention provides methods of treating SMA, in a human subject in need thereof, said methods comprising administering to the subject an effective amount of one or more compounds of the present invention. In specific embodiments, a compound is the only active ingredient administered to treat SMA. In a certain embodiment, a compound is the only active ingredient in a composition.

In some embodiments, a compound increases SMN or SMNΔEx7 protein expression by 5%, 10%, 15%, 20%, 25%, 35%, 45%, 50%, 55%, 65%, 70%, 75%, 80%, 85%, 90% or 95% relative to a negative control (e.g., PBS or 0.5-1.0% DMSO) as determined by the screening assays described herein or known in the art. In some embodiments, a compound that is administered to a subject increases SMN mRNA stability by about 5%, 10%, 15%, 20%, 25%, 35%, 45%, 50%, 55%, 65%, 70%, 75%, 80%, 85%, 90% or 95% relative to the negative control, as determined by mRNA stability assays (e.g., Northern blot or RT-PCR). In some embodiments, a compound that is administered increases SMN or SMNΔEx7 protein translation by 5%, 10%, 15%, 20%, 25%, 35%, 45%, 50%, 55%, 65%, 70%, 75%, 80%, 85%, 90% or 95% relative to a negative control as determined by assays known in the art, e.g., Western blotting, ELISA assay, flow cytometry.

In certain embodiments, the compound increases the amount or activity of a reporter protein or SMN or SMNΔEx7 protein by at least 1.5 fold, 2 fold, 3 fold, 4 fold, 5 fold, 6 fold, 7 fold, 8 fold, 9 fold, or 10 fold greater than the amount of activity of said reporter protein, SMN protein or SMNΔEx7 protein detected in the absence of the compound or in the presence of a negative control, as determined by an assay described herein or known in the art, e.g., ELISA, western blot, or FACs.

The effective amount of a compound used to enhance or increase the post-transcriptional expression of SMN depends on a number of factors, including but not limited to the type of SMA, health and age of the patient, and toxicity or side effects. The present invention encompasses methods for treating SMA for which no treatment is available. The present invention also encompasses methods for preventing, treating, and/or managing SMA as an alternative to other conventional therapies.

The present invention also provides methods of treating SMA to a subject in need thereof, said methods comprising administering to the subject one or more of the compounds of the present invention and one or more additional agents. In a specific embodiment, the other therapies are currently being used, have been used or are known to be useful in treating SMA. In another embodiment, one or more compounds are administered to a subject in combination with a supportive therapy, a pain relief therapy, or other therapy that does not have a therapeutic effect on SMA.

In some embodiments, a compound is administered to a subject suffering from SMA. In other embodiments, a compound is administered to a subject predisposed or susceptible to SMA. In some embodiments, a compound is administered to a subject with Type 0 SMA. In some embodiments, a compound is administered to a subject with Type 1 SMA. In other embodiments, a compound is administered to a subject with Type 2 SMA. In other embodiments, a compound is administered to a subject with Type 3 SMA. In some embodiments, a compound is administered to a subject with Type 4 SMA.

In certain embodiments, a compound is administered to a human that is 0 to 6 months old, 6 to 12 months old, 6 to 18 months old, 18 to 36 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, a compound is administered to a human infant. In other embodiments, a compound is administered to a human toddler. In other embodiments, a compound is administered to a human child. In other embodiments, a compound is administered to a human adult. In yet other embodiments, a compound is administered to an elderly human.

In certain embodiments, a compound is administered a subject in an immunocompromised state or immunosuppressed state or at risk for becoming immunocompromised or immunosuppressed. In certain embodiments, a compound is administered to a subject receiving or recovering from immunosuppressive therapy. In certain embodiments, a compound is administered to a subject that has or is at risk of getting cancer, AIDS, or a bacterial infection. In certain embodiments, the subject is, will or has undergone surgery, chemotherapy and/or radiation therapy. In certain embodiments, a compound is administered to a subject that has cystic fibrosis, pulmonary fibrosis or another condition affecting the lungs. In certain embodiments, a compound is administered to a subject that has, will have or had a tissue transplant.

In some embodiments, one or more compounds are administered to a patient who has proven refractory to therapies other than compounds, but are no longer on these therapies. In certain embodiments, the patient to be treated in accordance with the methods of this invention are patients already being treated with antibiotics, anti-virals, anti-fungals, or other biological therapy/immunotherapy. Among these patients are refractory patients, and patients who are too young for conventional therapies. In some embodiments, the subject being administered one or more compounds has not received therapy prior to the administration of the compounds. In certain embodiments, a patient with SMA, is refractory to a therapy when the SMA has not significantly been eradicated and/or the symptoms have not been significantly alleviated. The determination of whether a patient is refractory can be made either in vivo or in vitro by any method known in the art for assaying the effectiveness of a treatment of SMA, using art-accepted meanings of "refractory" in such a context. In various embodiments, a patient with SMA is refractory loss of motor function has not been decreased.

In some embodiments, compounds are administered to a patient to prevent the onset of SMA in a patient at risk of developing SMA. In some embodiments, compounds are administered to a patient who are susceptible to adverse reactions to conventional therapies.

In some embodiments, the subject being administered one or more compounds has not received prior therapy. In other embodiments, one or more compounds are administered to a subject who has received a therapy prior to administration of one or more compounds. In some embodiments, the subject administered a compound experienced adverse side effects to the prior therapy or the prior therapy was discontinued due to unacceptable levels of toxicity to the subject.

The amount of a compound or a form or pharmaceutical composition thereof that increases the amount of any of SMN or SMNΔEx7 protein by modulating UTR-dependent expression of SMN that will be effective in the treatment SMA, can be determined by standard clinical techniques. In vitro or in vivo assays may optionally be employed to help identify optimal dosage ranges. The precise dose to be employed will also depend, e.g., on the route of administration, the type of invention, and the seriousness of the infection, and should be decided according to the judgment of the practitioner and each patient's or subject's circumstances.

Exemplary doses of a compound or a form or pharmaceutical composition thereof that up-regulates any of SMN or SMNΔEx7 protein by modulating UTR-dependent expression of SMN include milligram (mg) or microgram (g) amounts per kilogram (Kg) of subject or sample weight per day such as from about 1 μg per Kg to about 500 mg per Kg per day, from about 1 μg per Kg to about 500 mg per Kg per day, from about 5 μg per Kg to about 100 mg per Kg per day, or from about 10 μg per Kg to about 100 mg per Kg per day. In another embodiment, the dosage is a unit dose of about 0.1 mg, 1 mg, 5 mg, 10 mg, 50 mg, 100 mg, 150 mg, 200 mg, 250 mg, 300 mg, 350 mg, 400 mg, 500 mg, 550 mg, 600 mg, 650 mg, 700 mg, 750 mg, 800 mg or more. In another embodiment, the dosage is a unit dose that ranges from about 0.1 mg to about 1000 mg, from about 1 mg to about 1000 mg, from about 5 mg to about 1000 mg, from about 10 mg to about 500 mg, from about 100 mg to about 500 mg, from about 150 mg to about 500 mg, from about 150 mg to about 1000 mg, from about 250 mg to about 1000 mg, from about 300 mg to about 1000 mg, or from about 500 mg to about 1000 mg.

In certain embodiments, suitable dosage ranges for oral administration are about 0.001 milligram to about 500 milligrams of a compound, per kilogram body weight per day. In specific embodiments of the invention, the oral dose is about 0.01 milligram to about 100 milligrams per kilogram body weight per day, about 0.1 milligram to about 75 milligrams per kilogram body weight per day or about 0.5 milligram to 5 milligrams per kilogram body weight per day. The dosage amounts described herein refer to total amounts administered; that is, if more than one compound is administered, then, in some embodiments, the dosages correspond to the total amount administered. In a specific embodiment, oral compositions contain about 10% to about 95% a compound by weight.

In another embodiment, a subject is administered one or more doses of an effective amount of a compound or a composition, wherein the effective amount is not the same for each dose.

In one embodiment, a compound is administered to a patient in an amount effective to reduce loss of either or both muscle function and strength. In another embodiment, a compound is administered to a patient in an amount effective to increase either or both muscle function and strength. In another embodiment, a compound is administered to a patient to reduce loss of motor function. In another embodiment, a compound is administered to a patient to increase muscle strength. In another embodiment, a compound is administered to a patient to reduce loss of pulmonary function. In another embodiment, a compound is administered to increase pulmonary function.

The present invention also provides methods of SMA, in a subject in need thereof, said methods comprising administering to the subject an effective amount of one or more of the compounds that up-regulate the post-transcriptional expression of SMN alone or in combination with one or more additional agents. In another embodiment, one or more compounds or a form or pharmaceutical composition thereof that up-regulates the post-transcriptional expression of SMN alone or in combination with one or more additional agents may be administered to the subject in combination with a supportive therapy, a pain relief therapy, or other therapy that does not have an effect on SMA.

In some embodiments, one or more compounds or a form thereof that up-regulates the post-transcriptional expression of SMN and one or more additional agents are administered as the same pharmaceutical composition. In certain embodiments, one or more compounds or a form thereof that up-regulates the post-transcriptional expression of SMN and one or more additional agents are administered in different pharmaceutical compositions. In certain embodiments, one or more compounds or a form or pharmaceutical composition thereof that up-regulates the post-transcriptional expression of SMN and one or more additional agents are administered by the same route of administration. In certain embodiments, one or more compounds or a form or pharmaceutical composition thereof that up-regulates the post-transcriptional expression of SMN and one or more additional agents are administered by different routes of administration.

Additional agents that can be used in a combination product with compounds that up-regulate either or both SMN or SMNΔEx7 protein expression for the treatment of SMA include, but are not limited to, small molecules, synthetic drugs, peptides (including cyclic peptides), polypeptides, proteins, nucleic acids (e.g., DNA and RNA nucleotides including, but not limited to antisense nucleotide sequences, triple helices, RNAi, and nucleotide sequences encoding biologically active proteins, polypeptides or peptides), antibodies, synthetic or natural inorganic molecules, mimetic agents, and synthetic or natural organic molecules.

Specific examples of such agents include, but are not limited to, immunomodulatory agents (e.g., interferon), anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone), glucocorticoids, steriods, and non-steriodal anti-inflammatory drugs (e.g., aspirin, ibuprofen, diclofenac, and COX-2 inhibitors), pain relievers, leukotreine antagonists (e.g., montelukast, methyl xanthines, zafirlukast, and zileuton), beta2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), anti-viral agents (e.g., nucleoside analogs (e.g., zidovudine, acyclovir, gangcyclovir, vidarabine, idoxuridine, trifluridine, and ribavirin), foscarnet, amantadine, rimantadine, saquinavir, indinavir, ritonavir, and AZT) and antibiotics (e.g., dactinomycin (formerly actinomycin), bleomycin, erythomycin, penicillin, mithramycin, and anthramycin (AMC)).

In some embodiments, additional agents that can be used in combination with the compounds described herein for the treatment of SMA, include, but are not limited to, agents that increase the transcription of SMN. In certain embodiments, the agent is specific for the transcriptional promoter/enhancer of SMN. In particular embodiments, the agent is specific for a transcription factor that binds to the transcriptional promoter/enhancer of SMN and that increases transcription of SMN. In some embodiments, the agent is specific for a transcriptional repressor that binds to the transcriptional promoter/enhancer of SMN and inhibits transcription, or that binds to a transcription factor of SMN and inhibits the activity of the transcription factor.

Additional agents that can be used in a combination product with compounds of the present invention for the treatment SMA, include, but are not limited to, one or more agents that can improve functional and morphological aspects of muscles or that modulate other proteins involved in muscle growth and regeneration. Such agents include those that down-regulate or reduce the expression of GDF8 (myostatin, or growth and differentiation factor 8) to increase skeletal muscle mass.

In certain other embodiments, the present invention provides methods of treating SMA, in a subject in need thereof, said methods comprising administering to the subject one or more of the compounds that up-regulate (increase/enhance) the post-transcriptional expression of SMN alone or in combination with one or more additional agents each selected from an agent that decreases the expression of GDF8, a different agent that increases the expression of mIGF1, a different agent that increases the expression of α7 integrin, or a different agent that increases the expression of utrophin. In specific embodiments, such additional agent or different agent is not the same as a compound encompassed by the present invention, i.e., a compound that modulates the post-transcriptional expression of SMN via any one of the 5'-UTR, and/or 3'-UTR, or 5'-UTR, and 3'-UTR of SMN.

Any compound or therapy which is known to be useful, or which has been used or is currently being used for the treatment of SMA, can be used in combination with compounds of the present invention as described herein.

Example 1

UTR-Mediated Regulation of SMN Expression

Figure 5:
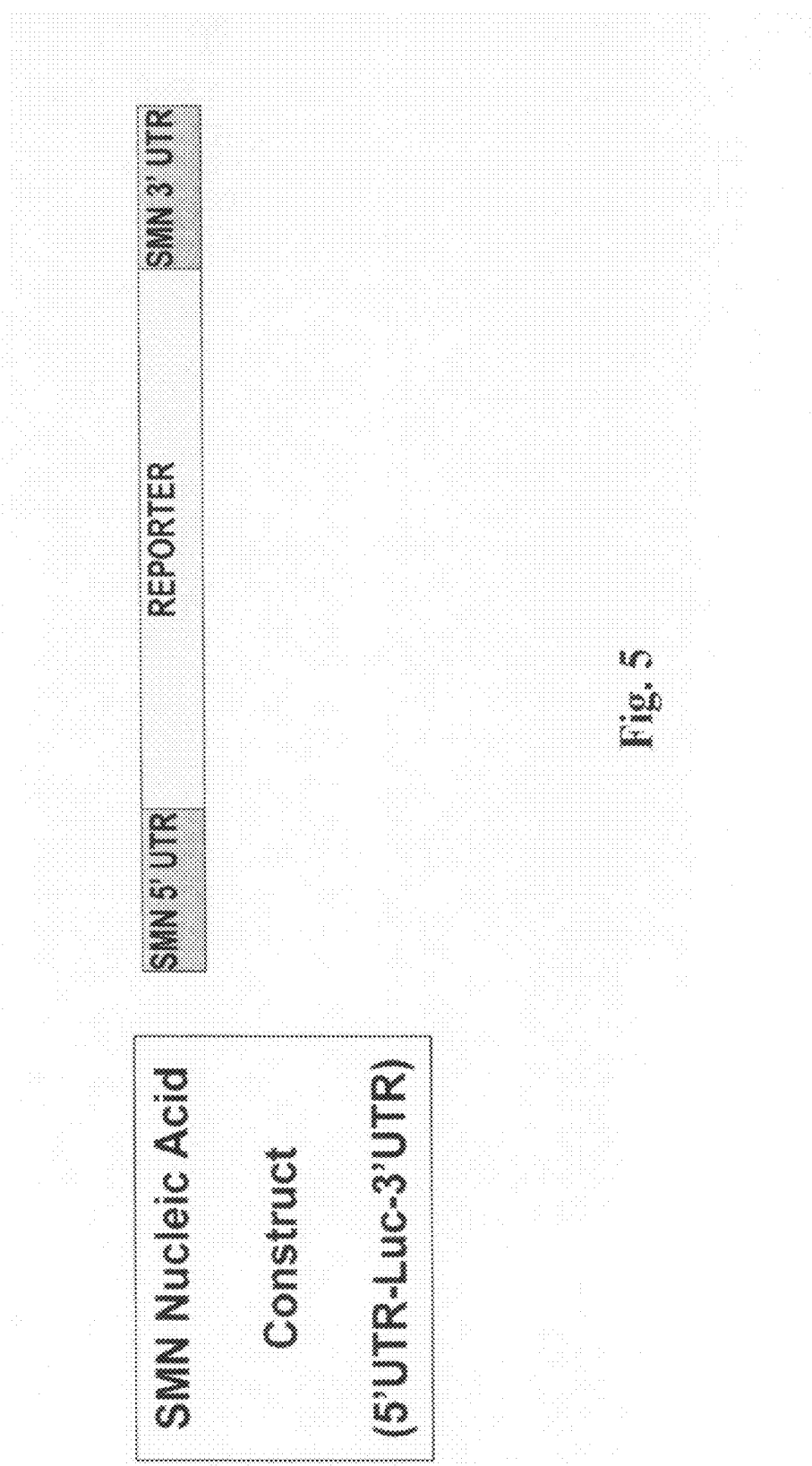
FIG. 5: SMN Construct: Schematic representation of the SMN construct comprising the human SMN 5'-UTR, the luciferase reporter gene, and the 3'-UTR of human SMN2.
Figure 6:
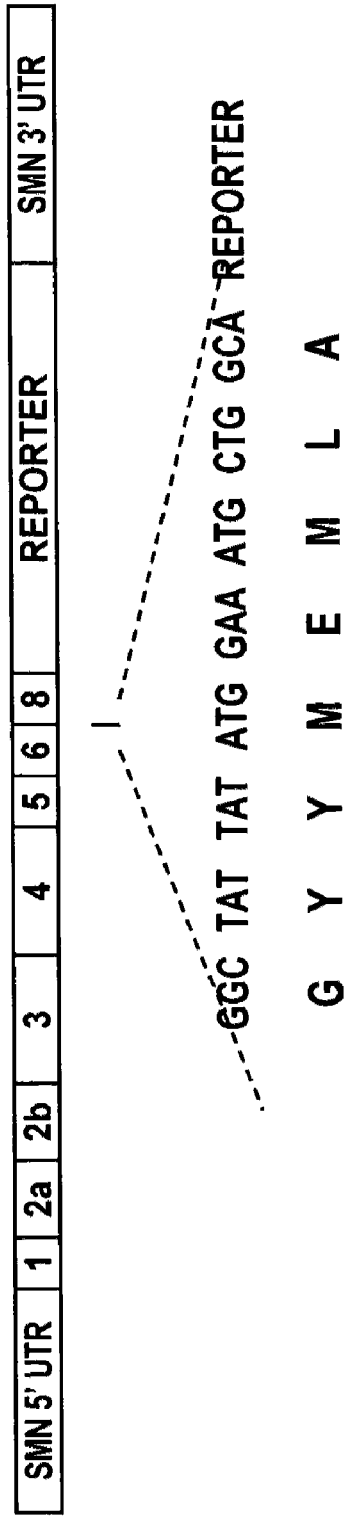
FIG. 6: SMN2-ORF Construct: Schematic representation of the SMN2-ORF construct comprising the 5'-UTR of human SMN, a nucleotide sequence encoding a fusion protein comprising SMNΔEx7 and luciferase, and the 3'-UTR of human SMN 2.

As shown in the following examples, compounds that up-regulate the expression of either of the SMN1 or SMN2 protein have been identified or validated and have the potential to treat SMA. The following constructs were generated and used in the assays of the present invention: (i) a construct comprising the luciferase gene operably linked and downstream of the 5'-UTR of SMN; (ii) a construct comprising the luciferase gene operably linked and upstream of the 3'-UTR of SMN2; (iii) a construct comprising the luciferase gene flanked by the 5'-UTR and 3'-UTR of SMN2 (as shown in FIG. 5); (iv) a construct comprising the luciferase gene operably linked and downstream of SMN in which the ATG codon in the uORF was mutated; (v) a construct comprising the luciferase gene operably linked downstream of nucleotides 30 to 163 of the 5'-UTR of SMN (SEQ ID NO: 5); (vii) a construct comprising the 5'-UTR of SMN, SMNΔEx7 and the luciferase gene, and the 3'-UTR of SMN 2 (as shown in FIG. 6); (viii) a construct comprising the luciferase gene flanked by control UTRs and (ix) a construct comprising, in 5' to 3' order: the 5'-UTR of a control gene, a nucleotide sequence encoding a fusion protein comprising SMNΔEx7 and luciferase, and the 3'-UTR of a control gene. Constructs comprising the 3'-UTR of SMN1 were also tested and gave results similar to the results obtained for the constructs comprising the 3'-UTR of SMN2.

Preparation of the Nucleic Acid Constructs

A high-level expression vector, pcDNA™ 3.1/Hygro (Invitrogen Corp., Carlsbad, Calif.) was used for preparing the constructs. In a pcDNA™ 3.1/Hygro vector, the UTRs and restriction sites associated with cloning, expressing, or cloning and expressing a gene of interest or a reporter gene are removed or replaced.

Certain UTRs and restrictions sites are native high-copy mammalian expression vectors. A vector without UTRs and restriction sites is prepared as follows. Deletion mutagenesis is undertaken to remove UTRs and restriction sites from commercially-available vector, pcDNA™ 3.1/Hygro vector. The vector is constructed to remove a region that starts at the putative transcription start site of a UTR found upstream of the cloning site and continues in the 3' direction to the Hind III restriction site at the multiple cloning site of pcDNA™ 3.1/Hygro vector.

The nucleic acid sequence removed is SEQ ID NO: 6: (5'-AGAGAACCCACTGCTTACTGGCTTATC-GAAATTAATACGACTCACTAT AGGGAGAC-CCAAGCTGGCTAGCGTTTAAACTTA-3').

As such, UTRs that are native to the vector and heterologous to SMN1 or SMN2 are removed. In pcDNA™ 3.1/Hygro, the UTR formed in the region starting at the Xho 1 site of pcDNA™ 3.1/Hygro continuing in the 3' direction and ending at the poly(A) tail, which in pcDNA™ 3.1/Hygro corresponding to the poly(A) tail from bovine growth hormone gene. By removing the nucleic acids from the Xho 1 site to the poly(A) tail, the 3'-UTR native to the vector is removed.

The nucleic acid sequence removed is SEQ ID NO: 7: (5'-CTCGAGTCTAGAGGGCCCGTTTAAAC-CCGCTGATCAGCCTCGACTGTG GCCTTCTAGTTGC-CAGCCATCTGTTGTTGTCCCCTC-CCCCGTCCCTTCCTT GACCCTGGAAGGTGCCACTCCCACTGTCCTTTCCT-3').

For each construct containing 5'-UTR sequences, the 5'-UTR sequences with a start codon were cloned into the vector using the Hind III site and the BamH1 site, which is downstream of the Hind III site. For each construct containing 3'-UTR sequences, the 3'-UTR sequences were cloned into the vector with a stop codon using a Not I site and a Xho I site, which is downstream of the Not I cite. For each construct, the luciferase gene lacking a start codon was cloned into the vector using a BamH1 site and a Not I site, which is downstream of the BamH1 site. The fusion constructs contained the 5'-UTR of SMN or a control gene, the 3'-UTR of SMN or a control gene and the nucleotide sequence encoding the fusion protein comprised of the ORF of SMNΔEx7 is lacking a stop codon and the luciferase gene is lacking the start codon. The nucleotide sequence encoding the fusion protein was cloned into the vector between the BamH1 site and the Not I site.

Reporter Gene Assay

1×10⁴ human embryonic kidney (293H) cells were added per well to 100 μL of medium in a 96-well plate and incubated for 24 hours. The constructs and a control construct were added to each well of the 96-well plate following the manufacturer's protocol using the following amounts of reagents per well: 62.5 ng pcDNA3.1-fluc-target UTRs vector, 3.1 ng Renilla luciferase vector, and 0.375 μL transfection reagent. The cells were incubated for 24 hours. The medium was then replaced with a new aliquot of cultured medium and the cells were incubated for 24 hours. The effect of the UTRs on reporter expression was assessed by quantifying luciferase activity. Luciferase activity was measured by following the dual-luciferase protocol (Promega), wherein 1× passive lysis buffer was prepared, the cell culture medium was replaced with the 1 was assessed by quantifying luciferase activity. Luciferase activity was measured by following the dual-luciferase protocol (Promega), wherein 1× passive lysis buffer was prepared, the cell culture medium was replaced with the 1× passive lysis buffer and incubated for 5 minutes, the substrate was added, and luminescence was measured.

Results

Figure 7:
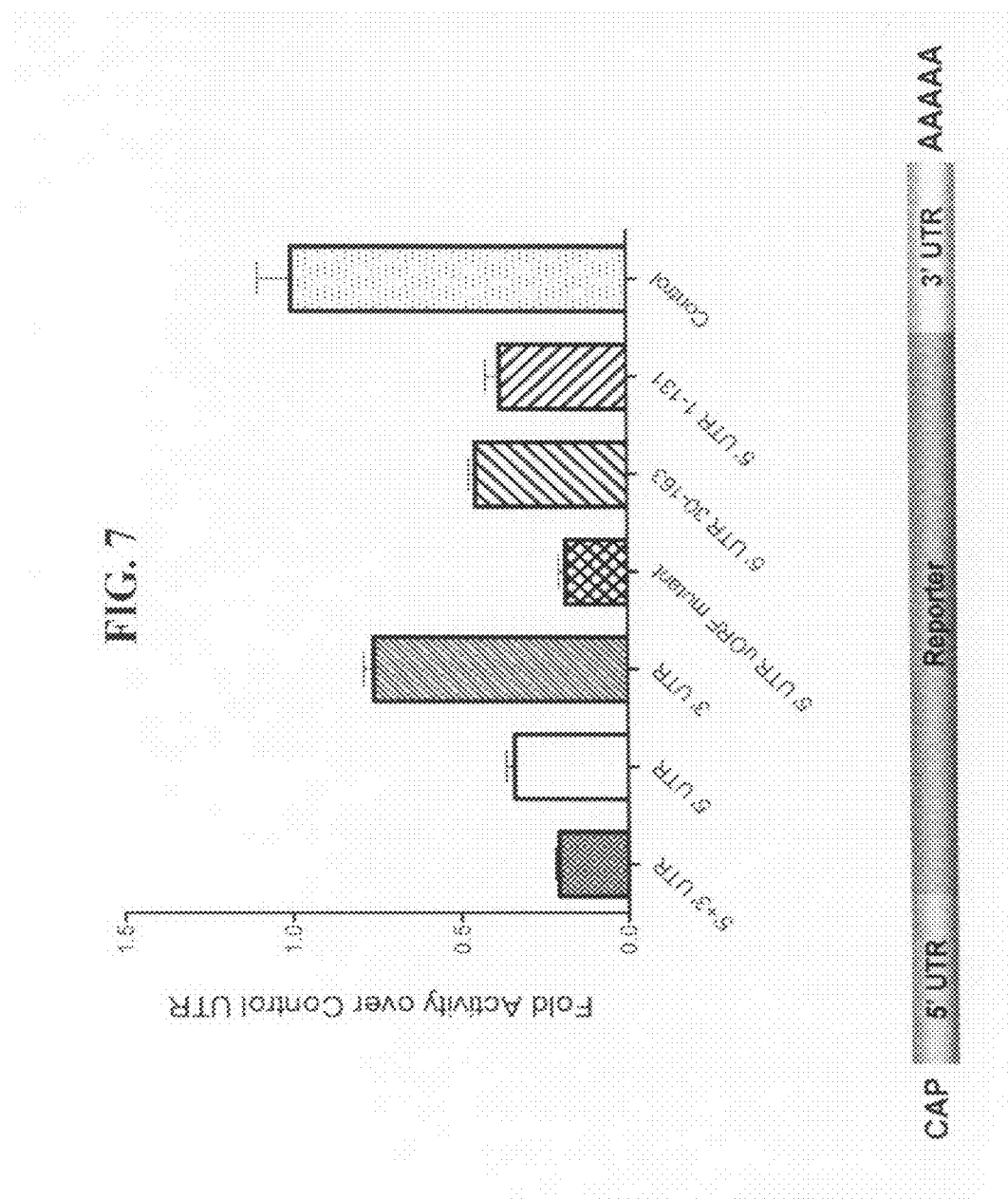
FIG. 7: UTR-Mediated Regulation of SMN Expression: Bar graph showing the affect of various human SMN UTR sequences in controlling SMN protein expression. The following nucleic acid constructs were assessed by measuring fold luciferase activity over a control UTR (y-axis) after being transfected into 293H cells: a construct comprising the luciferase gene flanked by the 5' and 3'-UTRs of human SMN2 (lane 1): a construct comprising the luciferase gene operably linked and downstream of the 5'-UTR of human SMN (lane 2); a construct comprising the luciferase gene operably linked and upstream of the 3'-UTR of human SMN2 (lane 3); a construct comprising the luciferase gene operably linked and downstream of human SMN in which the ATG codon in the uORF was mutated (lane 4); a construct comprising the luciferase gene operably linked downstream of nucleotides 30 to 163 of the 5'-UTR of human SMN (SEQ ID NO: 4; lane 5); a construct comprising the luciferase gene operably linked downstream of nucleotides 1 to 131 of the 5'-UTR of human SMN (SEQ ID NO: 5: lane 6); a construct comprising the luciferase gene flanked by control UTRs that were randomly generated (lane 7).
Figure 8:
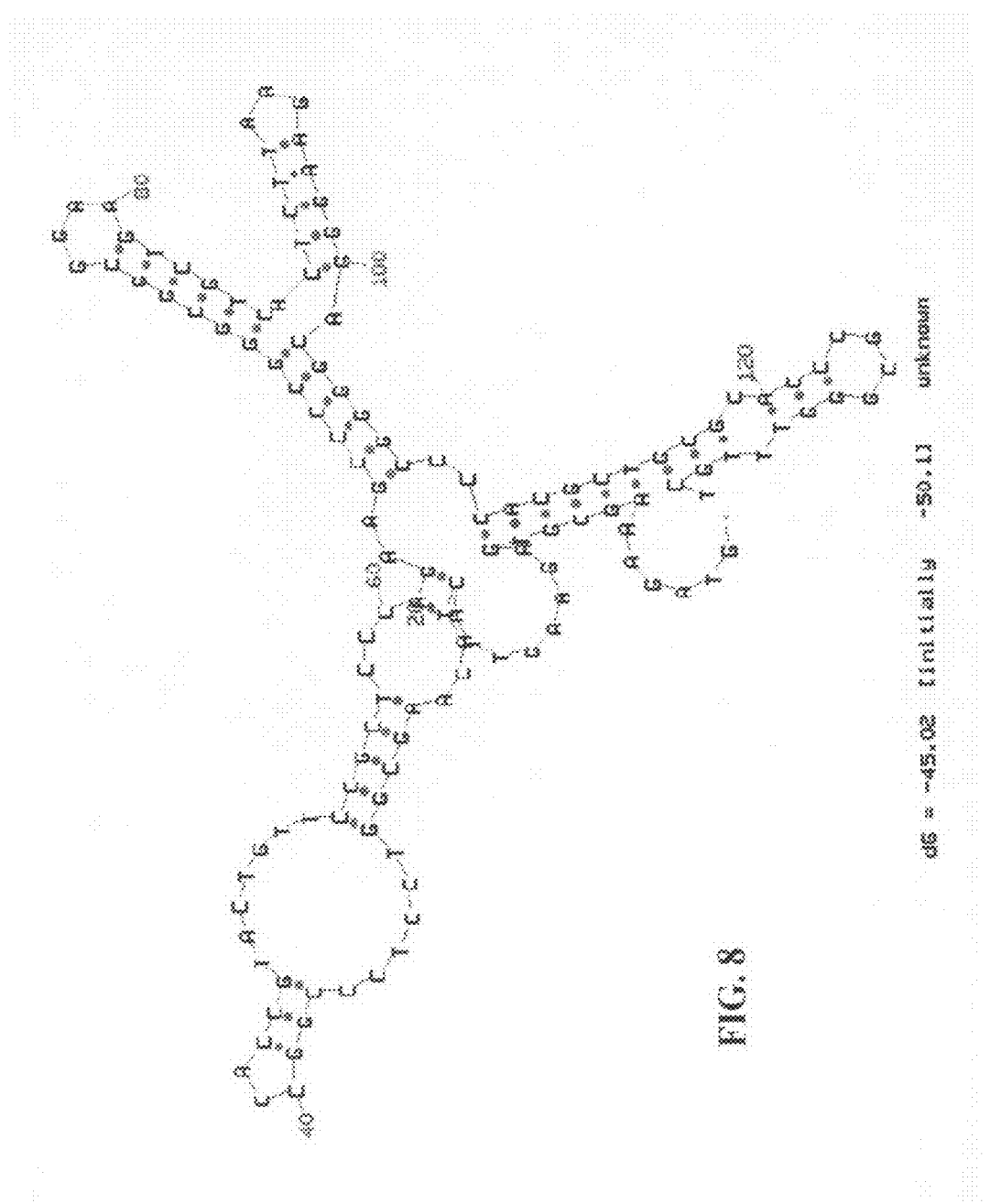
FIG. 8: Secondary Structure of human SMN 5'-UTR 30-163: Schematic representation of the secondary structure of a human SMN 5'-UTR mRNA transcript comprising only nucleotides 30 to 163.
Figure 9:
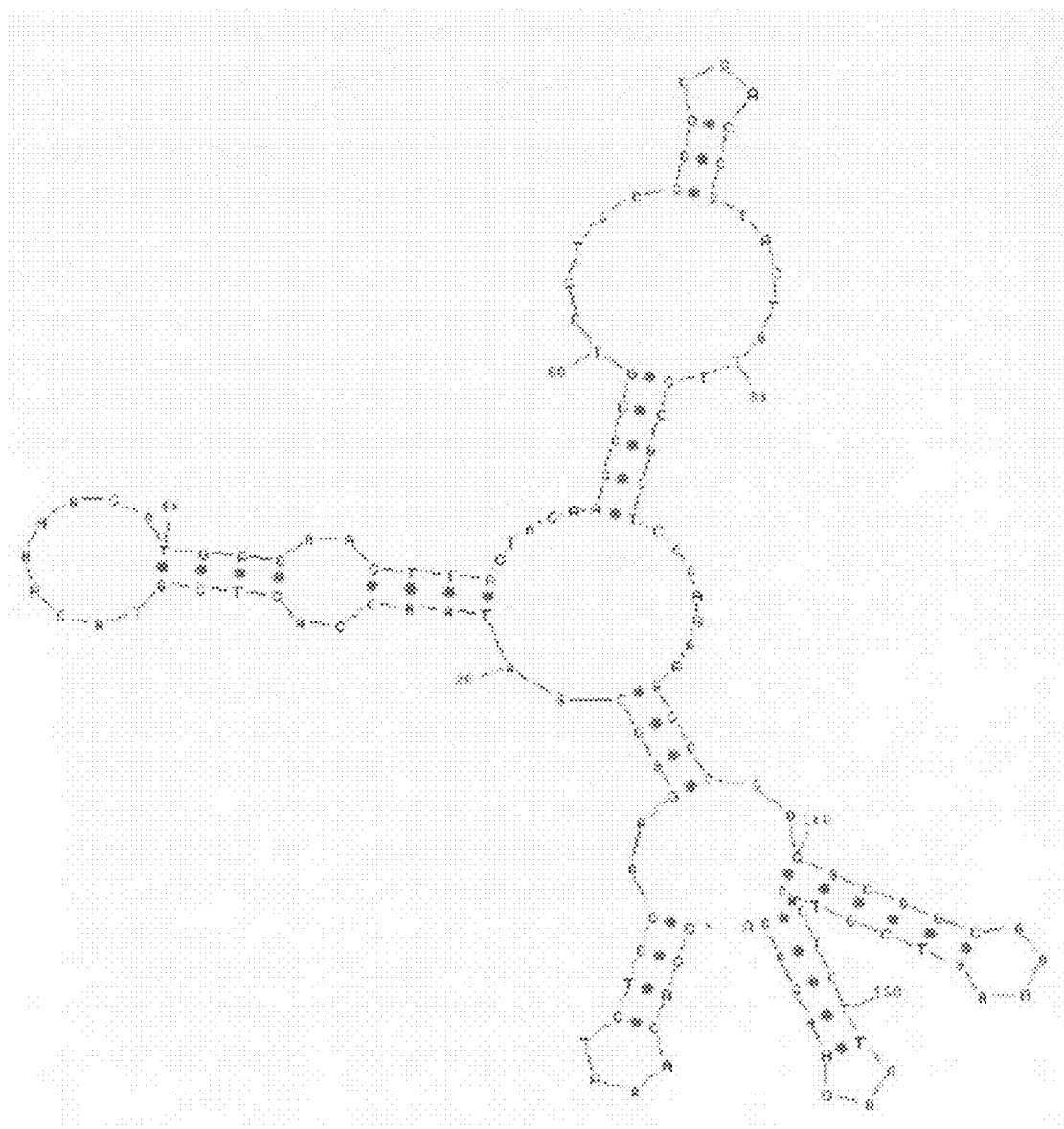
FIG. 9: Secondary Structure of human SMN 5'-UTR 1-131: Schematic representation of the secondary structure of a human SMN 5'-UTR mRNA transcript comprising only nucleotides 1 to 131.
Figure 10:
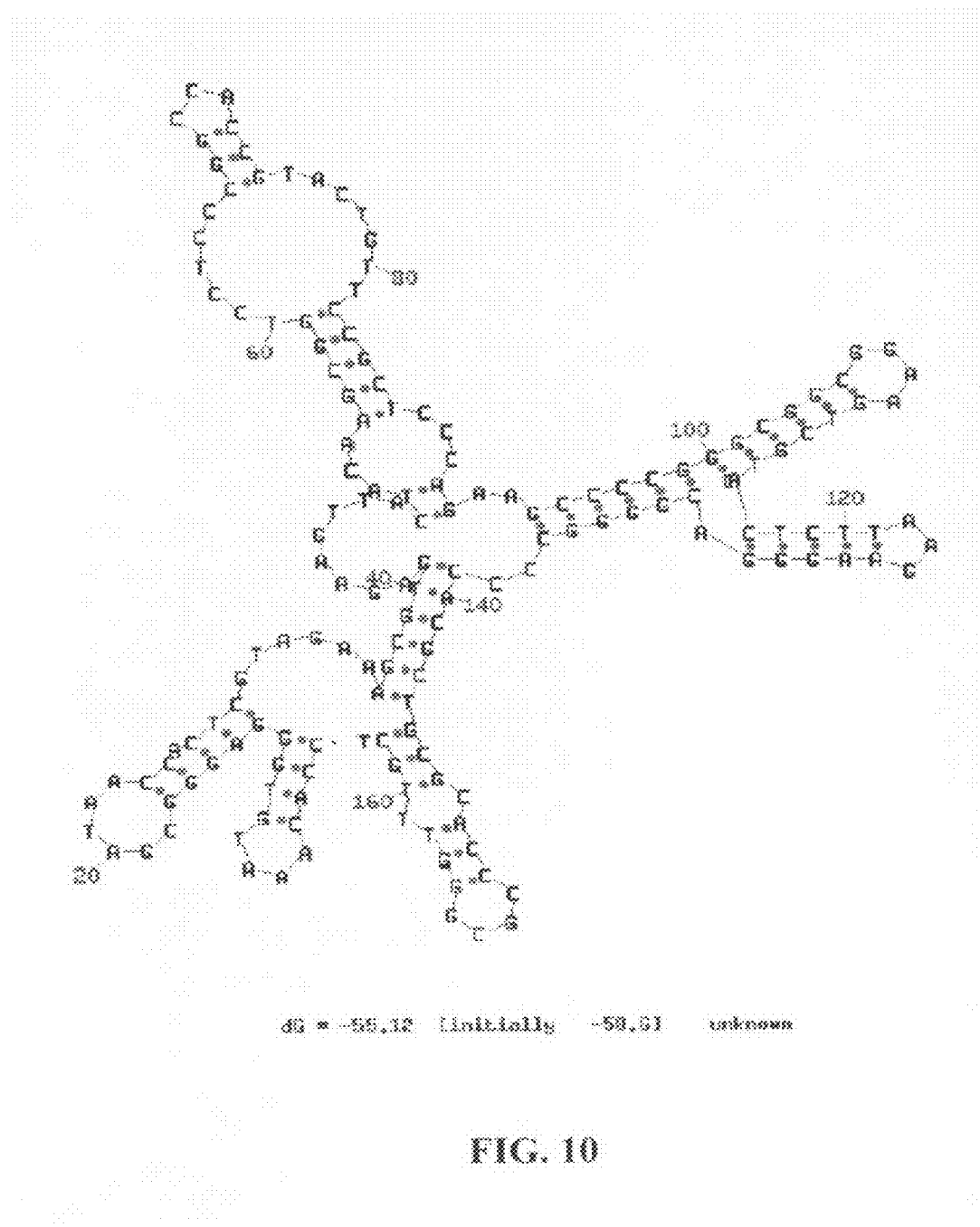
FIG. 10: Secondary Structure of Complete 5'-UTR: Schematic representation of the secondary structure of the entire human SMN 5'-UTR mRNA transcript.

The SMN 5'-UTR inhibited expression of the reporter gene 5-fold whereas the 3'-UTR stimulated expression of luciferase (see FIG. 7, lanes 2 and 3). The 5'-UTR is dominant over the 3'-UTR, as the presence of both UTRs resulted in the inhibition of luciferase expression (see FIG. 7, lane 1). Deletion of the first 29 nucleotides of the 5'-UTR of SMN partially relieved the inhibitory effect of the 5'-UTR (see FIG. 7, lane 5). Deletion of the nucleotides 132 to 163 of the 5'-UTR of SMN also partially relieved the inhibitory effect of the 5'-UTR (see FIG. 7, lane 6). The effect of 5' UTR of SMN was more dramatic than that of the 3'-UTR. The complexity of the secondary structure of SMN 5'-UTR lacking nucleotides 1 to 29 (FIG. 8) and the SMN 5'-UTR lacking nucleotides 132 to 163 (FIG. 9) is less than the secondary structure of the 5'-UTR of SMN (FIG. 10). The results suggest that compounds that reduce the secondary structure of the 5'-UTR may increase post-transcriptional expression of SMN or SMNΔEx7. When the start codon of the uORF was mutated to encode any amino acid other than methionine, the uORF was eliminated from the 5'-UTR. The deletion of this element did not relieve the inhibitory effect of the 5'-UTR on SMN expression (see FIG. 7, lane 4).

Figure 11:
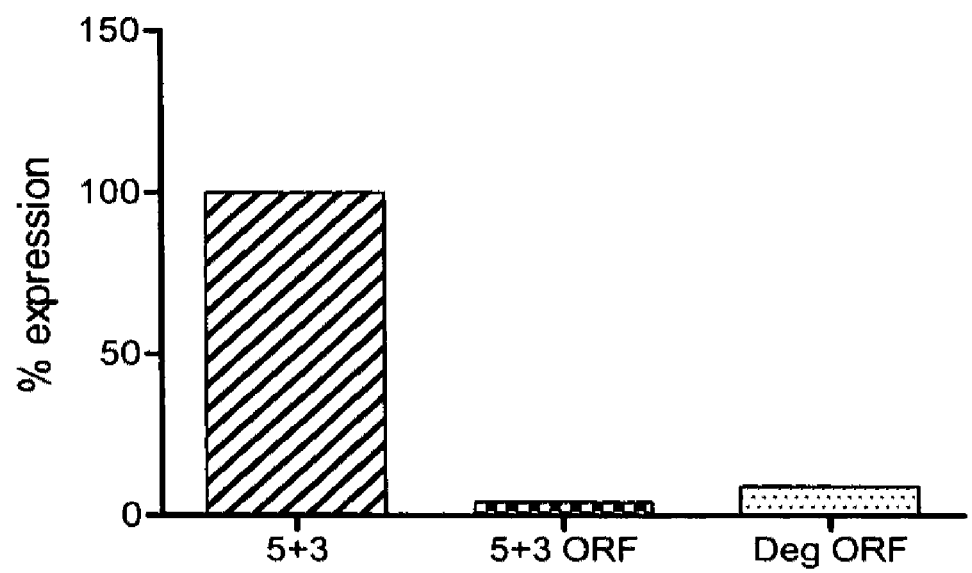
FIG. 11: UTR-ORF-Mediated Regulation of SMN Expression: Bar graph showing the affect of human SMN UTR sequences with the open reading frame of human SMN2 in controlling SMN protein expression. The following nucleic acid constructs were assessed by measuring percentage of luciferase activity over a construct comprising control UTRs (y-axis) after being transfected into 293H cells: a construct comprising the luciferase gene flanked by the 5' and 3'-UTRs of human SMN2 (lane 1); a construct comprising the 5'-UTR of human SMN, a nucleotide sequence encoding a fusion protein comprising SMNΔEx7 and luciferase and the 3'-UTR of human SMN2 (lane 2); a construct comprising the 5'-UTR of a control gene, a nucleotide sequence encoding a fusion protein comprising human SMNΔEx7 and luciferase, and the 3'-UTR of a control gene (lane 3).

The presence of the SMN open reading frame strongly inhibits expression of the reporter gene (see FIGS. 6 and 11). An SMN2-ORF construct with control UTRs instead of the 5'-UTR and 3'-UTR of SMN (Deg ORF) was also used in this experiment. The inhibition effect of SMN-ORF is additive and independent of SMN UTRs.

Example 2

Preparation of the Stable Cell-Line

Stable 293H cell lines containing the firefly luciferase (fLuc) gene flanked by one of SMN1 or SMN2 5'-UTR and 3'-UTR were cultured in DMEM medium supplemented with 10% FBS and 200 ug/mL hygromycin in Fisher T175 flasks. The cells were passaged every 4 days at 1:10 dilution. Cultures are kept in a 37° C. and 5% $CO_2$ incubator. The cells were scaled-up over a three day period before performing the assay. Two confluent T175 flasks were split into twenty T175 flasks (1:10 dilution). Cells were harvested from each confluent flask by removing all of the media and adding 4 mL of warmed trypsin to dislodge the cells. After the cells were dislodged, 16 mL of selective media was added for a final volume of 20 mL. The cells were expanded by adding 2 mL of the harvested cells into ten new T175 flasks plus 25 mL of selective media. The twenty new flasks are placed into the 37° C., 5% $CO_2$ incubator. On the day the assay was performed, the media was removed from the flasks and 3 mL of warmed trypsin was added to dislodge the cells. After the cells were dislodged, 10 mL of nonselective media was to the flask. This was repeated for all twenty flasks and combined into one flask. 100 μL of the above cell culture plus 100 μL of Trypan Blue stain was counted on a hemocytometer. Cells were plated in the presence of 2 μL of a compound to be tested (at final concentration of 7.5 μM with 0.5% DMSO).

Preparation of Standard Plates

Standard 96-well clear Matrix Screen Mates plate were used. 459 μL of 100% DMSO was added to make a 100 mM solution. A fresh 30 mL 10% DMSO stock solution was made by adding 3 mL of 100% DMSO to 27 mL water. The 10% DMSO was used to make serial dilutions of a Puromycin stock solution so that the DMSO concentration remained at 10%.

Using standard techniques known to one skilled in the art, Puromycin was serially diluted to provide 10 mM Stock in 10% DMSO (by diluting 100 μL of 100 mM Stock with 900 μL water), 1 mM Stock in 10% DMSO (by diluting 500 L of mM Stock with 4.5 mL 10% DMSO), 400 μM Stock in 10% DMSO (by diluting 1.6 mL of 1 mM Stock with 2.4 mL 10% DMSO, 20 μM was final amount used in assay), 200 μM Stock in 10% DMSO (by diluting 1 mL of 400 μM Stock with 1 mL 10% DMSO, 10 μM was final amount used in assay), 100 μM Stock in 10% DMSO (by diluting 1 mL of 200 μM Stock with 1 mL 10% DMSO, 5 μM was final amount used in assay), 50 μM Stock in 10% DMSO (by diluting 1 mL of 100 μM Stock with 1 mL 10% DMSO, 2.5 μM was final amount used in assay), 25 μM Stock in 10% DMSO (by diluting 1 mL of 50 μM Stock with 1 mL 10% DMSO, 1.25 μM was final amount used in assay), 12.5 μM Stock in 10% DMSO (by diluting 1 mL of 25 μM Stock with 1 mL 10% DMSO, 0.625 μM was final amount used in assay), 6.25 μM Stock in 10% DMSO (by diluting 1 mL of 12.5 μM Stock with 1 mL 10% DMSO, 0.312 μM was final amount used in assay), 3.125 μM Stock in 10% DMSO (by diluting 1 ml of 6.25 μM Stock with 1 mL 10% DMSO, 0.156 μM was final amount used in assay) and 1.56 μM Stock in 10% DMSO (by diluting 1 mL of 3.125 μM Stock with 1 mL 10% DMSO, 0.078 μM was final amount used in assay).

Firefly Luciferase Substrate Preparation

The firefly luciferase substrate used was Luc Lite Plus Packard #6016969. Luciferase activity was immediately assayed using a ViewLux Imaging system (Perkin Elmer).

Cytotoxicity Assay

To evaluate cytotoxicity of the compounds in the neuroblastoma MC-IXC cell line, the CellTiter-Glo assay (Promega) was utilized. CellTiter-Glo determines the number of viable cells in culture based on quantification of the ATP present, which signals the presence of metabolically active cells. A reduction in cellular ATP is indicative of a cytotoxic or cytostatic effect. The compounds are tested in a 7-point dose response from 30 μM to 0.38 μM. Doxorubicin, a known cytotoxic compound, are used to address the sensitivity of the tested cell line. For relatively sensitive cell lines, such as U937 (a human monocyte cell line), the $CC_{50}$ of doxorubicin ranges from 4 to 10 nM. For cell lines exhibiting an intermediate level of sensitivity to compound treatment such as human Huh7 cells (a human hepatoblastoma cell line), the $CC_{50}$ of doxorubicin ranges from 70 to 300 nM. The sensitivity of MC-IXC cells is similar to that of U937 cells as the $CC_{50}$ of doxorubicin in these cells was 12 nM.

Results

The screening assay was performed by preparing a plates containing test compounds and controls, including wells that contained only vehicle or a high inhibitor concentration and wells that provided an 8-point dose response curve of puromycin, a non-specific standard control inhibitor. The cells were grown overnight in the presence of compounds or controls at 37° C. in 5% $CO_2$. Compounds were screened once for percent inhibition at a 7.5 µM test concentration. After 24 hours, the amount of luminescence was determined using a ViewLux Imaging system (Perkin Elmer). The results for compounds shown in the following table (Table 1) indicates that the compounds of the present invention up-regulate post-transcriptional expression of a nucleic acid construct comprising a reporter gene operably linked to the 5'-UTR and 3'-UTR of the target SMN2 mRNA.

Fold increase values in target mRNA (SMN2) for compounds tested compared to negative control (0.5% DMSO) are shown as follows: wherein one star (*) represents active compounds with a fold increase ratio in a range greater than 1.3 up to 1.6; two stars (**) represent active compounds with a fold increase ratio in a range greater than 1.6 up to 1.8; the term "NA" indicates the compound was not active.

TABLE 1

| Cpd | Ratio |
|---|---|
| 1 | * |
| 2 | ** |
| 3 | NA |
| 4 | ** |

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various patent, patent applications, and publications are cited herein, the disclosures of which are incorporated by reference in their entireties.

---

What is claimed is:

1. A method for human SMN1 mRNA or human SMN2 mRNA translation that is regulated by the untranslated regions (UTRs) of human SMN1 mRNA or human SMN2 mRNA, the method comprising:

(a) contacting a compound with a first host cell engineered to express a first reporter protein translated from a first mRNA transcript comprising a first reporter gene coding sequence operably linked to a first 5'-UTR fragment of human SMN1 or human SMN2 encoded by the nucleotide sequence of SEQ ID NO:4 or 5 and a first 3'-UTR of human SMN1 or human SMN2 encoded by the nucleotide sequence of SEQ ID NO:2 or 3, or a fragment thereof, wherein the first 5'-UTR fragment is upstream of the first reporter gene coding sequence and the first 3'-UTR or a fragment thereof is downstream of the first reporter gene coding sequence, and wherein the first reporter protein is not SMN;

(b) contacting the compound with a second host cell engineered to express a second reporter protein translated from a second mRNA transcript comprising the first reporter gene coding sequence operably linked to a second 5'-UTR or a fragment thereof and a second 3'-UTR or a fragment thereof of a mRNA different from the 5'-UTR of human SMN1 mRNA or human SMN2 mRNA or a fragment thereof and the 3'-UTR of human SMN1 mRNA or human SMN2 mRNA or a fragment thereof, wherein the second 5'-UTR is upstream of the first reporter gene coding sequence and the second 3' UTR is downstream of the first reporter gene coding sequence; and (c) detecting the amount or activity of the first and second reporter proteins (i) an alteration in the amount or activity of the first reporter protein in the presence of the compound relative to the amount or activity in the absence of the compound or the presence of a negative control, and (ii) no alteration in or not a substantially altered amount or activity of the second reporter protein in the presence of the compound relative to the amount or activity of the second reporter protein in the absence of the compound or the presence of the negative control indicates that the compound modulates human SMN1 mRNA or human SMN2 mRNA translation that is regulated by the UTRs of human SMN1 mRNA or human SMN2 mRNA.

2. The method of claim 1, wherein an increase in the amount or activity of the first reporter protein in the presence of the compound relative to the amount or activity of the first reporter protein in the absence of the compound or the presence of a negative control indicates that the compound upregulates human SMN1 mRNA or human SMN2 mRNA translation that is regulated by the UTRs of human SMN1 or human SMN2 mRNA.

3. The method of claim 1, wherein the first reporter gene coding sequence is operably linked to the 5'-UTR fragment of human SMN1 or human SMN2 encoded by the nucleotide sequence of SEQ ID NO:4 or 5 and the first 3'-UTR of human SMN1 encoded by the nucleotide sequence of SEQ ID NO:2 or a fragment thereof.

4. The method of claim 1, wherein the first reporter gene coding sequence is operably linked to the first 5'-UTR fragment of human SMN1 or human SMN2 encoded by the nucleotide sequence of SEQ ID NO:4 or 5 and the first 3'-UTR of human SMN2 encoded by the nucleotide sequence of SEQ ID NO:3 or a fragment thereof.

5. The method of claim 1, wherein the first reporter protein is a fusion protein comprising SMNΔEx7 and luciferase.

6. The method of claim 1, wherein the first and second host cells are a RD cell, hybridoma, pre-B cell, 293 cell, 293T cell, 293H cell, HeLa cell, HepG2 cell, K562 cell, 3T3 cell, MCF7 cell, SkBr3 cell, BT474 cell, A204 cell, MC-IXC cell, SK-N-MC cell, SK-N-MC cell, SK-N-DZ cell, SH-SY5Y cell or BE(2)-C cell.

7. The method of claim 1, wherein the first and second host cells are stably transfected with a nucleic acid construct encoding the first and second mRNA transcripts, respectively.

8. The method of claim 1, wherein the first reporter gene coding sequence is operably linked to a fragment of the 5'-UTR encoded by the nucleotide sequence of SEQ ID NO:4.

9. The method of claim 1, wherein the first reporter gene coding sequence is operably linked to a fragment of the 5'-UTR encoded by the nucleotide of SEQ ID NO:5.

10. A method for screening for a compound that modulates human SMN1 mRNA or human SMN2 mRNA translation that is regulated by the untranslated regions (UTRs) of human SMN1 or human SMN2 mRNA, the method comprising:

(a) contacting a compound with a first composition comprising a first cell-free extract and a first mRNA transcript comprising a first reporter gene coding sequence operably linked to a first 5'-UTR fragment of human SMN1 or human SMN2 encoded by the nucleotide sequence of SEQ ID NO: 4 or 5 and a first 3'-UTR of human SMN1 or human SMN2 encoded by the nucleotide sequence of SEQ ID NO:2 or 3, or a fragment thereof, wherein the first 5'-UTR fragment is upstream of the first reporter gene coding sequence and the first 3'-UTR or a fragment thereof is downstream of the first reporter gene coding sequence, and wherein the first reporter protein is not SMN;

(b) contacting the compound with a second composition comprising a second cell-free extract and a second mRNA transcript comprising the first reporter gene coding sequence operably linked to a second 5'-UTR or a fragment thereof and a second 3'-UTR or a fragment thereof of a mRNA different from the 5'-UTR of human SMN1 mRNA or human SMN2 mRNA or a fragment thereof and the 3'-UTR of human SMN1 mRNA or human SMN2 mRNA or a fragment thereof, wherein the second 5'-UTR is upstream of the first reporter gene coding sequence and the second 3' UTR is downstream of the first reporter gene coding sequence, and wherein the first reporter protein is not SMN; and (c) detecting the amount or activity of the first and second reporter proteins translated from the first and second mRNA transcripts, respectively, wherein (i) an alteration in the amount or activity of the first reporter protein in the presence of the compound relative to the amount or activity in the absence of the compound or the presence of a negative control, and (ii) no alteration in or not a substantially altered amount or activity of the second reporter protein in the presence of the compound relative to the amount or activity of the second reporter protein in the absence of the compound or the presence of the negative control indicates that the compound modulates human SMN1 mRNA or human SMN2 mRNA translation that is regulated by the UTRs of human SMN1 mRNA or human SMN2 mRNA.

11. The method of claim 10, wherein an increase in the amount or activity of the first reporter protein in the presence of the compound relative the amount or activity of the first reporter protein in the absence of the compound or the presence of a negative control indicates that the compound upregulates human SMN1 mRNA or human SMN2 mRNA translation that is regulated by the UTR of human SMN1 or human SMN2 mRNA.

12. The method of claim 10, wherein the first reporter gene coding sequence is operably linked to the first 5'-UTR of human SMN1 or human SMN2 encoded by the nucleotide sequence of SEQ ID NO:4 or 5 and the first 3'-UTR of human SMN1 encoded by the nucleotide sequence of SEQ ID NO:2 or a fragment thereof.

13. The method of claim 10, wherein the first reporter gene coding sequence is operably linked to the first 5'-UTR of human SMN1 or human SMN2 encoded by the nucleotide sequence of SEQ ID NO:4 or 5 and the first 3'-UTR of human SMN2 encoded by the nucleotide sequence of SEQ ID NO:3 or a fragment thereof.

14. The method of claim 10, wherein the first reporter protein is a fusion protein comprising SMNΔEx7 and luciferase.

15. The method of claim 10, wherein the first and second cell-free extracts are human cell-free extracts.

16. The method of claim 10, wherein the first reporter gene coding sequence is operably linked to a fragment of the 5'-UTR encoded by the nucleotide sequence of SEQ ID NO:4.

17. The method of claim 10, wherein the first reporter gene coding sequence is operably linked to a fragment of the 5'-UTR encoded by the nucleotide sequence SEQ ID NO:5.

18. A method for screening for a compound that modulates human SMN1 mRNA or human SMN2 mRNA translation that is regulated by the untranslated regions (UTRs) of human SMN1 mRNA or human SMN2 mRNA, the method comprising:

(a) contacting a compound with a first host cell engineered to express a first reporter protein translated from a first mRNA transcript comprising a first reporter gene coding sequence operably linked to a modified 5'-UTR of human SMN and the 3'-UTR of human SMN1 or human SMN2 encoded by the nucleotide sequence of SEQ ID NO: 2 or 3, or a fragment thereof, wherein the modified 5'-UTR is upstream of the first reporter gene coding sequence and the 3'-UTR or a fragment thereof is downstream of the first reporter gene coding sequence, wherein the first reporter protein is not SMN, and wherein the modified 5'-UTR of human SMN is encoded by (1) the nucleotide sequence of SEQ ID NO:1 which has a mutation that mutates or eliminates the ATG site at nucleotide positions 7-9, or (2) the nucleotide sequence of SEQ ID NO: 1 which has a mutation that deletes the uORF at nucleotide positions 7-33;

(b) contacting the compound with a second host cell expressing a second reporter protein translated from a second mRNA transcript comprising a first reporter gene coding sequence operably linked to a second 5'-UTR or a fragment thereof and a second 3'-UTR or a fragment thereof of a mRNA different from the modified 5'-UTR of human SMN and said 3'-UTR of human SMN1 or human SMN2 or a fragment thereof, wherein the second 5'-UTR is upstream of the first reporter gene coding sequence and the second 3' UTR is downstream of the first reporter gene coding sequence; and (c) detecting the amount or activity of the first and second reporter proteins, wherein (i) an alteration in the amount or activity of the first reporter protein in the presence of the compound relative to the amount or activity in the absence of the compound or the presence of a negative control, and (ii) no alteration in or not a substantially altered amount or activity of the second reporter protein in the presence of the compound relative to the amount or activity of the second reporter protein in the absence of the compound or the presence of the negative control indicates that the compound modulates human SMN1 mRNA or human SMN2 mRNA translation that is regulated by the UTRs of human SMN1 mRNA or human SMN2 mRNA.

19. The method of claim 18, wherein the modified 5'-UTR of human SMN is encoded by the nucleotide sequence of SEQ ID NO:1 which has a mutation that mutates or eliminates the ATG site at nucleotide positions 7-9.

20. The method of claim 18, wherein the modified 5'-UTR of human SMN is encoded by the nucleotide sequence of SEQ ID NO: 1 which has a mutation that deletes the uORF at nucleotide positions 7-33.

21. A method for screening for a compound that modulates human SMN1 mRNA or human SMN2 mRNA translation that is regulated by the untranslated regions (UTRs) of human SMN1 or human SMN2 mRNA comprising:

(a) contacting a compound with a first composition comprising a first cell-free extract and a first mRNA transcript comprising a first reporter gene coding sequence operably linked to a modified 5'-UTR of human SMN and a 3'-UTR of human SMN1 or human SMN2 encoded by the nucleotide sequence of SEQ ID NO:2 or 3, or a fragment thereof, wherein the modified 5'-UTR is upstream of the first reporter gene coding sequence and the 3'-UTR or a fragment thereof is downstream of the first reporter gene coding sequence, and wherein the modified 5'-UTR of human SMN is encoded by (1) the nucleotide sequence of SEQ ID NO:1 which has a mutation that mutates or eliminates the ATG site at nucleotide positions 7-9, or (2) the nucleotide sequence of SEQ ID NO: 1 which has a mutation that deletes the uORF at nucleotide positions 7-33;

(b) contacting the compound with a second composition comprising a second cell-free extract and a second mRNA transcript comprising the first reporter gene coding sequence operably linked to a second 5'-UTR or a fragment thereof and a second 3'-UTR or a fragment thereof of a mRNA different from the modified 5'-UTR of human SMN and said 3'-UTR of human SMN1 or human SMN2 or a fragment thereof, wherein the second 5'-UTR is upstream of the first reporter gene coding sequence and the second 3' UTR is downstream of the first reporter gene coding sequence; and (c) detecting the amount or activity of the first and second reporter proteins translated from the first and second mRNA transcripts, respectively, wherein (i) an alteration in the amount or activity of the first reporter protein in the presence of the compound relative to the amount or activity in the absence of the compound or the presence of a negative control, and (ii) no alteration in or not a substantially altered amount or activity of the second reporter protein in the presence of the compound relative to the amount or activity of the second reporter protein in the absence of the compound or the presence of the negative control indicates that the compound modulates human SMN1 mRNA or human SMN2 mRNA translation that is regulated by the UTRs of human SMN1 mRNA or human SMN2 mRNA.

22. The method of claim 21, wherein the modified 5'-UTR of human SMN is encoded by the nucleotide sequence of SEQ ID NO:1 which has a mutation that mutates or eliminates the ATG site at nucleotide positions 7-9.

23. The method of claim 21, wherein the modified 5'-UTR of human SMN is encoded by the nucleotide sequence of SEQ ID NO: 1 which has a mutation that deletes the uORF of nucleotide at positions 7-33.

24. A method for human SMN1 mRNA or human SMN2 mRNA translation that is regulated by the untranslated regions (UTRs) of human SMN1 mRNA or human SMN2 mRNA, the method comprising:

a) contacting a compound with a first host cell engineered to express a first reporter protein translated from a first mRNA transcript comprising a first reporter gene coding sequence operably linked to a first 5'-UTR of human SMN1 or human SMN2 encoded by the nucleotide sequence of SEQ ID NO:1 or a fragment thereof and a first 3'-UTR of human SMN1 or human SMN2 encoded by the nucleotide sequence of SEQ ID NO:2 or 3, or a fragment thereof, wherein the first 5'-UTR or a fragment thereof is upstream of the first reporter gene coding sequence and the first 3'-UTR or a fragment thereof is downstream of the first reporter gene coding sequence, and wherein the first reporter protein is not SMN, and wherein the compound is (E)-N-((5-bromothiophen-2-yl)methylene)-4-(6-methylbenzo[d]thiazol-2-yl) aniline, 3,4,4-trimethyl-1-phenylpent-1-yn-3-ol, 2-amino-3-(2-(4-chlorophenyl)-2-oxoethyl)thiazol-3-ium, or N-cyclohexyl-1-phenyl-1H-pyrazolo[3,4-d]pyrimidin-4-amine;

(b) contacting the compound with a second host cell engineered to express a second reporter protein translated from a second mRNA transcript comprising the first reporter gene coding sequence operably linked to a second 5'-UTR or a fragment thereof and a second 3'-UTR or a fragment thereof of a mRNA different from the 5'-UTR of human SMN1 mRNA or human SMN2 mRNA or a fragment thereof and the 3'-UTR of human SMN1 mRNA or human SMN2 mRNA or a fragment thereof, wherein the second 5'-UTR is upstream of the first reporter gene coding sequence and the second 3' UTR is downstream of the first reporter gene coding sequence; and (c) detecting the amount or activity of the first and second reporter proteins (i) an alteration in the amount or activity of the first reporter protein in the presence of the compound relative to the amount or activity in the absence of the compound or the presence of a negative control, and (ii) no alteration in or not a substantially altered amount or activity of the second reporter protein in the presence of the compound relative to the amount or activity of the second reporter protein in the absence of the compound or the presence of the negative control indicates that the compound modulates human SMN1 mRNA or human SMN2 mRNA translation that is regulated by the UTRs of human SMN1 mRNA or human SMN2 mRNA.

25. A method for screening for a compound that modulates human SMN1 mRNA or human SMN2 mRNA translation that is regulated by the untranslated regions (UTRs) of human SMN1 or human SMN2 mRNA, the method comprising:

(a) contacting a compound with a first composition comprising a first cell-free extract and a first mRNA transcript comprising a first reporter gene coding sequence operably linked to a first 5'-UTR of human SMN1 or human SMN2 encoded by the nucleotide sequence of SEQ ID NO: 1 or a fragment thereof and a first 3'-UTR of human SMN1 or human SMN2 encoded by the nucleotide sequence of SEQ ID NO:2 or 3, or a fragment thereof, wherein the first 5'-UTR or a fragment thereof is upstream of the first reporter gene coding sequence and the first 3'-UTR or a fragment thereof is downstream of the first reporter gene coding sequence, and wherein the first reporter protein is not SMN, and wherein the compound is (E)-N-((5-bromothiophen-2-yl)methylene)-4-(6-methylbenzo[d]thiazol-2-yl)aniline, 3,4,4-trimethyl-1-phenylpent-1-yn-3-ol, 2-amino-3-(2-(4-chlorophenyl)-2-oxoethyl)thiazol-3-ium, or N-cyclohexyl-1-phenyl-1H-pyrazolo[3,4-d]pyrimidin-4-amine;

(b) contacting the compound with a second composition comprising a second cell-free extract and a second mRNA transcript comprising the first reporter gene coding sequence operably linked to a second 5'-UTR or a fragment thereof and a second 3'-UTR or a fragment thereof of a mRNA different from the 5'-UTR of human SMN1 mRNA or human SMN2 mRNA or a fragment thereof and the 3'-UTR of human SMN1 mRNA or human SMN2 mRNA or a fragment thereof, wherein the second 5'-UTR is upstream of the first reporter gene coding sequence and the second 3' UTR is downstream of the first reporter gene coding sequence, and wherein the first reporter protein is not SMN; and (c) detecting the amount or activity of the first and second reporter proteins translated from the first and second mRNA transcripts, respectively, wherein (i) an alteration in the amount or activity of the first reporter protein in the presence of the compound relative to the amount or activity in the absence of the compound or the presence of a negative control, and (ii) no alteration in or not a substantially altered amount or activity of the second reporter protein in the presence of the compound relative to the amount or activity of the second reporter protein in the absence of the compound or the presence of the negative control indicates that the compound modulates human SMN1 mRNA or human SMN2 mRNA translation that is regulated by the UTRs of human SMN1 mRNA or human SMN2 mRNA.

* * * * *

SEQUENCE LISTING

```
<160> NUMBER OF SEQ ID NOS: 7

<210> SEQ ID NO 1
<211> LENGTH: 163
<212> TYPE: DNA
<213> ORGANISM: Artificial Sequence
<220> FEATURE:
<223> OTHER INFORMATION: SMN 5 prime Untranslated Region

<400> SEQUENCE: 1
ccacaaatgt gggagggcga taaccactcg tagaaagcgt gagaagttac tacaagcggt      60
cctcccggcc accgtactgt tccgctccca gaagcccggg gcggcggaag tcgtcactct     120
taagaaggga cggggcccca cgctgcgcac ccgcgggttt gct                       163

<210> SEQ ID NO 2
<211> LENGTH: 577
<212> TYPE: DNA
<213> ORGANISM: Artificial Sequence
<220> FEATURE:
<223> OTHER INFORMATION: SMN1 3 prime Untranslated Region

<400> SEQUENCE: 2
ggagaaatgc tggcatagag cagcactaaa tgacaccact aaagaaacga tcagacagat      60
ctggaatgtg aagcgttata gaagataact ggcctcattt cttcaaaata tcaagtgttg     120
ggaaagaaaa aaggaagtgg aatgggtaac tcttcttgat taaaagttat gtaataacca     180
aatgcaatgt gaaatatttt actggactct attttgaaaa accatctgta aaagactgag     240
gtgggggtgg gaggccagca cggtggtgag gcagttgaga aaatttgaat gtggattaga     300
ttttgaatga tattggataa ttattggtaa ttttatgagc tgtgagaagg gtgttgtagt     360
ttataaaaga ctgtcttaat ttgcatactt aagcatttag gaatgaagtg ttagagtgtc     420
ttaaaatgtt tcaaatggtt taacaaaatg tatgtgaggc gtatgtggca aaatgttaca     480
gaatctaact ggtggacatg gctgttcatt gtactgtttt tttctatctt ctatatgttt     540
aaaagtatat aataaaaata tttaatttt ttttaaa                              577
```

```
<210> SEQ ID NO 3
<211> LENGTH: 559
<212> TYPE: DNA
<213> ORGANISM: Artificial Sequence
<220> FEATURE:
<223> OTHER INFORMATION: SMN2 3 prime Untranslated Region

<400> SEQUENCE: 3
agcagcacta aatgacacca ctaaagaaac gatcagacag atctggaatg tgaagcgtta      60
tagaagataa ctggcctcat tcttcaaaa tatcaagtgt tgggaaagaa aaaggaagt      120 ggaatgggta actcttcttg attaaaagtt atgtaataac caaatgcaat gtgaaatatt    180
ttactggact ctattttgaa aaccatctg taaaagactg aggtgggggt gggaggccag    240
cacggtggtg aggcagttga gaaaatttga atgtggatta gattttgaat gatattggat    300
aattattggt aattttatga gctgtgagaa gggtgttgta gtttataaaa gactgtctta    360
atttgcatac ttaagcattt aggaatgaag tgttagagtg tcttaaaatg tttcaaatgg    420
tttaacaaaa tgtatgtgag gcgtatgtgg caaaatgtta cagaatctaa ctggtggaca    480
tggctgttca ttgtactgtt ttttctatc ttctatatgt ttaaaagtat ataataaaaa     540
tatttaattt ttttttaaa                                                 559

<210> SEQ ID NO 4
<211> LENGTH: 134
<212> TYPE: DNA
<213> ORGANISM: Artificial Sequence
<220> FEATURE:
<223> OTHER INFORMATION: SMN 5 prime Untranslated Region (Nucleotides
      30-163)

<400> SEQUENCE: 4
gtagaaagcg tgagaagtta ctacaagcgg tcctcccggc caccgtactg ttccgctccc     60
agaagccccg gcggcggaa gtcgtcactc ttaagaaggg acggggcccc acgctgcgca    120
cccgcgggtt tgct                                                      134

<210> SEQ ID NO 5
<211> LENGTH: 131
<212> TYPE: DNA
<213> ORGANISM: Artificial Sequence
<220> FEATURE:
<223> OTHER INFORMATION: SMN 5 prime Untranslated Region (Nucleotides
      1-131)

<400> SEQUENCE: 5
ccacaaatgt gggagggcga taaccactcg tagaaagcgt gagaagttac tacaagcggt     60
cctcccggcc accgtactgt tccgctccca gaagccccgg gcggcggaag tcgtcactct    120
taagaaggga c                                                         131

<210> SEQ ID NO 6
<211> LENGTH: 81
<212> TYPE: DNA
<213> ORGANISM: Artificial Sequence
<220> FEATURE:
<223> OTHER INFORMATION: Nucleic acid sequence removed from pcDNA
      Trademark 3.1-Hygro vector

<400> SEQUENCE: 6
agagaaccca ctgcttactg gcttatcgaa attaatacga ctcactatag ggagacccaa     60
gctggctagc gtttaaactt a                                              81
```

```
<210> SEQ ID NO 7
<211> LENGTH: 134
<212> TYPE: DNA
<213> ORGANISM: Artificial Sequence
<220> FEATURE:
<223> OTHER INFORMATION: Nucleic acid sequence removed from pcDNA
      Trademark 3.1-Hygro vector from Xho 1 site to the poly(A) tail

<400> SEQUENCE: 7
ctcgagtcta gagggcccgt ttaaacccgc tgatcagcct cgactgtggc cttctagttg      60
ccagccatct gttgttgtcc cctcccccgt cccttccttg accctggaag gtgccactcc    120
cactgtcctt tcct                                                      134
```